US006228129B1

(12) United States Patent
de la Mettrie et al.

(10) Patent No.: US 6,228,129 B1
(45) Date of Patent: May 8, 2001

(54) OXIDATION DYEING COMPOSITION FOR KERATIN FIBRES AND DYEING METHOD USING SAID COMPOSITION

(75) Inventors: Roland de la Mettrie, Le Vesinet; Jean Cotteret, Verneuil-sur-Seine; Arnaud de Labbey, Aulnay Sous Bois; Mireille Maubru, Chatou, all of (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/319,166

(22) PCT Filed: Sep. 28, 1998

(86) PCT No.: PCT/FR98/02075

§ 371 Date: Jul. 1, 1999

§ 102(e) Date: Jul. 1, 1999

(87) PCT Pub. No.: WO99/17730

PCT Pub. Date: Apr. 15, 1999

(30) Foreign Application Priority Data

Oct. 3, 1997 (FR) .................................................. 97-12353

(51) Int. Cl.[7] ..................................................... A61K 7/13
(52) U.S. Cl. ..................... 8/401; 8/407; 8/409; 8/410; 8/416; 8/421; 8/423; 8/426
(58) Field of Search .............................. 8/401, 407, 409, 8/410, 416, 421, 423, 426

(56) References Cited

U.S. PATENT DOCUMENTS

| 3,907,799 | 9/1975 | O'Brien et al. ...................... 544/281 |
|---|---|---|
| 4,961,925 | 10/1990 | Tsujino et al. ............................ 8/401 |
| 5,015,260 | * 5/1991 | Tanura et al. ............................. 8/408 |
| 5,104,414 | * 4/1992 | Tanura et al. ............................. 8/408 |
| 5,334,225 | * 8/1994 | Ogawa et al. ............................ 8/408 |
| 5,833,969 | * 11/1998 | Tsujino et al. .................. 424/70.122 |
| 5,849,041 | * 12/1998 | Kunz et al. ............................... 8/408 |
| 5,879,412 | * 3/1999 | Rondeau et al. .......................... 8/411 |
| 5,919,273 | * 7/1999 | Rondeau et al. .......................... 8/412 |
| 6,027,719 | * 2/2000 | Tomura et al. .................... 424/78.02 |

FOREIGN PATENT DOCUMENTS

| 23 59 399 | 6/1975 | (DE) . |
|---|---|---|
| 38 43 892 | 6/1990 | (DE) . |
| 41 33 957 | 4/1993 | (DE) . |
| 195 43 988 | 5/1997 | (DE) . |
| 195 47 991 | 6/1997 | (DE) . |
| 0 310 675 | 4/1989 | (EP) . |
| 0 628 559 | 12/1994 | (EP) . |
| 0 714 954 | 6/1996 | (EP) . |
| 0 716 846 | 6/1996 | (EP) . |
| 0 766 958 | 4/1997 | (EP) . |
| 0 795 313 | 9/1997 | (EP) . |
| 2 586 913 | 3/1987 | (FR) . |
| 2 733 749 | 11/1996 | (FR) . |
| 1 026 978 | 4/1966 | (GB) . |
| 1 153 196 | 5/1969 | (GB) . |
| 9-110659 | 4/1997 | (JP) . |

| WO 94/00100 | 1/1994 | (WO) . |
|---|---|---|
| WO 94/08969 | 4/1994 | (WO) . |
| WO 94/08970 | 4/1994 | (WO) . |
| WO 95/01772 | 1/1995 | (WO) . |
| WO 95/15144 | 6/1995 | (WO) . |
| WO 94/15765 | 5/1996 | (WO) . |
| WO 97/24105 | 7/1997 | (WO) . |
| 97/24106 | * 7/1997 | (WO) . |
| 97/24107 | * 7/1997 | (WO) . |
| 98/22078 | * 5/1998 | (WO) . |

OTHER PUBLICATIONS

Vishnu J. Ram et al., "Synthesis of bioisosteric pyrazolo[1, 5–a]pyrimidines as leishmanicides", Indian Journal of Chemistry, vol. 34B, Jun. 1995, pp. 514–520.

Nadia S. Ibraham et al., "Studies on 3,5–Diaminopyrazoles: Synthesis of New Polyfunctionally Substituted Pyrazoloazines and Pyrazoloazoles", Archiv der Pharmazie, vol. 320, No. 3, Mar. 1987, pp. 240–246.

Robert H. Springer et al., "Synthesis and Enzymic Activity of 6–Carbethoxy– and 6–Ethoxy–3,7–disubstituted–pyrazolo[1,5–α]pyrimidines and Related Derivatives as Adenosine Cyclic 3', 5'–Phosphate Phosphodiesterase Inhibitors", Journal of Medicinal Chemistry, vol. 25, No. 3, 1982, pp. 235–242.

Thomas Novinson et al., "Synthesis and Antifungal Properties of Certain 7–Alkylaminopyrazolo[1,5–a]pyrimidines", Journal of Medicinal Chemistry, vol. 20, No. 2, 1977, pp. 296–299.

Alexander McKillop et al., "Reaction of Hydrazine with β–Aminocrotononitrile: Synthesis of 2,7–dimethyl–5–aminopyrazolo[1,5–a]pyrimidine", Heterocycles, vol. 6, Nos. 9, 10, 1977, pp. 1355–1360.

Koji Saito et al., "The Reaction of Ethyl Ethoxymethylenecyanoacetate with Its Hydrazino Derivatives", Bulletin of the Chemical Society of Japan, vol. 47, No. 2, 1974, pp. 476–480.

Ermitas Alcade et al., "Etude de la réaction du β–aminocrotonitrile et du α–formyl phénylacétonitile avec l'hydrazine: synthèse d'amino–7 pyrazolo[1,5–a]pyrimidines", Journal of Heterocyclic Chemistry, vol. 11, No. 3, Jun. 1974, pp. 423–429.

English language Derwent Abstract of DE 23 59 399, Jun. 1975.

English language Derwent Abstract of DE 38 43 892, Jun. 1990.

(List continued on next page.)

*Primary Examiner*—Caroline D. Liott
(74) *Attorney, Agent, or Firm*—Finnegan, Henderson, Farabow, Garrett & Dunner, L.L.P.

(57) ABSTRACT

The invention relates to a ready-to-use composition for the oxidation dyeing of keratin fibers, and in particular human keratin fibers such as the hair, comprising, in a medium which is suitable for dyeing, at least one oxidation base, at least one cationic direct dye and at least one enzyme of 2-electron oxidoreductase type in the presence of at least one donor for the said enzyme, and to the dyeing process using this composition.

52 Claims, No Drawings

OTHER PUBLICATIONS

English language Derwent Abstract of DE 41 33 957, Apr. 1993.

English language Derwent Abstract of DE 195 43 988, May 1997.

English language Derwent Abstract of DE 195 47 991, Jun. 1997.

English language Derwent Abstract of EP 0 714 954, Jun. 1996.

English language Derwent Abstract of EP 0 766 958, Apr. 1997.

English language Derwent Abstract of EP 0 795 313, Sep. 1997.

English language Derwent Abstract of FR 2 586 913, Mar. 1987.

English language Derwent Abstract of FR 2 733 749, Nov. 1996.

English language Derwent Abstract of JP 2019576, Jan. 1990.

English language Derwent Abstract of JP 9–110659, Apr. 1997.

* cited by examiner

OXIDATION DYEING COMPOSITION FOR KERATIN FIBRES AND DYEING METHOD USING SAID COMPOSITION

The invention relates to a composition for the oxidation dyeing of keratin fibres, and in particular human keratin fibres such as the hair, comprising, in a medium which is suitable for dyeing, at least one oxidation base, at least one cationic direct dye and at least one enzyme of 2-electron oxidoreductase type in the presence of at least one donor for the said enzyme, and to the dyeing process using this composition.

It is known to dye keratin fibres, and in particular human hair, with dye compositions containing oxidation dye precursors, in particular ortho- or para-phenylenediamines, ortho- or para-aminophenols and heterocyclic bases, which are generally referred to as oxidation bases. Oxidation dye precursors, or oxidation bases, are colourless or weakly coloured compounds which, when combined with oxidizing products, can give rise to coloured compounds and dyes by a process of oxidative condensation.

It is also known that the shades obtained with these oxidation bases can be varied by combining them with couplers or colour modifiers, the latter being chosen in particular from aromatic meta-diamines, meta-aminophenols, meta-diphenols and certain heterocyclic compounds.

The variety of molecules used as oxidation bases and couplers allows a wide range of colours to be obtained.

It is also known that, in order to further vary the shades obtained and to give them glints, direct dyes, i.e. coloured substances which provide a coloration in the absence of an oxidizing agent, can be used in combination with the oxidation dye precursors and couplers.

The vast majority of these direct dyes belong to the family of compounds of the nitrobenzene series and have the drawback, when they are incorporated into dye compositions, of leading to colorations with insufficient staying power, in particular with regard to shampooing.

The so-called "permanent" coloration obtained by means of these oxidation dyes must moreover satisfy a certain number of requirements. Thus, it must have no toxicological drawbacks, it must be able to give shades of the desired intensity and it must be able to withstand external agents (light, bad weather, washing, permanent-waving, perspiration, rubbing).

The dyes must also be able to cover white hair and, lastly, they must be as unselective as possible, i.e. they must give the smallest possible colour differences along the same length of keratin fibre, which may in fact be differently sensitized (i.e. damaged) between its tip and its root.

The oxidation dyeing of keratin fibres is generally carried out in alkaline medium, in the presence of hydrogen peroxide. However, the use of alkaline media in the presence of hydrogen peroxide have the drawback of causing appreciable degradation of the fibres, as well as considerable bleaching of the keratin fibres, which is not always desirable.

The oxidation dyeing of keratin fibres can also be carried out using oxidizing systems other than hydrogen peroxide, such as enzymatic systems. Thus, it has already been proposed to dye keratin fibres, in particular in patent application EP-A-0,310,675, with compositions comprising an oxidation base and optionally a coupler, in combination with enzymes such as pyranose oxidase, glucose oxidase or uricase, in the presence of a donor for the said enzymes. Although being used under conditions which do not result in a degradation of the keratin fibres which is comparable to that caused by the dyes used in the presence of hydrogen peroxide, these dyeing processes nevertheless lead to colorations which are not entirely satisfactory, in particular as regards their intensity, chromaticity and resistance to the various attacking factors to which the hair may be subjected.

The Applicant has now discovered that it is possible to obtain new dyes, which are capable of leading to intense and chromatic colorations, without giving rise to any significant degradation of the keratin fibres, and which are relatively unselective and show good resistance to the various attacking factors to which the hair may be subjected, by combining at least one oxidation base, at least one cationic direct dye and at least one enzyme of 2-electron oxidoreductase type in the presence of at least one donor for the said enzyme.

This discovery forms the basis of the present invention.

A first subject of the invention is thus a ready-to-use composition for the oxidation dyeing of keratin fibres, and in particular human keratin fibres such as the hair, characterized in that it comprises, in a medium which is suitable for dyeing:
- at least one oxidation base,
- at least one cationic direct dye,
- at least one enzyme of 2-electron oxidoreductase type, and
- at least one donor for the said enzyme.

The ready-to-use dye composition in accordance with the invention leads to intense, chromatic, relatively unselective colorations with excellent properties of resistance both to atmospheric agents such as light and bad weather and to perspiration and the various treatments to which the hair may be subjected (washing, permanent-waving).

A subject of the invention is also a process for the oxidation dyeing of keratin fibres using this ready-to-use dye composition.

The 2-electron oxidoreductase(s) used in the ready-to-use dye composition in accordance with the invention can be chosen in particular from pyranose oxidases, glucose oxidases, glycerol oxidases, lactate oxidases, pyruvate oxidases and uricases.

According to the invention, the 2-electron oxidoreductase is preferably chosen from uricases of animal, microbiological or biotechnological origin.

By way of example, mention may be made of uricase extracted from boar liver, uricase from *Arthrobacter globiformis*, as well as uricase from *Aspergillus flavus*.

The 2-electron oxidoreductase(s) can be used in pure crystalline form or in a form diluted in a diluent which is inert with respect to the said 2-electron oxidoreductase.

The 2-electron oxidoreductase(s) in accordance with the invention preferably represent(s) from 0.01 to 20% by weight approximately relative to the total weight of the ready-to-use dye composition, and even more preferably from 0.1 to 5% by weight approximately relative to this weight.

According to the invention, the term donor is understood to refer to the various substrates involved in the functioning of the said 2-electron oxidoreductase(s).

The nature of the donor (or substrate) for the said enzyme varies depending on the nature of the 2-electron oxidoreductase used. For example, as donors for the pyranose oxidases, mention may be made of D-glucose, L-sorbose and D-xylose; as a donor for the glucose oxidases, mention may be made of D-glucose; as donors for the glycerol oxidases, mention may be made of glycerol and dihydroxyacetone; as donors for the lactate oxidases, mention may be made of lactic acid and its salts; as donors for the pyruvate oxidases, mention may be made of pyruvic acid and its salts; and lastly, as donors for the uricases, mention may be made of uric acid and its salts.

The donor(s) (or substrate(s)) used in accordance with the invention preferably represent(s) from 0.01 to 20% by weight approximately relative to the total weight of the ready-to-use dye composition in accordance with the invention, and even more preferably from 0.1 to 5% by approximately relative to this weight.

The nature of the oxidation base(s) used in the ready-to-use dye composition is not a critical factor. They can be chosen, in particular, from para-phenylenediamines, double bases, para-aminophenols, ortho-aminophenols and heterocyclic oxidation bases.

Among the para-phenylenediamines which can be used as oxidation bases in the dye compositions in accordance with the invention, mention may be made in particular of the compounds of formula (I) below, and the addition salts thereof with an acid:

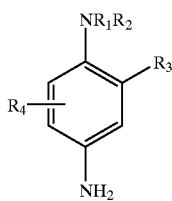

(I)

in which:
R$_1$ represents a hydrogen atom, a C$_1$–C$_4$ alkyl radical, a C$_1$–C$_4$ monohydroxyalkyl radical, a C$_2$–C$_4$ polyhydroxyalkyl radical, a (C$_1$–C$_4$)alkoxy(C$_1$–C$_4$)alkyl radical, a C$_1$–C$_4$ alkyl radical substituted with a nitrogenous group, a phenyl radical or a 4'-aminophenyl radical;

R$_2$ represents a hydrogen atom, a C$_1$–C$_4$ alkyl radical, a C$_1$–C$_4$ monohydroxyalkyl radical, a C$_2$–C$_4$ polyhydroxyalkyl radical, a (C$_1$–C$_4$)alkoxy(C$_1$–C$_4$)alkyl radical or a C$_1$–C$_4$ alkyl radical substituted with a nitrogenous group;

R$_3$ represents a hydrogen atom, a halogen atom such as a chlorine, bromine, iodine or fluorine atom, a C$_1$–C$_4$ alkyl radical, a C$_1$–C$_4$ monohydroxyalkyl radical, a C$_1$–C$_4$ hydroxyalkoxy radical, an acetylamino(C$_1$–C$_4$) alkoxy radical, a C$_1$–C$_4$ mesylaminoalkoxy radical or a carbamoylamino(C$_1$–C$_4$)alkoxy radical, R$_4$ represents a hydrogen or halogen atom or a C$_1$–C$_4$ alkyl radical.

Among the nitrogenous groups of formula (I) above, mention may be made in particular of amino, mono(C$_1$–C$_4$)alkylamino, di(C$_1$–C$_4$)alkylamino, tri(C$_1$–C$_4$)alkylamino, monohydroxy(C$_1$–C$_4$)alkylamino, imidazolinium and ammonium radicals.

Among the para-phenylenediamines of formula (I) above, mention may be made more particularly of para-phenylenediamine, para-toluylenediamine, 2-chloro-para-phenylenediamine, 2,3-dimethyl-para-phenylene-diamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine and N-(β-methoxyethyl)-para-phenylenediamine, and the addition salts thereof with an acid.

Among the para-phenylenediamines of formula (I) above, para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine and the addition salts thereof with an acid are most particularly preferred.

According to the invention, the term double bases is understood to refer to the compounds containing at least two aromatic rings bearing amino and/or hydroxyl groups.

Among the double bases which can be used as oxidation bases in the dye compositions in accordance with the invention, mention may be made in particular of the compounds corresponding to formula (II) below, and the addition salts thereof with an acid:

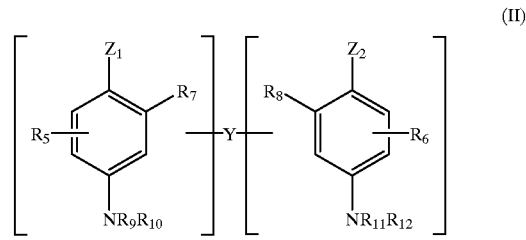

(II)

in which:
Z$_1$ and Z$_2$, which may be identical or different, represent a hydroxyl or —NH$_2$ radical which may be substituted with a C$_1$–C$_4$ alkyl radical or with a linker arm Y;

the linker arm Y represents a linear or branched alkylene chain containing from 1 to 14 carbon atoms, which may be interrupted by or terminated with one or more nitrogenous groups and/or one or more hetero atoms such as oxygen, sulphur or nitrogen atoms, and optionally substituted with one or more hydroxyl or C$_1$–C$_6$ alkoxy radicals;

R$_5$ and R$_6$ represent a hydrogen or halogen atom, a C$_1$–C$_4$ alkyl radical, a C$_1$–C$_4$ monohydroxyalkyl radical, a C$_2$–C$_4$ polyhydroxyalkyl radical, a C$_1$–C$_4$ aminoalkyl radical or a linker arm Y;

R$_7$, R$_8$, R$_9$, R$_{10}$, R$_{11}$ and R$_{12}$, which may be identical or different, represent a hydrogen atom, a linker arm Y or a C$_1$–C$_4$ alkyl radical;

it being understood that the compounds of formula (II) contain only one linker arm Y per molecule.

Among the nitrogenous groups of formula (II) above, mention may be made in particular of amino, mono (C$_1$–C$_4$) alkylamino, di(C$_1$–C$_4$)alkylamino, tri(C$_1$–C$_4$)alkylamino, monohydroxy(C$_1$–C$_4$)alkylamino, imidazolinium and ammonium radicals.

Among the double bases of formula (II) above, mention may be made more particularly of N,N'-bis-(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy) 3,5-dioxaoctane, and the addition salts thereof with an acid.

Among these double bases of formula (II), N,N'-bis(β-hydroxyethyl)-N,N'-bis(4'-aminophenyl)1,3-diaminopropanol and 1,8-bis(2,5-diaminophenoxy)3,5-dioxaoctane, or one of the addition salts thereof with an acid, are particularly preferred.

Among the para-aminophenols which can be used as oxidation bases in the dye compositions in accordance with the invention, mention may be made in particular of the compounds corresponding to formula (III) below, and the addition salts thereof with an acid:

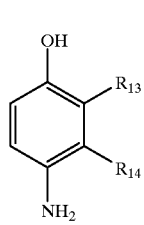

(III)

in which:
R$_{13}$ represents a hydrogen or halogen atom or a C$_1$—C$_4$ alkyl, C$_1$–C$_4$ monohydroxyalkyl, (C$_1$–C$_4$)alkoxy (C$_1$–C$_4$)alkyl, C$_1$–C$_4$ aminoalkyl or hydroxy(C$_1$–C$_4$) alkylamino(C$_1$–C$_4$)alkyl radical,
R$_{14}$ represents a hydrogen or halogen atom or a C$_1$–C$_4$ alkyl, C$_1$–C$_4$ monohydroxyalkyl, C$_2$–C$_4$ polyhydroxyalkyl, C$_1$–C$_4$ aminoalkyl, C$_1$–C$_4$ cyanoalkyl or (C$_1$–C$_4$)alkoxy(C$_1$–C$_4$)alkyl radical,
it being understood that at least one of the radicals R$_{13}$ or R$_{14}$ represents a hydrogen atom.

Among the para-aminophenols of formula (III) above, mention may be made more particularly of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols which can be used as oxidation bases in the dye compositions in accordance with the invention, mention may be made more particularly of 2-aminophenol, 2-amino-5-methylphenol, 2-amino-6-methylphenol and 5-acetamido-2-aminophenol, and the addition salts thereof with an acid.

Among the heterocyclic bases which can be used as oxidation bases in the dye compositions in accordance with the invention, mention may be made more particularly of pyridine derivatives, pyrimidine derivatives, pyrazole derivatives and pyrazolopyrimidine derivatives, and the addition salts thereof with an acid.

Among the pyridine derivatives, mention may be made more particularly of the compounds described, for example, in patents GB 1,026,978 and GB 1,153,196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Among the pyrimidine derivatives, mention may be made more particularly of the compounds described, for example, in German patent DE 2,359,399 or Japanese patents JP 88-169,571 and JP 91-10659 or patent applications WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and the addition salts thereof with an acid.

Among the pyrazole derivatives, mention may be made more particularly of the compounds described in patents DE 3,843,892, DE 4,133,957 and patent applications WO 94/08969, WO 94/08970, FR-A-2,733,749 and DE 195 43 988, such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl) amino-1-methylpyrazole, and the addition salts thereof with an acid.

Among the pyrazolopyrimidine derivatives, mention may be made more particularly of the pyrazolo[1,5-a]pyrimidines of formula (IV) below, and the addition salts thereof with an acid or with a base and the tautomeric forms thereof, when a tautomeric equilibrium exists:

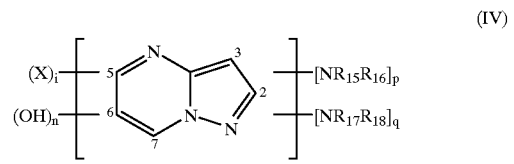

(IV)

in which:
R$_{15}$, R$_{16}$, R$_{17}$ and R$_{18}$, which may be identical or different, denote a hydrogen atom, a C$_1$–C$_4$ alkyl radical, an aryl radial, a C$_1$–C$_4$hydroxyalkyl radical, a C$_2$–C$_4$ polyhydroxyalkyl radical, a (C$_1$–C$_4$)alkoxy(C$_1$–C$_4$)alkyl radical, a C$_1$–C$_4$ aminoalkyl radical (it being possible for the amine to be protected with an acetyl, ureido or sulphonyl radical), a (C$_1$–C$_4$)alkylamino(C$_1$–C$_4$)alkyl radical, a di [(C$_1$–C$_4$)alkyl]amino(C$_1$–C$_4$)alkyl radical (it being possible for the dialkyl radicals to form a 5- or 6-membered carbon-based ring or a heterocycle), a hydroxy(C$_1$–C$_4$)alkyl- or di[hydroxy(C$_1$–C$_4$)alkyl] amino (C$_1$–C$_4$) alkyl radical;
the radicals X, which may be identical or different, denote a hydrogen atom, a C$_1$–C$_4$ alkyl radical, an aryl radical, a C$_1$–C$_4$ hydroxyalkyl radical, a C$_2$–C$_4$ polyhydroxyalkyl radical, a C$_1$–C$_4$ aminoalkyl radical, a (C$_1$–C$_4$)

alkylamino($C_1$–$C_4$)alkyl radical, a di[($C_1$–$C_4$)alkyl] amino($C_1$–$C_4$)alkyl radical (it being possible for the dialkyls to form a 5- or 6-membered carbon-based ring or a heterocycle), a hydroxy($C_1$–$C_4$)alkyl- or di-[hydroxy($C_1$–$C_4$)alkyl]amino($C_1$–$C_4$)alkyl radical, an amino radical, a ($C_1$–$C_4$)alkyl- or di[($C_1$–$C_4$)alkyl] amino radical; a halogen atom, a carboxylic acid group, a sulphonic acid group;

i is equal to 0, 1, 2 or 3;
p is equal to 0 or 1;
q is equal to 0 or 1;
n is equal to 0 or 1;

with the proviso that:
the sum p+q is other than 0;
when p+q is equal to 2, then n is equal to 0 and the groups $NR_{15}R_{16}$ and $NR_{17}R_{18}$ occupy the (2,3); (5,6); (6,7); (3,5) or (3,7) positions;
when p+q is equal to 1, then n is equal to 1 and the group $NR_{15}R_{16}$ (or $NR_{17}R_{18}$) and the OH group occupy the (2,3); (5,6); (6,7); (3,5) or (3,7) positions.

When the pyrazolo[1,5-a]pyrimidines of formula (IV) above are such that they contain a hydroxyl group on one of the positions 2, 5 or 7 α to a nitrogen atom, a tautomeric equilibrium exists represented, for example, by the following scheme:

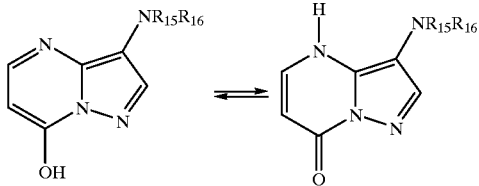

Among the pyrazolo[1,5-a]pyrimidines of formula (IV) above, mention may be made in particular of:
pyrazolo[1,5-a]pyrimidine-3,7-diamine;
2,5-dimethylpyrazolo[1,5-a]pyrimidine-3,7-diamine;
pyrazolo[1,5-a]pyrimidine-3,5-diamine;
2,7-dimethylpyrazolo[1,5-a]pyrimidine-3,5-diamine;
3-aminopyrazolo[1,5-a]pyrimidin-7-ol;
3-aminopyrazolo[1,5-a]pyrimidin-5-ol;
2-(3-aminopyrazolo[1,5-a]pyrimidin-7-ylamino)ethanol;
2-(7-aminopyrazolo[1,5-a]pyrimidin-3-ylamino)ethanol;
2-[(3-aminopyrazolo[1,5-a]pyrimidin-7-yl)-(2-hydroxyethyl)amino]ethanol;
2-[(7-aminopyrazolo[1,5-a]pyrimidin-3-yl)-(2-hydroxyethyl)amino]ethanol;
5,6-dimethylpyrazolo[1,5-a]pyrimidine-3,7-diamine;
2,6-dimethylpyrazolo[1,5-a]pyrimidine-3,7-diamine;
2,5,N7,N7-tetramethylpyrazolo[1,5-a]pyrimidine-3,7-diamine;
and the addition salts thereof and the tautomeric forms thereof, when a tautomeric equilibrium exists.

The pyrazolo[1,5-a]pyrimidines of formula (IV) above can be prepared by cyclization starting with an aminopyrazole, according to the syntheses described in the following references:
EP 628559 Beiersdorf-Lilly.
R. Vishdu, H. Navedul, Indian J. Chem., 34b (6), 514, 1995.
N. S. Ibrahim, K. U. Sadek, F. A. Abdel-Al, Arch. Pharm., 320, 240, 1987.
R. H. Springer, M. B. Scholten, D. E. O'Brien, T. Novinson, J. P. Miller, R. K. Robins, J. Med. Chem., 25, 235, 1982.
T. Novinson, R. K. Robins, T. R. Matthews, J. Med. Chem., 20, 296, 1977.
U.S. Pat. No. 3,907,799 ICN Pharmaceuticals.

The pyrazolo[1,5-a]pyrimidines of formula (IV) above can also be prepared by cyclization starting from hydrazine, according to the syntheses described in the following references:
A. McKillop and R. J. Kobilecki, Heterocycles, 6(9), 1355, 1977.
E. Alcade, J. De Mendoza, J. M. Marcia-Marquina, C. Almera, J. Elguero, J. Heterocyclic Chem., 11(3), 423, 1974.
K. Saito, I. Hori, M. Higarashi, H. Midorikawa, Bull. Chem. Soc. Japan, 47(2), 476, 1974.

The oxidation base(s) preferably represent(s) from 0.0005 to 12% by weight approximately relative to the total weight of the dye composition in accordance with the invention, and even more preferably from 0.005 to 6% by weight approximately relative to this weight.

The cationic direct dye(s) which can be used in the ready-to-use dye composition in accordance with the invention is (are) preferably chosen from cationic aminoanthraquinone dyes, cationic monoazo or diazo dyes and cationic naphthoquinone dyes.

By way of example, mention may be made in particular of [8-[(p-aminophenyl)azo]-7-hydroxy-2-naphthyl] trimethylammonium chloride (also known as Basic Brown 16 or Arianor Mahogany 306002 in the Color Index), 3-[(4-amino-6-bromo-5,8-dihydro-1-hydroxy-8-imino-5-oxo-2-naphthalenyl)amino]-N,N,N-trimethylbenzenaminium chloride (also known as Basic Blue 99 or Arianor Steel Blue 306004 in the Color Index), 7-hydroxy-8-[(2-methoxyphenyl)azo]-N,N,N-trimethyl-2-naphthalenaminium chloride (also known as Basic Red 76 or Arianor Madder Red in the Color Index), [8-[(4-amino-2-nitrophenyl)azo]-7-hydroxy-2-naphthyl] trimethylammonium chloride (also known as Basic Brown 17 or Arianor Sienna Brown 306001 in the Color Index) and 3-[(4,5-dihydro-3-methyl-5-oxo-1-phenyl-1H-pyrazol-4-yl) azo]-N,N,N-trimethylbenzenaminium chloride (also known as Basic Yellow 57 or Arianor Straw Yellow 306005 in the Color Index).

The cationic direct dye(s) can also be chosen from:
a) the compounds of formula (V) below:

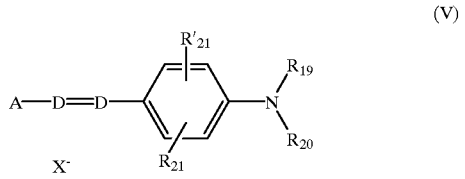

in which:

D represents a nitrogen atom or a —CH group,
$R_{19}$ and $R_{20}$, which may be identical or different, represent a hydrogen atom; a $C_1$–$C_4$ alkyl radical which can be substituted with a —CN, —OH or —$NH_2$ radical or form, with a carbon atom of the benzene ring, an optionally oxygenated or nitrogenous heterocycle, which can be substituted with one or more $C_1$–$C_4$ alkyl radicals; a 4'-aminophenyl radical,
$R_{21}$ and $R'_{21}$, which may be identical or different, represent a hydrogen atom, a halogen atom chosen from chlorine, bromine, iodine and fluorine, or a cyano, $C_1$–$C_4$ alkoxy or acetyloxy radical,
$X^-$ represents an anion preferably chosen from chloride, methyl sulphate and acetate, A represents a group chosen from structures A1 to A19 below:
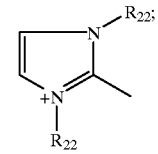 A₁
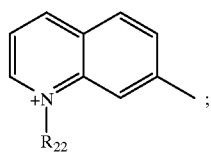 A₂
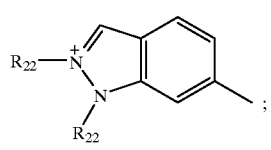 A₃
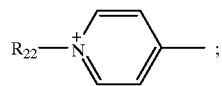 A₄
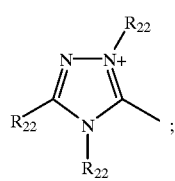 A₅
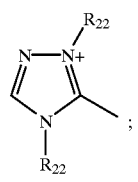 A₆
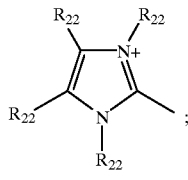 A₇
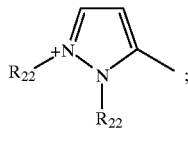 A₈
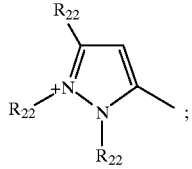 A₉
-continued
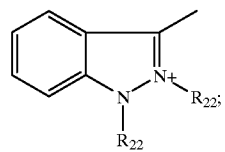 A₁₀
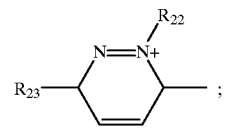 A₁₁
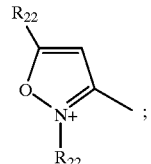 A₁₂
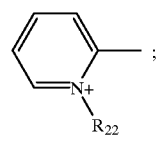 A₁₃
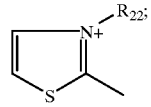 A₁₄
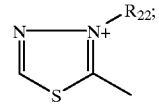 A₁₅
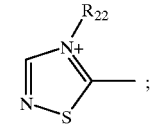 A₁₆
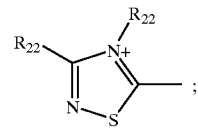 A₁₇
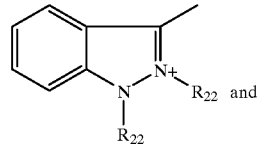 A₁₈ and
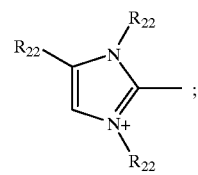 A₁₉ in which $R_{22}$ represents a $C_1$–$C_4$ alkyl radical which can be substituted with a hydroxyl radical and $R_{23}$ represents a $C_1$–$C_4$ alkoxy radical;

b) the compounds of formula (VI) below:

(IV)

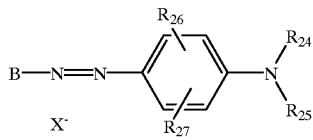

in which:

$R_{24}$ represents a hydrogen atom or a $C_1$–$C_4$ alkyl radical, $R_{25}$ represents a hydrogen atom, an alkyl radical which can be substituted with a —CN radical or with an amino group, a 4'-aminophenyl radical or forms, with $R_{24}$, an optionally oxygenated and/or nitrogenous heterocycle which can be substituted with a $C_1$–$C_4$ alkyl radical, $R_{26}$ and $R_{27}$, which may be identical or different, represent a hydrogen atom, a halogen atom such as bromine, chlorine, iodine or fluorine, a $C_1$–$C_4$ alkyl or $C_1$–$C_4$ alkoxy radical or a —CN radical, $X^-$ represents an anion preferably chosen from chloride, methyl sulphate and acetate, B represents a group chosen from structures B1 to B6 below:

B1

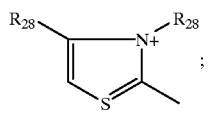

B2

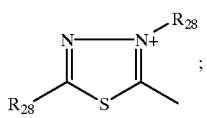

B3

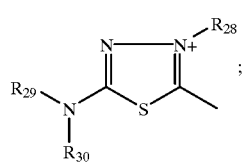

B4

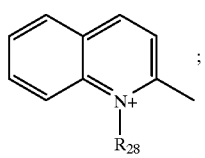

B5

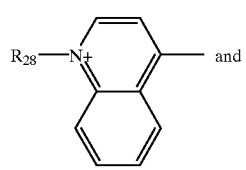 and

B6

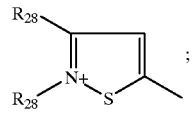

in which $R_{28}$ represents a $C_1$–$C_4$ alkyl radical, $R_{29}$ and $R_{30}$, which may be identical or different, represent a hydrogen atom or a $C_1$–$C_4$ alkyl radical; c) the compounds of formulae (VII) and (VII') below:

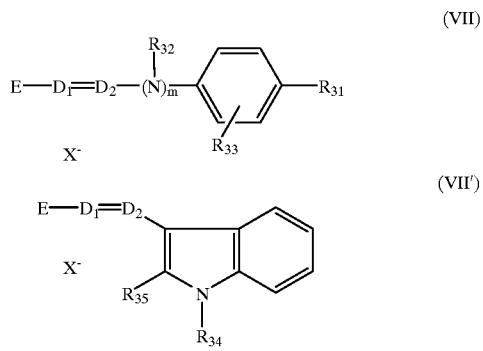

in which:

$R_{31}$ represents a hydrogen atom, a $C_1$–$C_4$ alkoxy radical, a halogen atom such as bromine, chlorine, iodine or fluorine, or an amino radical, $R_{32}$ represents a hydrogen atom, a $C_1$–$C_4$ alkyl radical or forms, with a carbon atom of the benzene ring, a heterocycle which is optionally oxygenated and/or substituted with one or more $C_1$–$C_4$ alkyl groups, $R_{33}$ represents a hydrogen atom or a halogen atom such as bromine, chlorine, iodine or fluorine, $R_{34}$ and $R_{35}$, which may be identical or different, represent a hydrogen atom or a $C_1$–$C_4$ alkyl radical, $D_1$ and $D_2$, which may be identical or different, represent a nitrogen atom or a —CH group, m=0 or 1, it being understood that when $R_{31}$ represents an unsubstituted amino group, then $D_1$ and $D_2$ simultaneously represent a —CH group and m=0, $X^-$ represents an anion preferably chosen from chloride, methyl sulphate and acetate, E represents a group chosen from structures E1 to E8 below:

E1

E2

-continued

E3 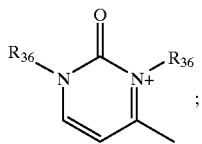

E4 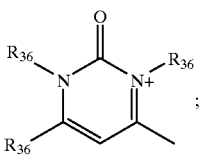

E5 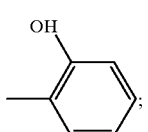

E6 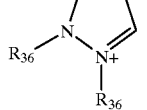

E7 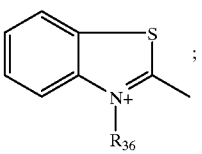

E8 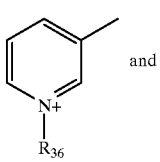

in which $R_{36}$ represents a $C_1$–$C_4$ alkyl radical; when m=0 and when $D_1$ represents a nitrogen atom, then E can also denote a group of structure E9 below:

E9 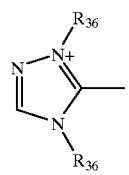

in which $R_{36}$ represents a $C_1$–$C_4$ alkyl radical.

The cationic direct dyes of formulae (V), (VI), (VII) and (VII') which can be used in the ready-to-use dye composition in accordance with the invention are known compounds and are described, for example, in patent applications WO 95/01772, WO 95/15144 and EP-A-0,714,954.

Among the cationic direct dyes of formula (V) which can be used in the ready-to-use dye compositions in accordance with the invention, mention may be made more particularly of the compounds corresponding to structures (V1) to (V52) below:

(V1) 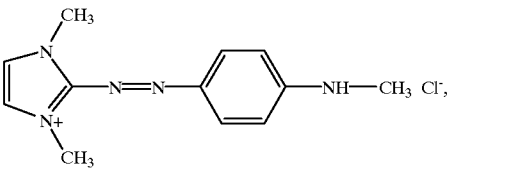

(V2) 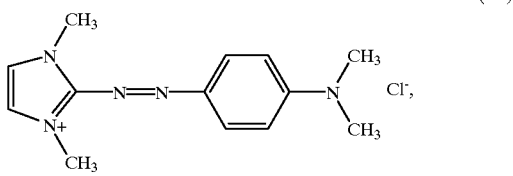

(V3) 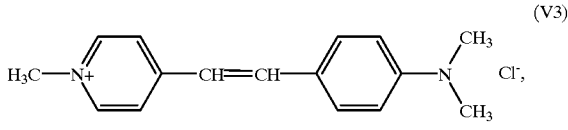

(V4) 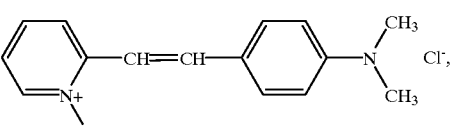

(V5) 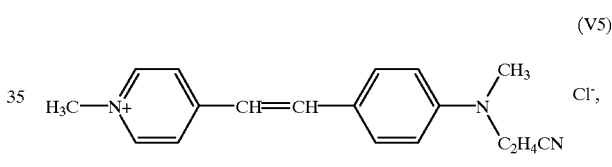

(V6) 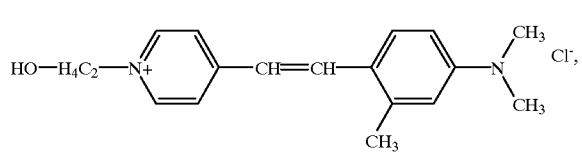

(V7) 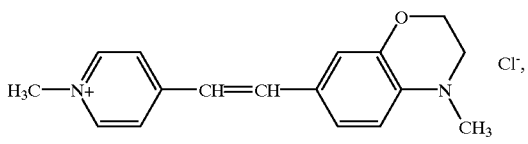

(V8) 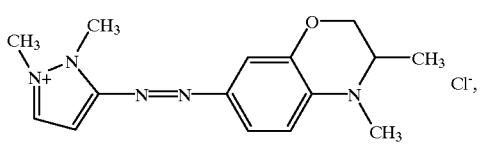

(V9) 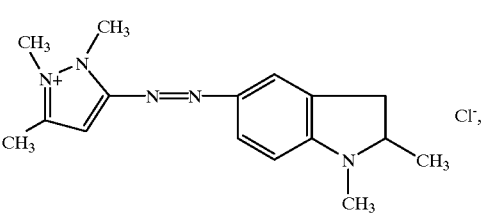

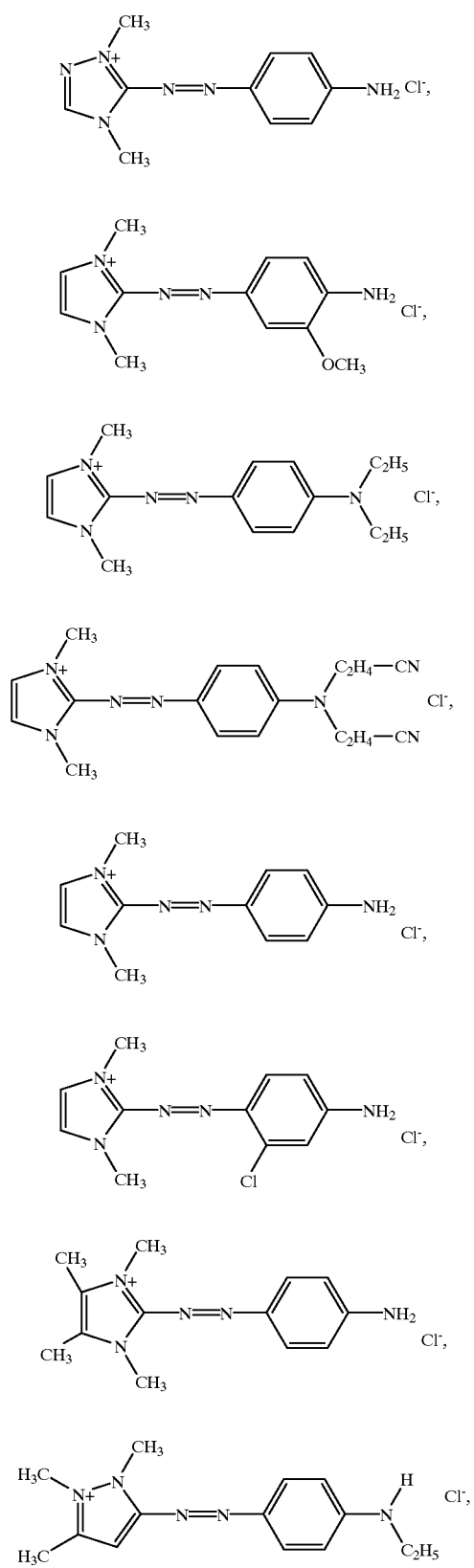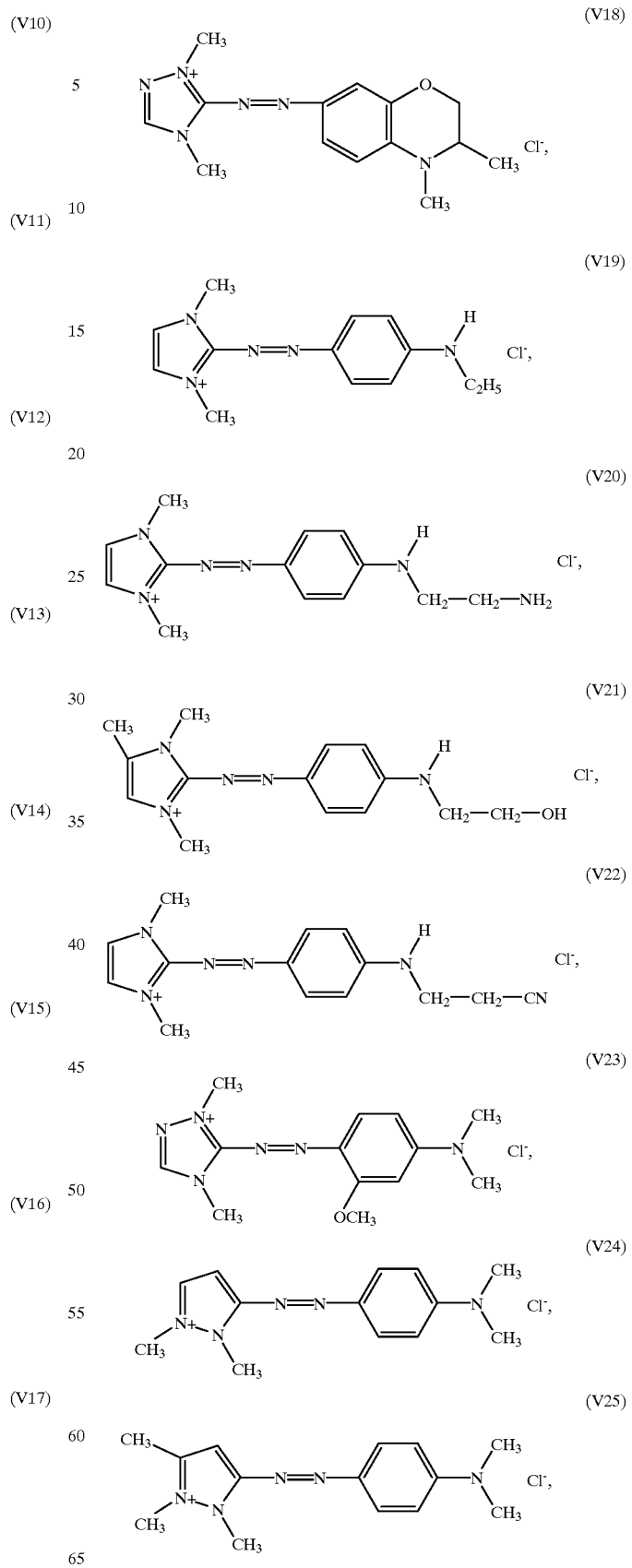

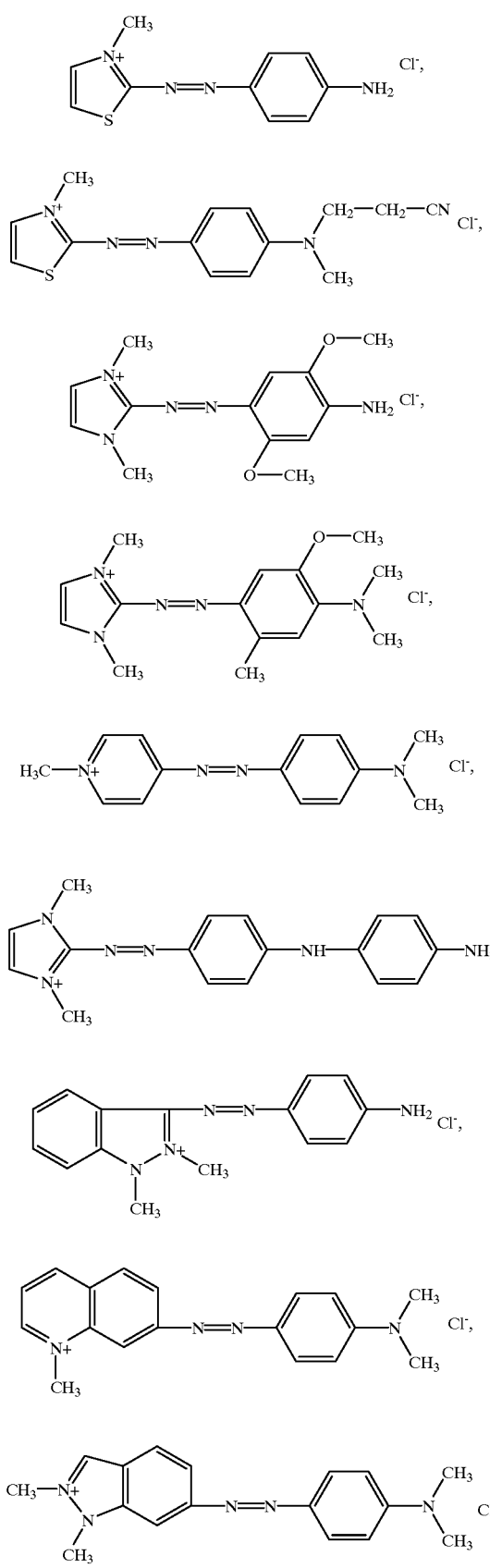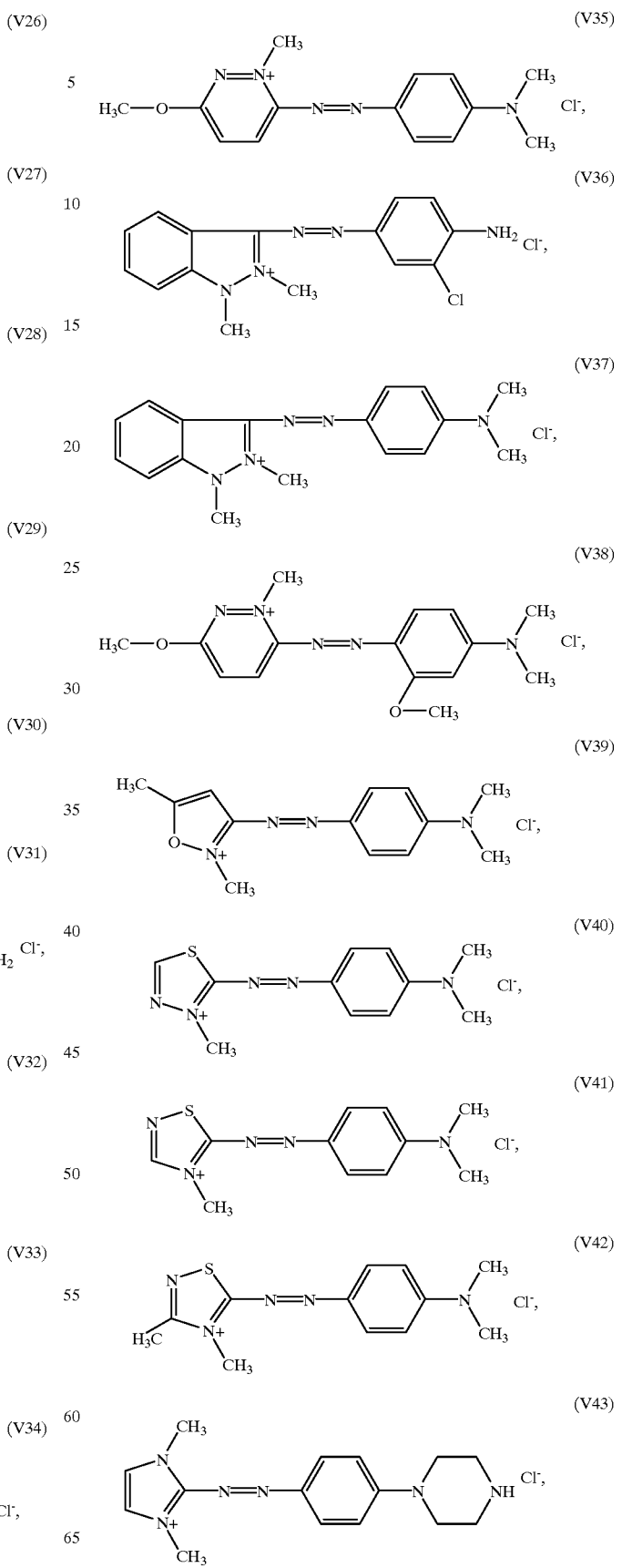

-continued (V44) 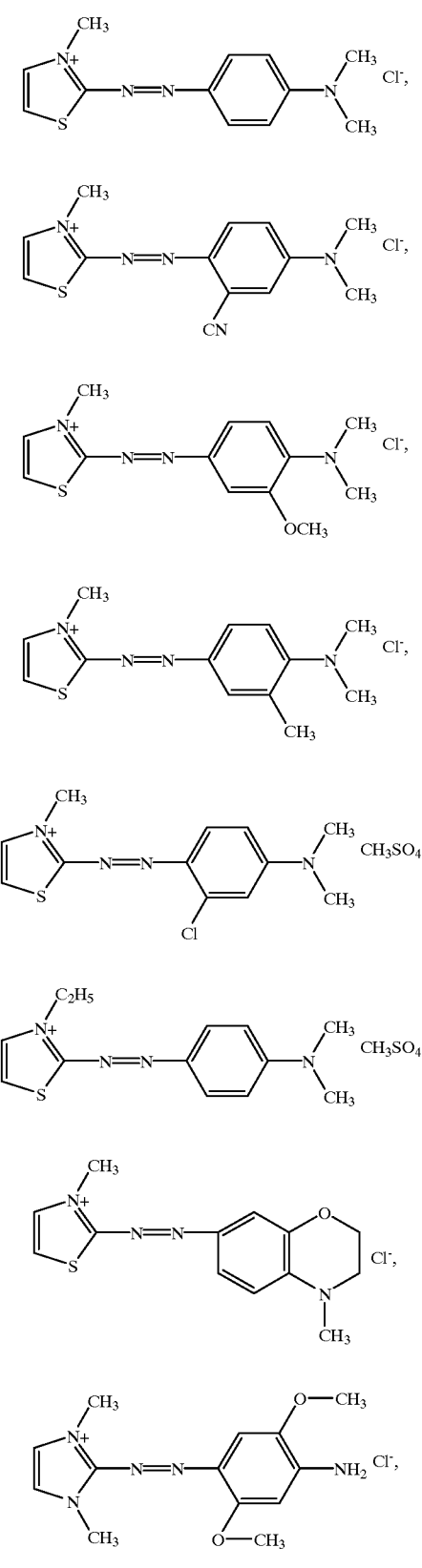

(V45)

(V46)

(V47)

(V48)

(V49)

(V50)

(V51) and

-continued (V52) 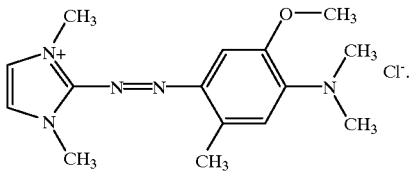

Among the compounds of structures (V1) to (V52) described above, the ones most particularly preferred are the compounds corresponding to structures (V1), (V2), (V4), (V14) and (V31).

Among the cationic direct dyes of formula (VI) which can be used in the ready-to-use dye compositions in accordance with the invention, mention may be made more particularly of the compounds corresponding to structures (VI1) to (VI12) below:

(VI1) 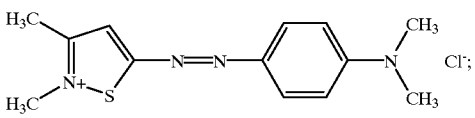

(VI2) 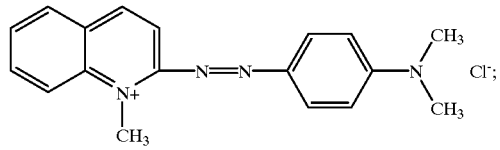

(VI3) 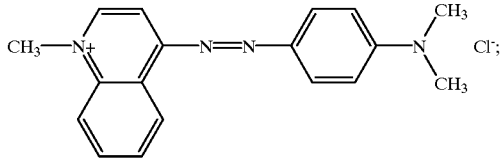

(VI4) 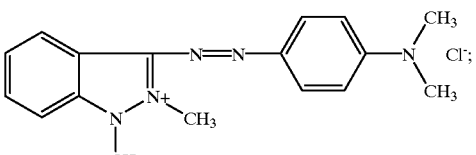

(VI5) 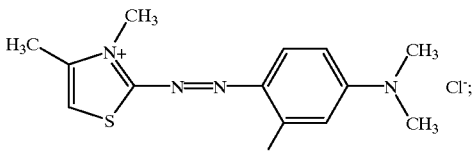

(VI6) 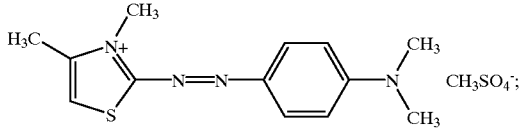

(VI7)
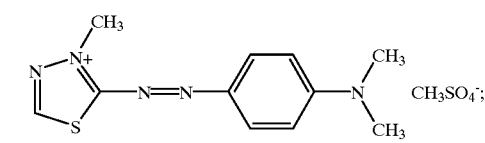
(VI8)
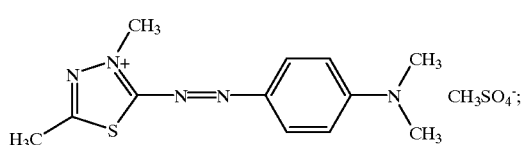
(VI9)
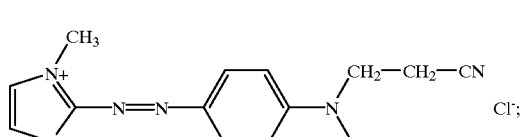
(VI10)
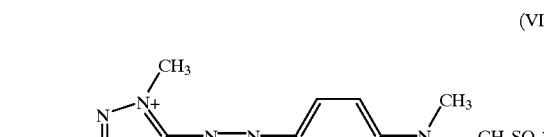
(VI11)
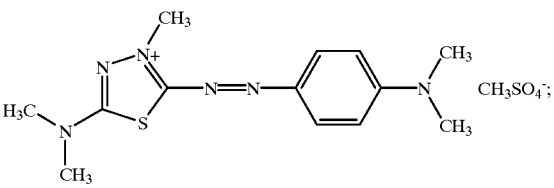
(VI12)
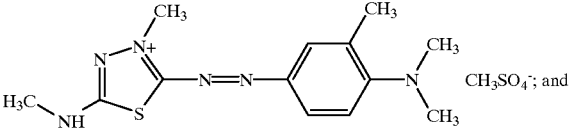
Among the cationic direct dyes of formula (VII) which can be used in the ready-to-use dye compositions in accordance with the invention, mention may be made more particularly of the compounds corresponding to structures (VII1) to (VII18) below:
(VII1)
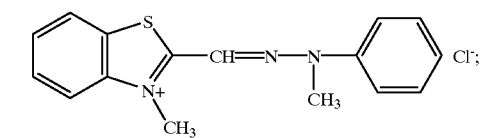
(VII2)
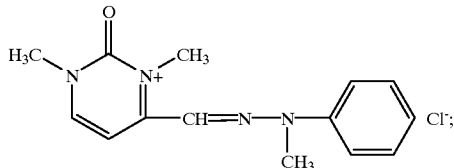
(VII3)
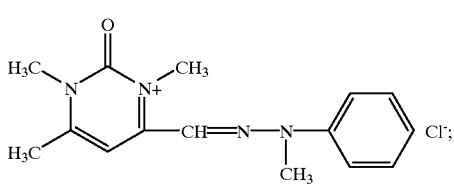
(VII4)
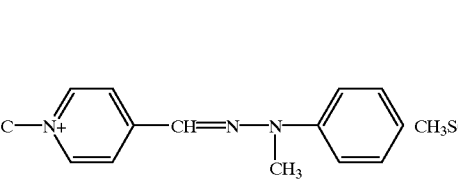
(VII5)
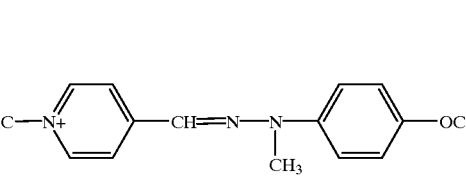
(VII6)
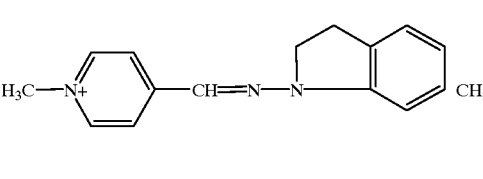
(VII7)
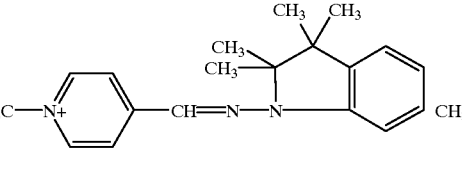
(VII8)
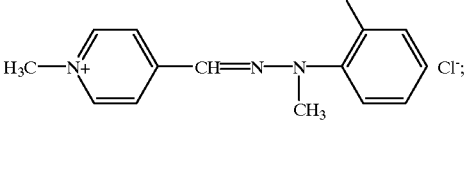
(VII9)
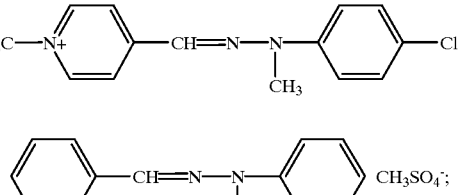
(VII10)

Among the specific compounds of structures (VII1) to (VII18) described above, the ones most particularly preferred are the compounds corresponding to structures (VII4), (VII5) and (VII13).

Among the cationic direct dyes of formula (VII') which can be used in the ready-to-use dye compositions in accordance with the invention, mention may be made more particularly of the compounds corresponding to structures (VII'1) to (VII'3) below:

The cationic direct dye(s) used according to the invention preferably represent(s) from 0.001 to 10% by weight approximately relative to the total weight of the ready-to-use dye composition, and even more preferably from 0.05 to 5% by weight approximately relative to this weight.

The dye composition in accordance with the invention can also contain one or more couplers and/or non-cationic direct dyes, in particular in order to modify the shades or to enrich them with glints.

Among the couplers which can be present in the ready-to-use dye composition in accordance with the invention, mention may be made in particular of meta-phenylenediamines, meta-aminophenols, meta-diphenols and heterocyclic couplers, and the addition salts thereof with an acid.

When they are present, these additional couplers preferably represent from 0.0001 to 10% by weight approximately relative to the total weight of the ready-to-use dye composition, and even more preferably from 0.005 to 5% by weight approximately relative to this weight.

In general, the addition salts with an acid which can be used in the context of the dye compositions of the invention (oxidation bases and couplers) are chosen in particular from the hydrochlorides, hydrobromides, sulphates, tartrates, lactates and acetates.

The medium which is suitable for dyeing (or support) for the ready-to-use dye composition in accordance with the invention generally consists of water or a mixture of water and at least one organic solvent to dissolve the compounds which would not be sufficiently soluble in water. By way of organic solvents, mention may be made, for example, of $C_1$–$C_4$ alkanols, such as ethanol and isopropanol; glycerol; glycols and glycol ethers such as 2-butoxyethanol, propylene glycol, propylene glycol monomethyl ether, diethylene glycol monoethyl ether and monomethyl ether, and aromatic alcohols such as benzyl alcohol or phenoxyethanol, similar products and mixtures thereof.

The solvents can be present in proportions referably of between 1 and 40% by weight approximately relative to the total weight of the dye composition, and even more preferably between 5 and 30% by weight approximately.

The pH of the ready-to-use composition in accordance with the invention is chosen such that the enzymatic activity of the 2-electron oxidoreductase is sufficient. It is generally between 5 and 11 approximately, and preferably between 6.5 and 10 approximately. It can be adjusted to the desired value using acidifying or basifying agents usually used for dyeing keratin fibres.

Among the acidifying agents, mention may be made, by way of example, of inorganic or organic acids such as hydrochloric acid, orthophosphoric acid, sulphuric acid, carboxylic acids such as acetic acid, tartaric acid, citric acid or lactic acid, and sulphonic acids.

Among the basifying agents, mention may be made, by way of example, of aqueous ammonia, alkaline carbonates, alkanolamines such as mono-, di- and triethanolamines, 2-methyl-2-aminopropanol and derivatives thereof, sodium hydroxide, potassium hydroxide and the compounds of formula (VIII) below:

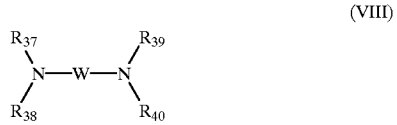

(VIII)

in which W is a propylene residue optionally substituted with a hydroxyl group or a $C_1$–$C_4$ alkyl radical; $R_{37}$, $R_{38}$, $R_{39}$ and $R_{40}$, which may be identical or different, represent a hydrogen atom or a $C_1$–$C_4$ alkyl or $C_1$–$C_4$ hydroxyalkyl radical.

The ready-to-use dye composition in accordance with the invention can also contain various adjuvants used conventionally in compositions for the dyeing of the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, enzymes other than the 2-electron oxidoreductases used in accordance with the invention, such as, for example, peroxidases, penetration agents, sequestering agents, fragrances, buffers, dispersing agents, conditioners such as, for example, silicones which may or may not be volatile or modified, film-forming agents, ceramides, preserving agents and opacifiers.

Needless to say, a person skilled in the art will take care to select this or these optional complementary compound(s) such that the advantageous properties intrinsically associated with the ready-to-use dye composition in accordance with the invention are not, or are not substantially, adversely affected by the addition or additions envisaged.

The ready-to-use dye composition in accordance with the invention can be in various forms, such as in the form of liquids, creams or gels, which may be pressurized, or in any other form which is suitable for dyeing keratin fibres, and in particular human hair. In this case the oxidation dye(s) and the 2-electron oxidoreductase(s) are present in the same ready-to-use composition, and consequently the said composition must be free of gaseous oxygen, so as to avoid any premature oxidation of the oxidation dye(s).

A subject of the invention is also a process for dyeing keratin fibres, and in particular human keratin fibres such as the hair, using the ready-to-use dye composition as defined above.

According to this process, at least one ready-to-use dye composition as defined above is applied to the fibres, for a period which is sufficient to develop the desired coloration, after which the fibres are rinsed, optionally washed with shampoo, rinsed again and dried.

The time required to develop the coloration on the keratin fibres is usually between 3 and 60 minutes and even more precisely between 5 and 40 minutes.

According to one specific embodiment of the invention, the process includes a preliminary step which consists in separately storing, on the one hand, a composition (A) comprising, in a medium which is suitable for dyeing, at least one oxidation base and at least one cationic direct dye, and, on the other hand, a composition (B) comprising, in a medium which is suitable for dyeing, at least one enzyme of 2-electron oxidoreductase type in the presence of at least one donor for the said enzyme, and then in mixing them together at the time of use, after which this mixture is applied to the keratin fibres.

Another subject of the invention is a multi-compartment dyeing device or "kit" or any other multi-compartment packaging system, a first compartment of which comprises composition (A) as defined above and a second compartment of which comprises composition (B) as defined above. These devices can be equipped with means for delivering the desired mixture onto the hair, such as the devices described in patent FR-2,586,913 in the name of the Applicant.

The examples which follow are intended to illustrate the invention without, however, limiting its scope.

EXAMPLES

Dyeing Examples 1 to 3

The ready-to-use dye compositions below were prepared (contents in grams):

| COMPOSITION | 1 | 2 | 3 |
| --- | --- | --- | --- |
| para-Phenylenediamine (oxidation base) | 0.7 | — | 0.36 |
| Red cationic direct dye of structure (V1) | 0.6 | — | — |
| para-Aminophenol (oxidation base) | — | 0.187 | — |
| 5-N-(β-Hydroxyethyl)amino-2-methyl-phenol (coupler) | — | 0.21 | 0.36 |
| Orange cationic direct dye of structure (V4) | — | 0.065 | — |
| Cationic direct dye: Basic Red 76 (Arianor Madder Red) | — | — | 0.12 |
| Uricase from Arthrobacter globiformis, at 20 international units (I.U.)/mg, sold by the company Sigma | 1.5 | 1.5 | 1.5 |
| Uric acid | 1.5 | 1.5 | 1.5 |
| Common dye support (*) | (*) | (*) | (*) |
| Demineralized water qs | 100 g | 100 g | 100 g |

(*): Common dye support:

| | |
| --- | --- |
| Ethanol | 20.0 g |
| Hydroxyethylcellulose sold under the name Natrosol 250 HR ® by the company Aqualon | 1.0 g |
| Poly($C_8$–$C_{10}$)alkylglucoside as an aqueous solution containing 60% active material (A.M.) buffered with ammonium citrate (0.5%), sold under the name Oramix CG110 ® by the company SEPPIC | 8.0 g |
| Monoethanolamine qs | pH = 9.5 |

Each of the ready-to-use dye compositions described above was applied to locks of natural grey hair containing 90% white hairs, for 30 minutes. The hair was then rinsed, washed with a standard shampoo and then dried.

The hair was dyed in the shades given in the table below:

| EXAMPLE | Shade obtained |
|---|---|
| 1 | Intense red |
| 2 | Red-copper light blonde |
| 3 | Red-purple blonde |

What is claimed is:

1. A ready-to-use composition for the oxidation dyeing of keratin fibers comprising:

at least one oxidation base, at least one cationic direct dye, at least one enzyme chosen from 2-electron oxidoreductases, and at least one donor for said at least one enzyme, wherein said at least one cationic direct dye is chosen from a) compounds of formula (V) below:

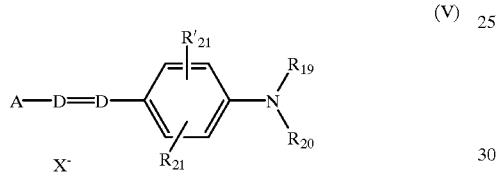

(V)

in which:

D is chosen from a nitrogen atom and a —CH group, $R_{19}$ and $R_{20}$, which may be identical or different, are chosen from a hydrogen atom; $C_1$–$C_4$ alkyl radicals; and a 4'-aminophenyl radical; or form, with a carbon atom of the benzene ring of formula (V), a heterocycle, $R_{21}$ and $R'_{21}$, which may be identical or different, are chosen from a hydrogen atom, halogen atoms, a cyano group, $C_1$–$C_4$ alkoxy radicals and acetyloxy radicals, $X^-$ is chosen from anions, A is a group chosen from structures A1 to A19 below:

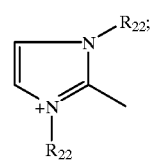  A1

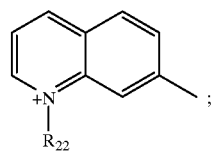  A2

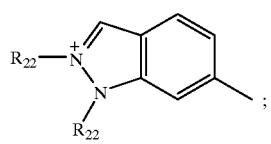  A3

-continued

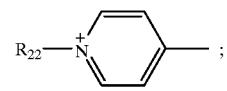  A4

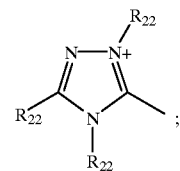  A5

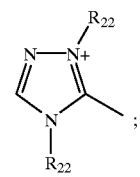  A6

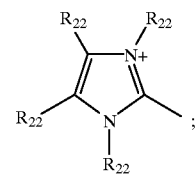  A7

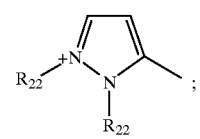  A8

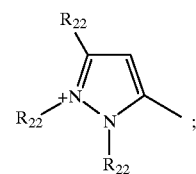  A9

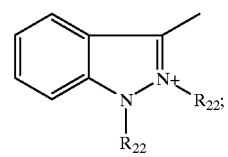  A10

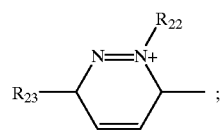  A11

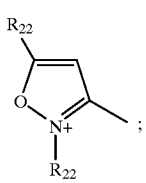  A12

-continued

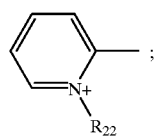 A13

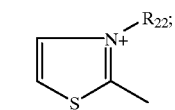 A14

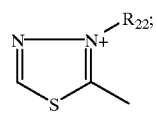 A15

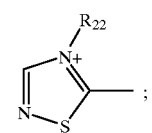 A16

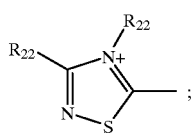 A17

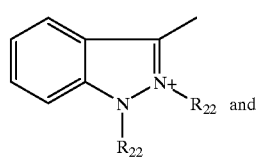 A18 and

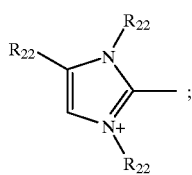 A19 in which:

$R_{22}$ is chosen from $C_1$–$C_4$ alkyl radicals which can be substituted with a hydroxyl radical, and $R_{23}$ is chosen from $C_1$–$C_4$ alkoxy radicals b) compounds of formula (VI) below:

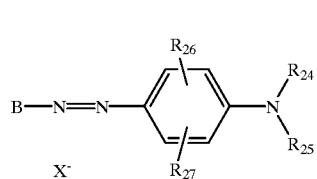 (VI)

in which:

$R_{24}$ is chosen from a hydrogen atom and $C_1$–$C_4$ alkyl radicals, $R_{25}$ is chosen from a hydrogen atom, alkyl radicals, and a 4'-aminophenyl radical or forms, with $R_{24}$, a heterocycle, $R_{26}$ and $R_{27}$, which may be identical or different, are chosen from a hydrogen atom, halogen atoms, $C_1$–$C_4$ alkyl radicals, $C_1$–$C_4$ alkoxy radicals and a —CN radical, $X^-$ is chosen from anions, B is a group chosen from structures B1 to B9 below:

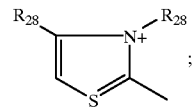 B1

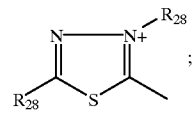 B2

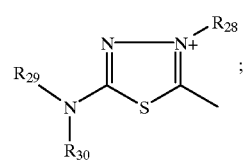 B3

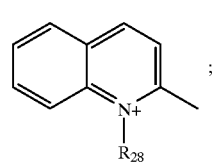 B4

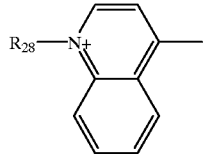 B5

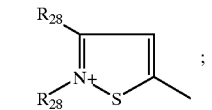 B6

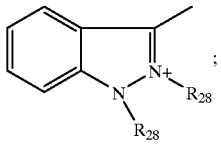 B7

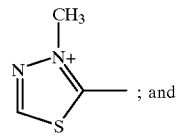 B8 ; and

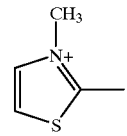 B9 in which:

$R_{28}$ is chosen from $C_1$–$C_4$ alkyl radicals, $R_{29}$ and $R_{30}$, which may be identical or different, are chosen from a hydrogen atom and $C_1$–$C_4$ alkyl radicals;

c) compounds of formulae (VII) and (VII') below:

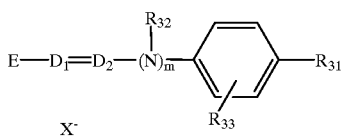
(VII)

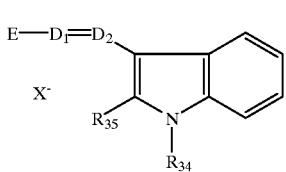
(VII')

in which:

R$_{31}$ is chosen from a hydrogen atom, C$_1$–C$_4$ alkoxy radicals, halogen atoms and an amino radical, R$_{32}$ is chosen from a hydrogen atom and C$_1$–C$_4$ alkyl radicals or forms, with a carbon atom of the benzene ring, a heterocycle which is optionally oxygenated or substituted with at least one C$_1$–C$_4$ alkyl radical, R$_{33}$ is chosen from a hydrogen atom and halogen atoms, R$_{34}$ and R$_{35}$, which may be identical or different, are chosen from a hydrogen atom and C$_1$–C$_4$ alkyl radicals, D$_1$ and D$_2$, which may be identical or different, are chosen from a nitrogen atom and a —CH group, m=0 or 1, wherein, when R$_{31}$ is an unsubstituted amino group, D$_1$ and D$_2$ are both a —CH group and m=0, X$^-$ is chosen from anions, E is a group chosen from structures E1 to E8 below:

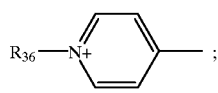
E1

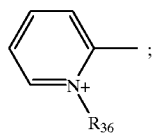
E2

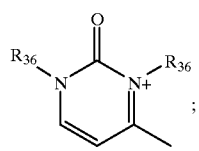
E3

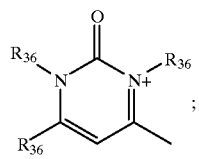
E4

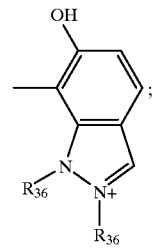
E5

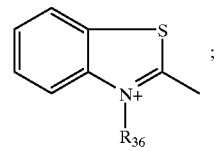
E6

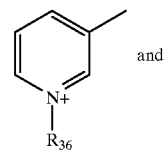
E7 and

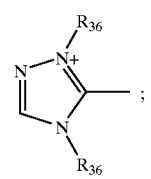
E8 in which:

R$_{36}$ is chosen from C$_1$–C$_4$ alkyl radicals; and when m=0 and when D$_1$ is a nitrogen atom, E can also be chosen from a group of structure E9 below:

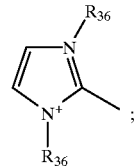
E9 in which:

R$_{36}$ is chosen from C$_1$–C$_4$ alkyl radicals, and d) the compound of formula (V43) below:

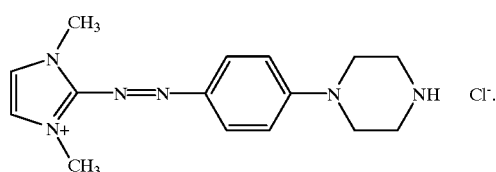
(V43)

2. The composition according to claim 1, wherein said keratin fibers are human keratin fibers.

3. The composition according to claim 2, wherein said human keratin fibers are hair.

4. The composition according to claim 1, wherein said at least one enzyme is chosen from pyranose oxidases, glucose oxidases, glycerol oxidases, lactate oxidases, pyruvate oxidases and uricases.

5. The composition according to claim 1, wherein said at least one enzyme is chosen from uricases of animal, microbiological and biotechnological origin.

6. The composition according to claim 1, wherein said at least one enzyme is present in an amount ranging from 0.01 to 20% by weight relative to the total weight of said composition.

7. The composition according to claim 6, wherein said at least one enzyme is present in an amount ranging from 0.1 to 5% by weight relative to the total weight of said composition.

8. The composition according to claim 1, wherein said at least one donor for said at least one enzyme is chosen from D-glucose, L-sorbose, D-xylose, glycerol, dihydroxyacetone, lactic acid and its salts, pyruvic acid and its salts, and uric acid and its salts.

9. The composition according to claim 8, wherein said at least one donor is chosen from uric acid and its salts.

10. The composition according to claim 1, wherein said at least one donor is present in an amount ranging from 0.01 to 20% by weight relative to the total weight of said composition.

11. The composition according to claim 10, wherein said at least one donor is present in an amount ranging from 0.1 to 5% by weight relative to the total weight of said composition.

12. The composition according to claim 1, wherein said at least one oxidation base is chosen from para-phenylenediamines, double bases, para-aminophenols, ortho-aminophenols and heterocyclic oxidation bases.

13. The composition according to claim 12, wherein said para-phenylenediamines are chosen from compounds of formula (I) below, and acid-addition salts thereof:

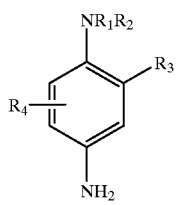

(I)

in which:
R$_1$ is chosen from a hydrogen atom, C$_1$–C$_4$ alkyl radicals, C$_1$–C$_4$ monohydroxyalkyl radicals, C$_2$–C$_4$ polyhydroxyalkyl radicals, (C$_1$–C$_4$)alkoxy(C$_1$–C$_4$)alkyl radicals, C$_1$–C$_4$ alkyl radicals substituted with a nitrogenous group, a phenyl radical and a 4'-aminophenyl radical;

R$_2$ is chosen from a hydrogen atom, C$_1$–C$_4$ alkyl radicals, C$_1$–C$_4$ monohydroxyalkyl radicals, C$_2$–C$_4$ polyhydroxyalkyl radicals, (C$_1$–C$_4$)alkoxy(C$_1$–C$_4$)alkyl radicals and C$_1$–C$_4$ alkyl radicals substituted with a nitrogenous group;

R$_3$ is chosen from a hydrogen atom, halogen atoms, C$_1$–C$_4$ alkyl radicals, C$_1$–C$_4$ monohydroxyalkyl radicals, C$_1$–C$_4$ hydroxyalkoxy radicals, acetylamino(C$_1$–C$_4$)alkoxy radicals, C$_1$–C$_4$ mesylaminoalkoxy radicals and carbamoylamino(C$_1$–C$_4$)alkoxy radicals, R$_4$ is chosen from a hydrogen atom, halogen atoms and C$_1$–C$_4$ alkyl radicals.

14. The composition according to claim 13, wherein said halogen atoms are chosen from fluorine, chlorine, bromine, and iodine.

15. The composition according to claim 13, wherein said para-phenylenediamines of formula (I) are chosen from: para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and acid-addition salts thereof.

16. The composition according to claim 12, wherein said double bases are chosen from compounds of formula (II) below, and acid-addition salts thereof:

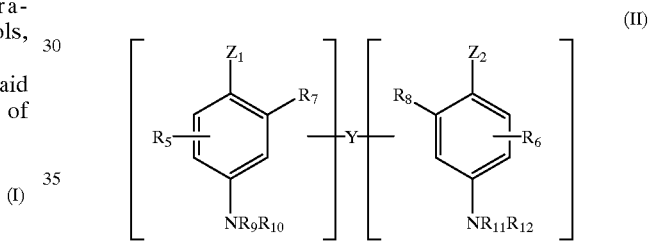

(II)

in which:
Z$_1$ and Z$_2$, which may be identical or different, are chosen from a hydroxyl radical, and a —NH$_2$ radical which may be substituted with C$_1$–C$_4$ alkyl radicals or with a linker arm Y;

the linker arm Y is chosen from linear and branched alkylene chains containing from 1 to 14 carbon atoms, which may be interrupted by or terminated with at least one entity chosen from nitrogenous groups and hetero atoms, and optionally having at least one substituent chosen from hydroxyl and C$_1$–C$_6$ alkoxy radicals;

R$_5$ and R$_6$, which may be identical or different, are chosen from a hydrogen atom, halogen atoms, C$_1$–C$_4$ alkyl radicals, C$_1$–C$_4$ monohydroxyalkyl radicals, C$_2$–C$_4$ polyhydroxyalkyl radicals, C$_1$–C$_4$ aminoalkyl radicals and a linker arm Y;

R$_7$, R$_8$, R$_9$, R$_{10}$, R$_{11}$ and R$_{12}$, which may be identical or different, are chosen from a hydrogen atom, linker arms Y and C$_1$–C$_4$ alkyl radicals;

wherein said compounds of formula (II) and salts thereof contain only one linker arm Y per molecule.

17. The composition according to claim 16, wherein said hetero atoms are chosen from oxygen, sulfur, and nitrogen.

18. The composition according to claim 16, wherein said double bases of formula (II) are chosen from: N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)

tetramethylenediamine, N,N'-bis(β-hydroxyethyl)-N,N'-bis (4-aminophenyl)tetramethylenediamine, N,N'-bis(4-methylaminophenyl)tetramethylenediamine, N,N'-bis (ethyl)-N,N'-bis(4'-amino-3'-methylphenyl) ethylenediamine, 1,8-bis(2,5-diaminophenoxy)-3,5-dioxaoctane, and acid-addition salts thereof.

19. The composition according to claim 12, wherein said para-aminophenols are chosen from compounds of formula (III) below, and acid-addition salts thereof:

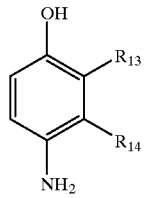

(III)

in which:
- $R_{13}$ is chosen from a hydrogen atom, halogen atoms, $C_1$–$C_4$ alkyl radicals, $C_1$–$C_4$ monohydroxyalkyl radicals, $(C_1$–$C_4)$alkoxy$(C_1$–$C_4)$alkyl radicals, $C_1$–$C_4$ aminoalkyl radicals, and hydroxy$(C_1$–$C_4)$alkylamino $(C_1$–$C_4)$alkyl radicals,
- $R_{14}$ is chosen from a hydrogen atom, halogen atoms $C_1$–$C_4$ alkyl radicals, $C_1$–$C_4$ monohydroxyalkyl radicals, $C_2$–$C_4$ polyhydroxyalkyl radicals, $C_1$–$C_4$ aminoalkyl radicals, $C_1$–$C_4$ cyanoalkyl radicals, and $(C_1$–$C_4)$alkoxy-$(C_1$–$C_4)$alkyl radicals, wherein at least one of said radicals $R_{13}$ and $R_{14}$ is a hydrogen atom.

20. The composition according to claim 19, wherein said para-aminophenols of formula (III) are chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and acid-addition salts thereof.

21. The composition according to claim 12, wherein said ortho-aminophenols are chosen from 2-aminophenol, 2-amino-5-methylphenol, 2-amino-6-methylphenol, 5-acetamido-2-aminophenol, and acid-addition salts thereof.

22. The composition according to claim 12, wherein said heterocyclic oxidation bases are chosen from pyridine compounds, pyrimidine compounds, pyrazole compounds, pyrazolopyrimidine compounds, and acid-addition salts thereof.

23. The composition according to claim 22, wherein said heterocyclic oxidation bases are chosen from:
pyridine compounds chosen from: 2,5-diaminopyridine, 2-(4-methoxyphenyl)amino-3-amino-pyridine, 2,3-diamino-6-methoxypyridine, 2-(β-methoxy-ethyl) amino-3-amino-6-methoxypyridine, 3,4-diaminopyridine, and acid-addition salts thereof,
pyrimidine compounds chosen from: 2,4,5,6-tetraamino-pyrimidine, 4-hydroxy-2,5,6-triaminopyrimidine, 2-hydroxy-4,5,6-triamino-pyrimidine, 2,4-dihydroxy-5,6-diaminopyrimidine, 2,5,6-tri-amino-pyrimidine, and acid-addition salts thereof,
pyrazole compounds chosen from: 4,5-diamino-1-methyl-pyrazole, 3,4-diaminopyrazole, 4,5-diamino-1-(4'-chlorobenzyl)pyrazole, 4,5-diamino-1,3-dimethyl-pyrazole, 4,5-diamino-3-methyl-1-phenylpyrazole, 4,5-diamino-1-methyl-3-phenylpyrazole, 4-amino-1,3-di-methyl-5-hydrazinopyrazole, 1-benzyl-4,5-diamino-3-methyl-pyrazole, 4,5-diamino-3-tert-butyl-1-methyl-pyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methyl-pyrazole, 4,5-diamino-3-hydroxymethyl-1-iso-propyl-pyrazole, 4,5-diamino-3-methyl-1-isopropyl-pyrazole, 4-amino-5-(2'-amino-ethyl)amino-1,3-dimethyl-pyrazole, 3,4,5-triamino-pyrazole, 1-methyl-3,4,5-tri-amino-pyrazole, 3,5-diamino-1-methyl-4-methylamino-pyrazole, 3,5-diamino4-(β-hydroxyethyl)amino-1-methyl-pyrazole, and acid-addition salts thereof, and
pyrazolopyrimidine compounds chosen from:
pyrazolo[1,5-a]pyrimidine-3,7-diamine;
2,5-dimethylpyrazolo[1,5-a]pyrimidine-3,7-diamine;
pyrazolo[1,5-a]pyrimidine-3,5-diamine;
2,7-dimethylpyrazolo[1,5-a]pyrimidine-3,5-diamine;
3-aminopyrazolo[1,5-a]pyrimidin-7-ol;
3-aminopyrazolo[1,5-a]pyrimidin-5-ol;
2-(3-aminopyrazolo[1,5-a]pyrimidin-7-ylamino)ethanol;
2-(7-aminopyrazolo[1,5-a]pyrimidin-3-ylamino)ethanol;
2-[(3-aminopyrazolo[1,5-a]pyrimidin-7-yl)-(2-hydroxy-ethyl)amino]ethanol;
2-[(7-aminopyrazolo[1,5-a]pyrimidin-3-yl)-(2-hydroxy-ethyl)amino]ethanol;
5,6-dimethylpyrazolo[1,5-a]pyrimidine-3,7-diamine;
2,6-dimethylpyrazolo[1,5-a]pyrimidine-3,7-diamine;
2,5,N7,N7-tetramethylpyrazolo[1,5-a]pyrimidine-3,7-diamine;
and addition salts thereof and tautomeric forms thereof, when a tautomeric equilibrium exists.

24. The composition according to claim 1, wherein said at least one oxidation base is present in an amount ranging from 0.0005 to 12% by weight relative to the total weight of the composition.

25. The composition according to claim 24, wherein said at least one oxidation base is present in an amount ranging from 0.005 to 6% by weight relative to the total weight of the composition.

26. The composition according to claim 1, wherein in the definition of $R_{19}$ and $R_{20}$, said $C_1$–$C_4$ alkyl radicals are substituted with a radical chosen from —CN, —OH and —NH$_2$ radicals.

27. The composition according to claim 1, wherein in the definition of $R_{19}$ and $R_{20}$, said heterocycle comprises at least one heteroatom chosen from oxygen and nitrogen.

28. The composition according to claim 1, wherein in the definition of $R_{19}$ and $R_{20}$, said heterocycle is substituted with at least one radical chosen from $C_1$–$C_4$ alkyl radicals.

29. The composition according to claim 1, wherein said anions X$^-$ are chosen from chlorides, methyl sulphates and acetates.

30. The composition according to claim 1, wherein in the definition of $R_{25}$ said alkyl radicals are substituted with a —CN radical or an amino group.

31. The composition according to claim 1, wherein said halogen atoms are chosen from fluorine, bromine, chlorine, and iodine.

32. The composition according to claim 1, wherein said cationic direct dyes of formula (V) are chosen from direct dyes of formulae (V1) to (V52) below:

(V1) — (V17) Chemical structures not transcribed.

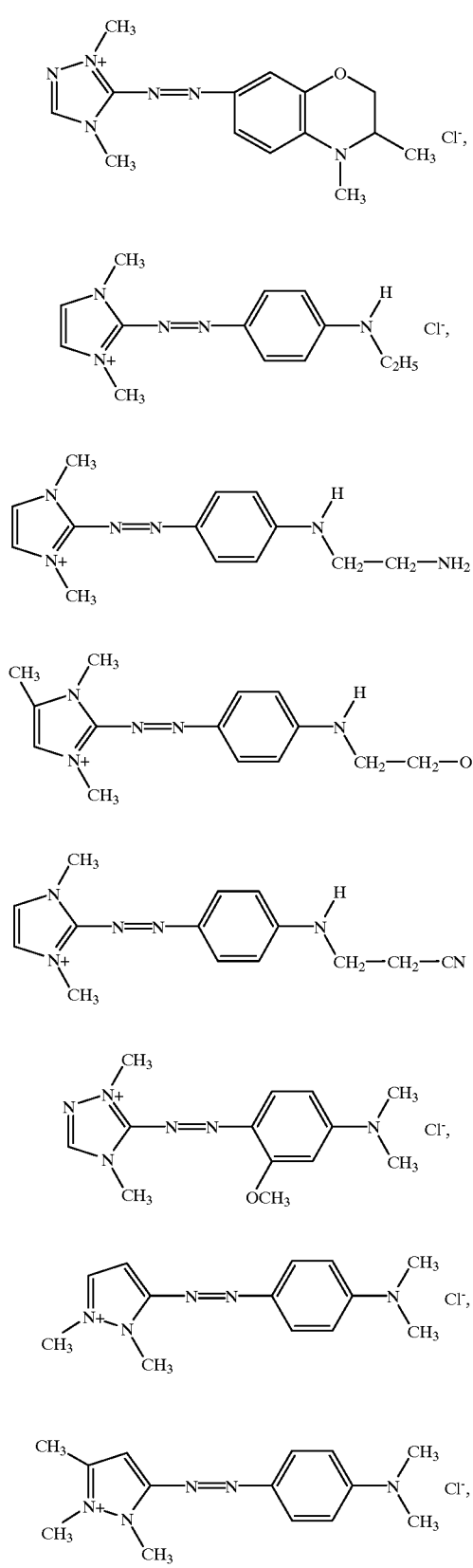
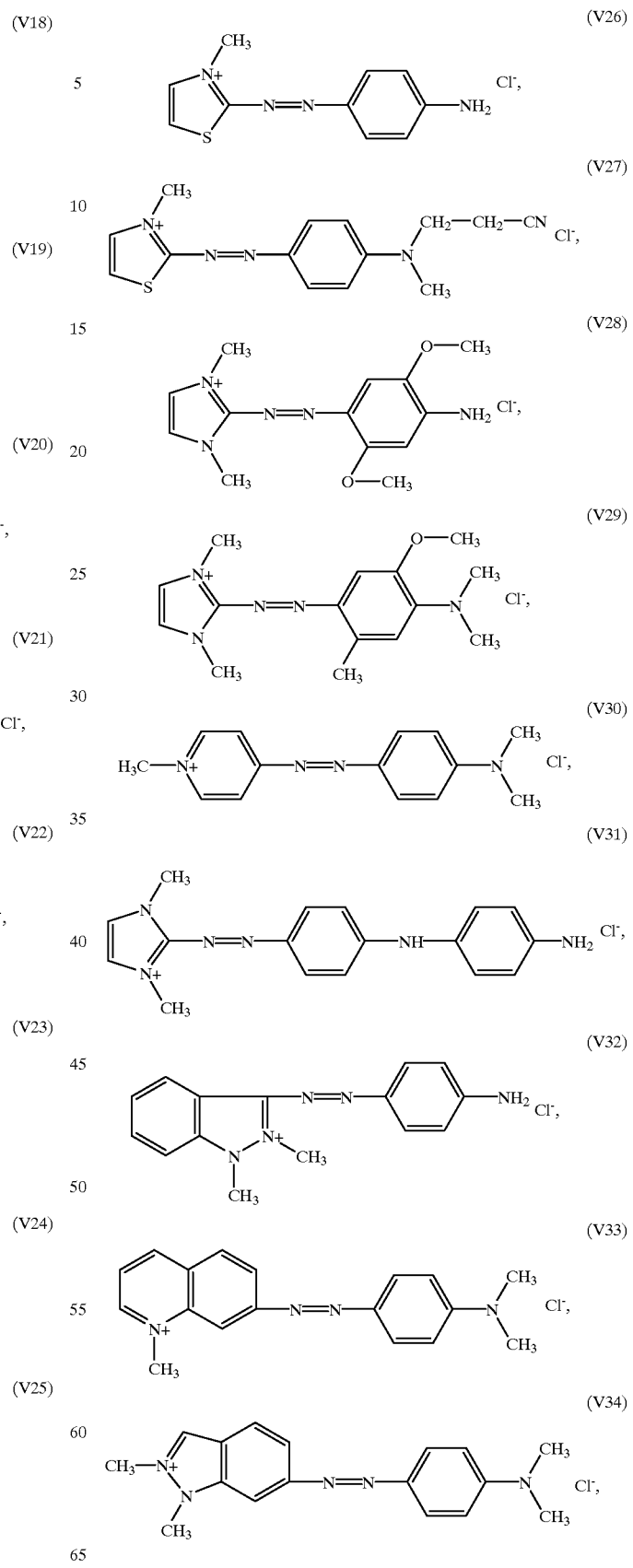

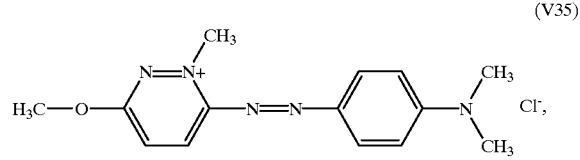 (V35)
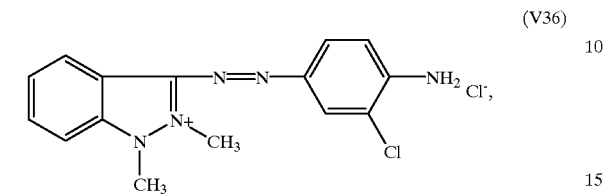 (V36)
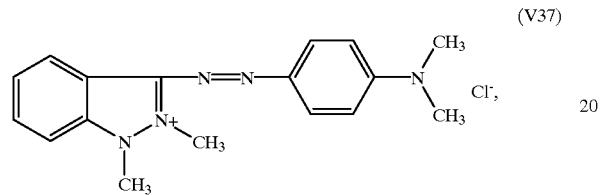 (V37)
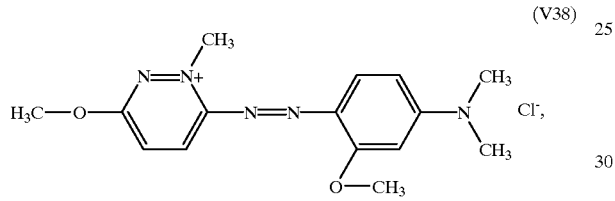 (V38)
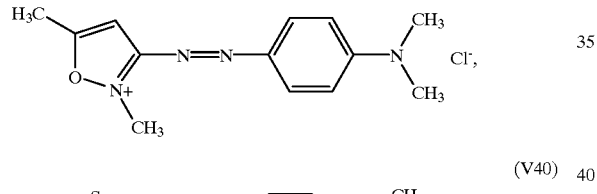 (V39)
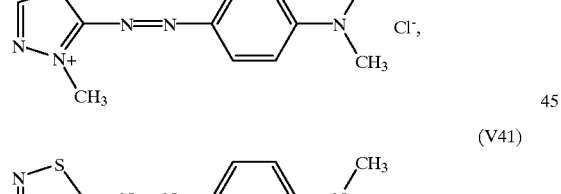 (V40)
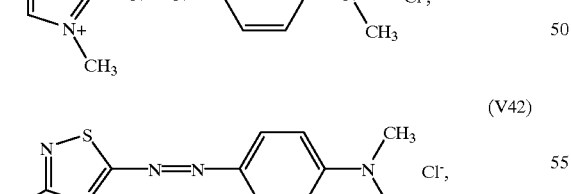 (V41)
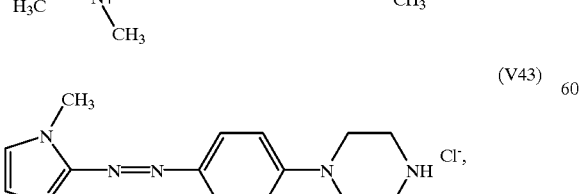 (V42)
 (V43)
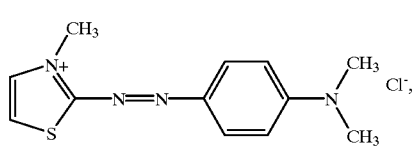 (V44)
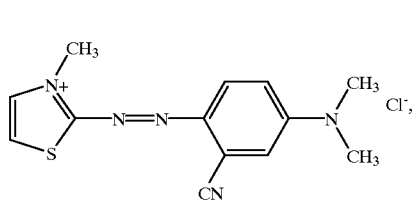 (V45)
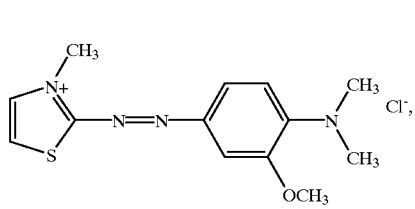 (V46)
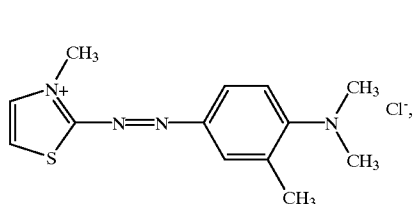 (V47)
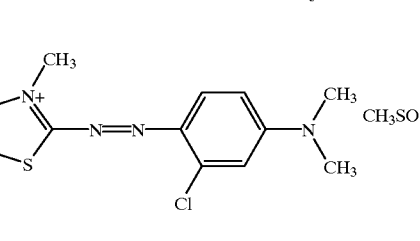 (V48)
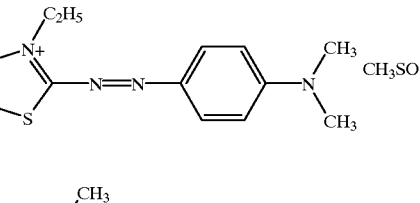 (V49)
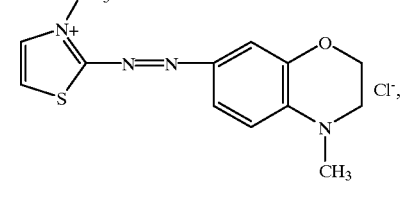 (V50)
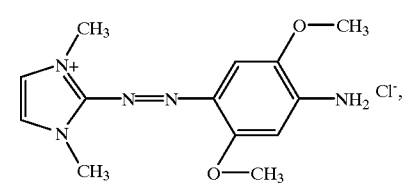 (V51)
and (V52)

33. The composition according to claim 1, wherein said cationic direct dyes of formula (VI) are chosen from direct dyes of formulae (VI1) to (VI12) below:

(VI1)

(VI2)

(VI3)

(VI4)

(VI5)

(VI6)

(VI7)

(VI8)

(VI9)

(VI10)

(VI11)

(VI12)

34. The composition according to claim 1, wherein said cationic direct dyes of formula (VII) are chosen from direct dyes of formulae (VII1) to (VII18) below:

(VII1)

(VII2)

(VII3)

(VII4)
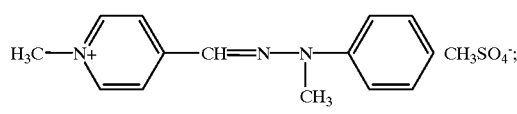
(VII5)
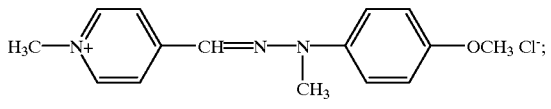
(VII6)
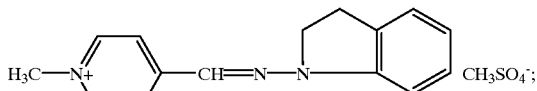
(VII7)
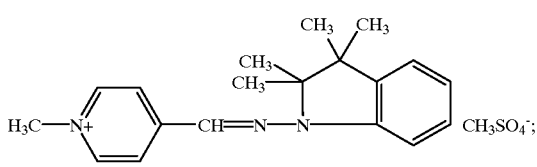
(VII8)
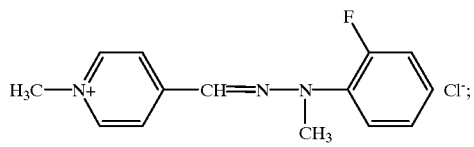
(VII9)
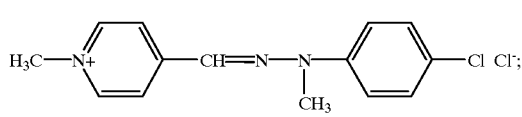
(VII10)
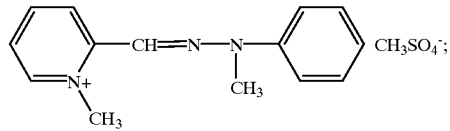
(VII11)
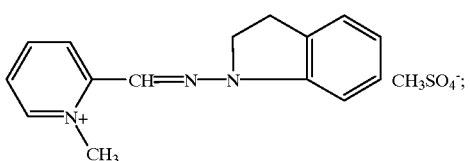
(VII12)
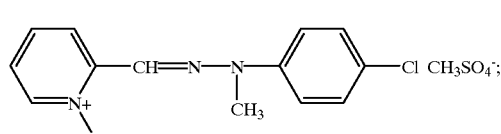
(VII13)
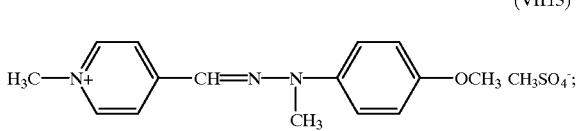
(VII14)
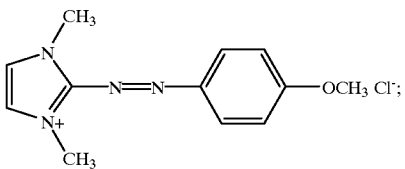
(VII15)
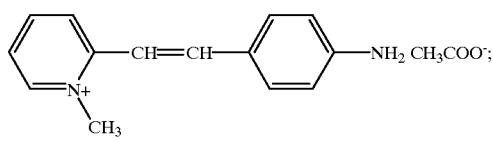
(VII16)
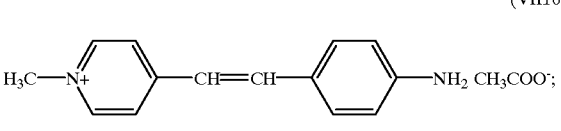
(VII17)
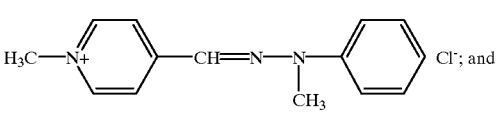
(VII18)
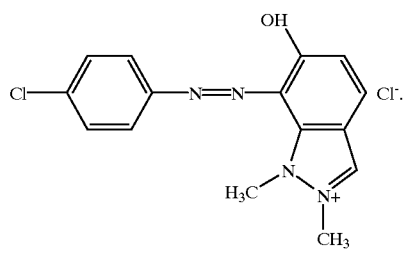
35. The composition according to claim 1, wherein said cationic direct dyes of formula (VII') are chosen from direct dyes of formulae (VII'1) to (VII'3) below:
(VII'1)
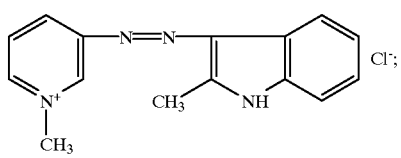
(VII'2)
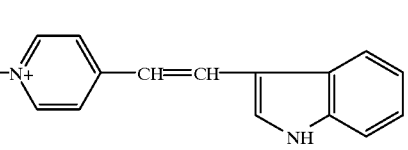
(VII'3)
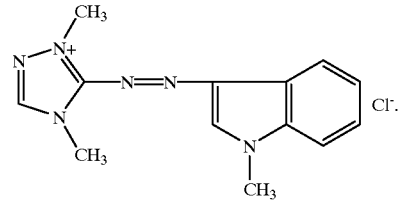

36. The composition according to claim 1, wherein said at least one cationic direct dye is present in an amount ranging from 0.001 to 10% by weight relative to the total weight of said composition.

37. The composition according to claim 36, wherein said at least one cationic direct dye is present in an amount ranging from 0.05 to 5% by weight relative to the total weight of said composition.

38. The composition according to claim 1, wherein said acid-addition salts are chosen from the hydrochlorides, hydrobromides, sulphates, tartrates, lactates and acetates.

39. The composition according to claim 1, further comprising water or a mixture of water and at least one organic solvent.

40. The composition according to claim 1, wherein said composition has a pH ranging from 5 to 11.

41. The composition according to claim 1, further comprising at least one peroxidase.

42. A ready-to-use composition for the oxidation dyeing of keratin fibers comprising:

at least one oxidation base chosen from:

para-phenylenediamines chosen from: para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and acid-addition salts thereof;

double bases chosen from: N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and acid-addition salts thereof;

para-aminophenols chosen from: para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and acid-addition salts thereof;

ortho-aminophenols chosen from: 2-aminophenol, 2-amino-5-methylphenol, 2-amino-6-methylphenol, 5-acetamido-2-aminophenol, and acid-addition salts thereof pyridine compounds chosen from: 2,5-diaminopyridine, 2-(4-methoxyphenyl)amino-3-amino-pyridine, 2,3-diamino-6-methoxypyridine, 2-(β-methoxy-ethyl)amino-3-amino-6-methoxypyridine, 3,4-diaminopyridine, and acid-addition salts thereof, pyrimidine compounds chosen from: 2,4,5,6-tetraamino-pyrimidine, 4-hydroxy-2,5,6-triaminopyrimidine, 2-hydroxy-4,5,6-triamino-pyrimidine, 2,4-dihydroxy-5,6-diaminopyrimidine, 2,5,6-tri-amino-pyrimidine, and acid-addition salts thereof, pyrazole compounds chosen from: 4,5-diamino-1-methyl-pyrazole, 3,4-diaminopyrazole, 4,5-diamino-1-(4'-chlorobenzyl)pyrazole, 4,5-diamino-1,3-dimethyl-pyrazole, 4,5-diamino-3-methyl-1-phenylpyrazole, 4,5-diamino-1-methyl-3-phenylpyrazole, 4-amino-1,3-di-methyl-5-hydrazinopyrazole, 1-benzyl-4,5-diamino-3-methyl-pyrazole, 4,5-diamino-3-tert-butyl-1-methyl-pyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methyl-pyrazole, 4,5-diamino-3-hydroxymethyl-1-iso-propyl-pyrazole, 4,5-diamino-3-methyl-1-isopropyl-pyrazole, 4-amino-5-(2'-amino-ethyl)amino-1,3-dimethyl-pyrazole, 3,4,5-triamino-pyrazole, 1-methyl-3,4,5-tri-amino-pyrazole, 3,5-diamino-1-methyl-4-methylamino-pyrazole, 3,5-diamino-4-(β-hydroxyethyl)amino-1-methyl-pyrazole, and acid-addition salts thereof, pyrazolopyrimidine compounds chosen from:
pyrazolo[1,5-a]pyrimidine-3,7-diamine;
2,5-dimethylpyrazolo[1,5-a]pyrimidine-3,7-diamine;
pyrazolo[1,5-a]pyrimidine-3,5-diamine;
2,7-dimethylpyrazolo[1,5-a]pyrimidine-3,5-diamine;
3-aminopyrazolo[1,5-a]pyrimidin-7-ol ;
3-aminopyrazolo[1,5-a]pyrimidin-5-ol;
2-(3-aminopyrazolo[1,5-a]pyrimidin-7-ylamino)ethanol;
2-(7-aminopyrazolo[1,5-a]pyrimidin-3-ylamino)ethanol;
2-[(3-aminopyrazolo[1,5-a]pyrimidin-7-yl)-(2-hydroxy-ethyl)amino]ethanol;
2-[(7-aminopyrazolo[1,5-a]pyrimidin-3-yl)-(2-hydroxy-ethyl)amino]ethanol;
5,6-dimethylpyrazolo[1,5-a]pyrimidine-3,7-diamine;
2,6-dimethylpyrazolo[1,5-a]pyrimidine-3,7-diamine;
2,5,N7,N7-tetramethylpyrazolo[1,5-a]pyrimidine-3,7-diamine;

and addition salts thereof and tautomeric forms thereof, when a tautomeric equilibrium exists;

at least one cationic direct dye chosen from:

direct dyes chosen from dyes of formulae (V1) to (V52) below:

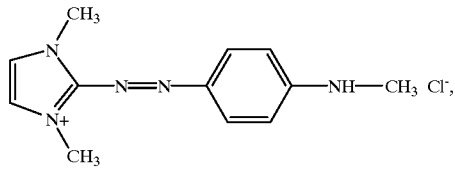

(V1)

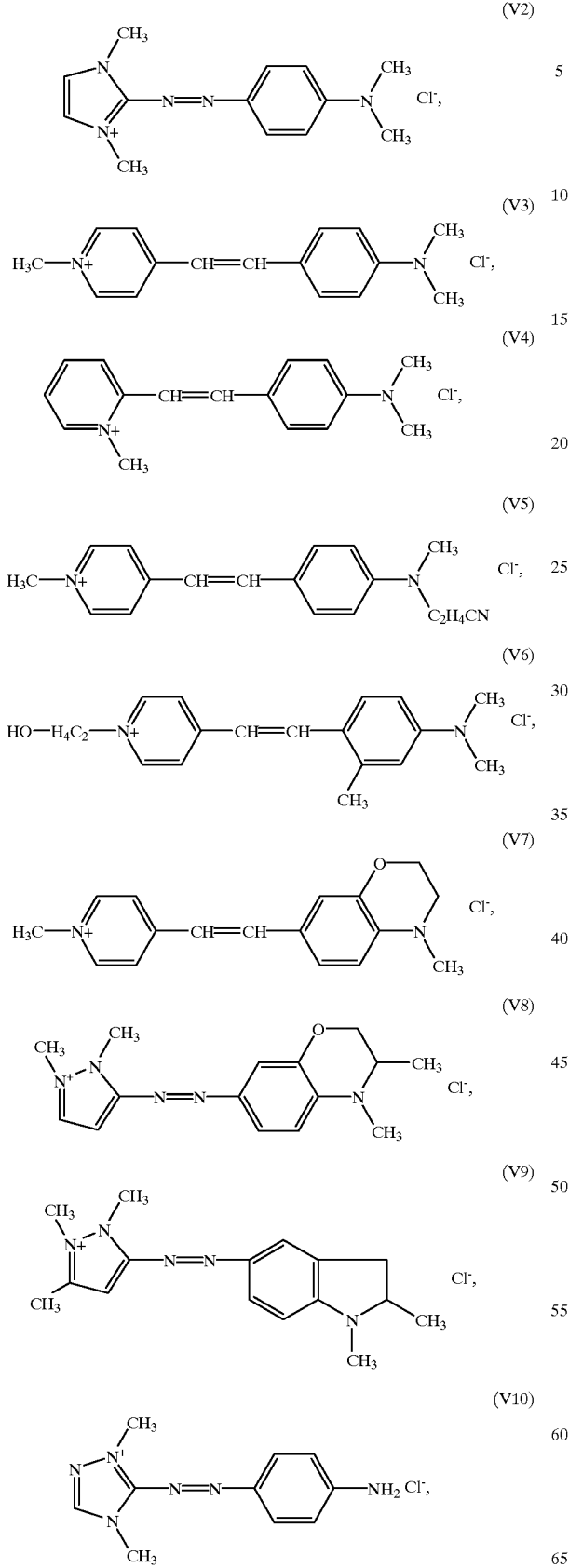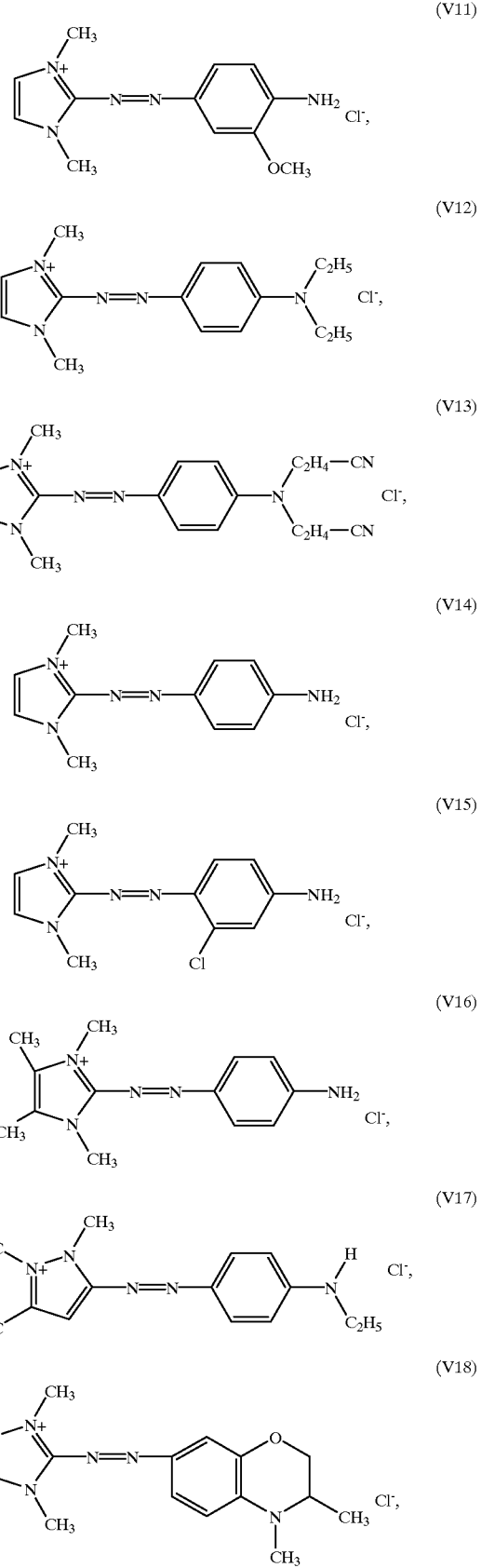

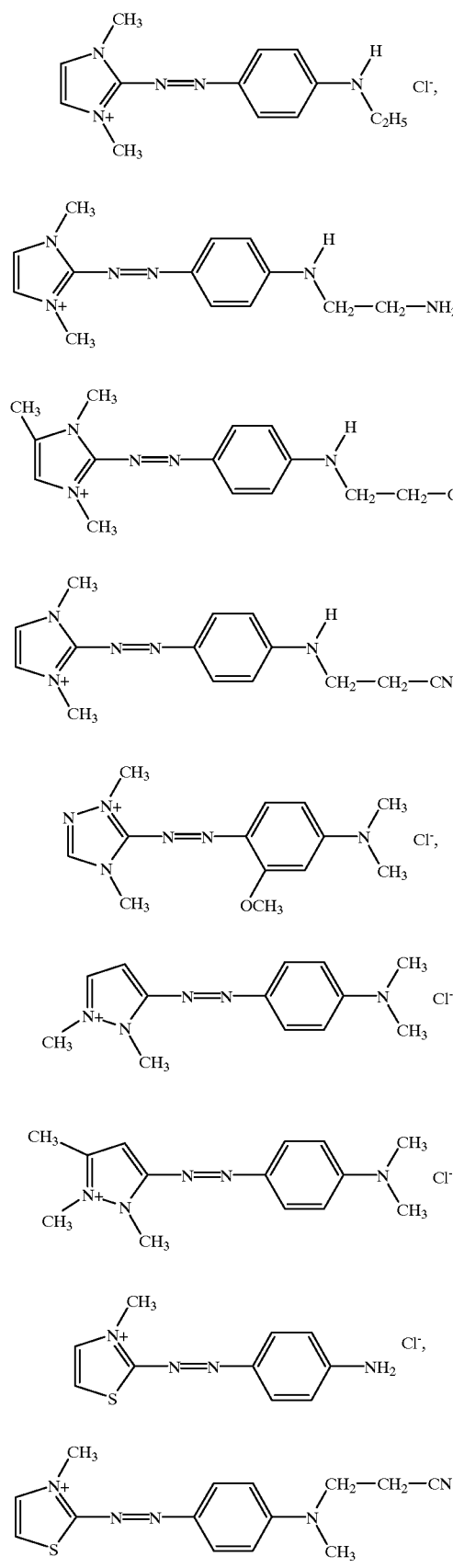

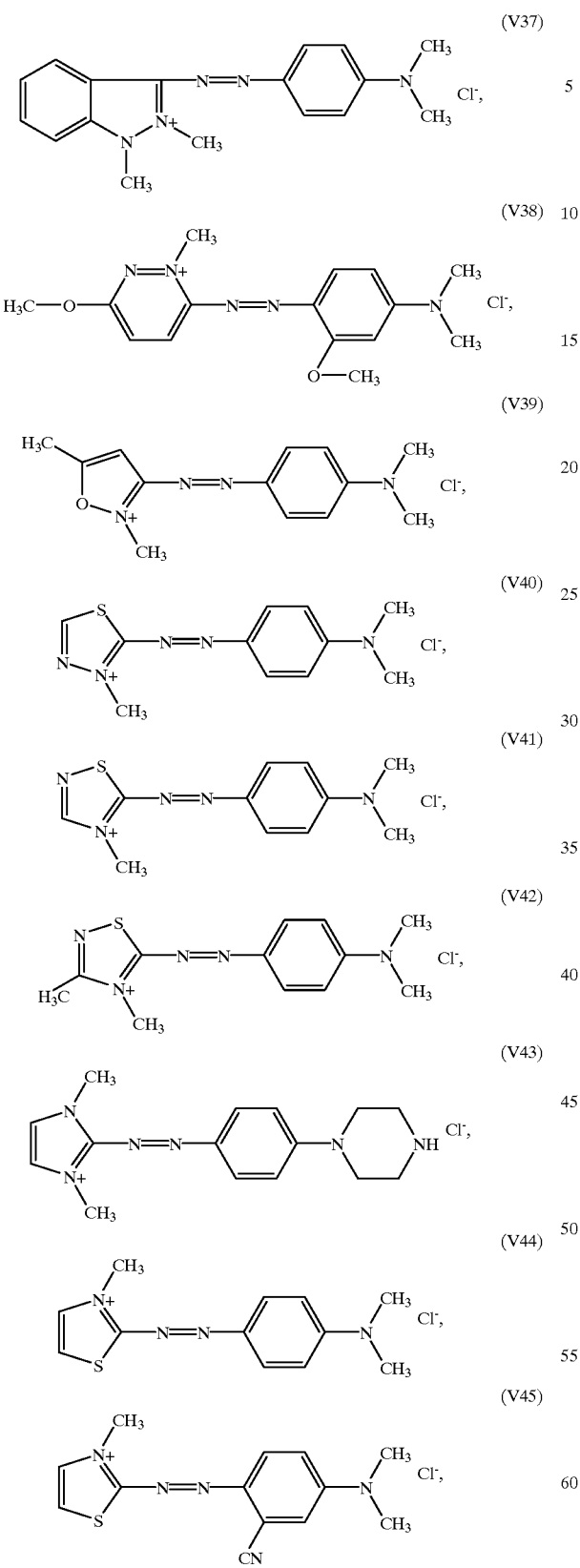
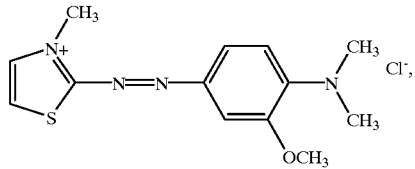
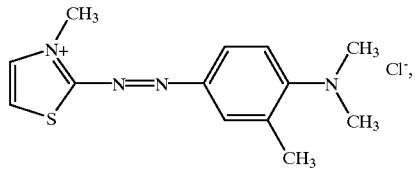
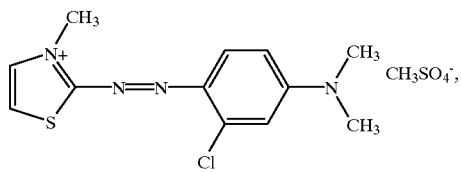
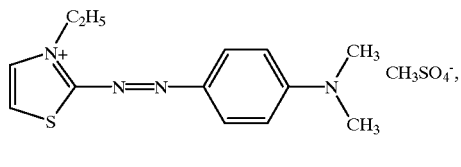
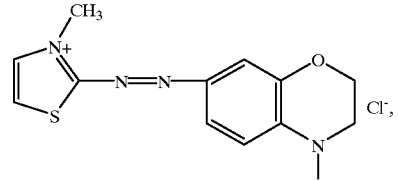
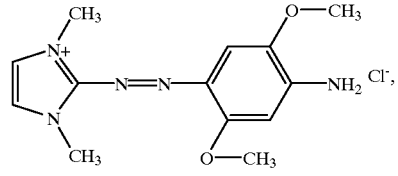
and
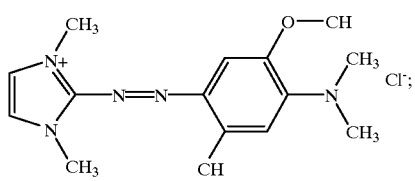

direct dyes chosen from dyes of formulae (VI1) to (VI12) below:
(VI1)
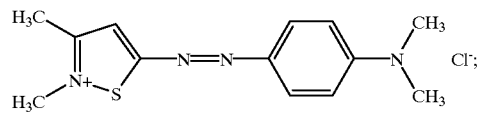
(VI2)
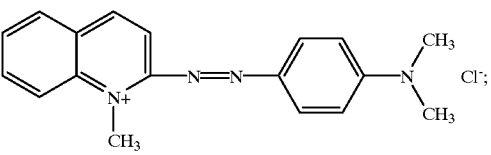
(VI3)
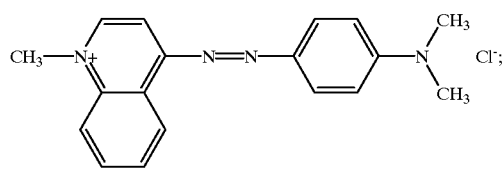
(VI4)
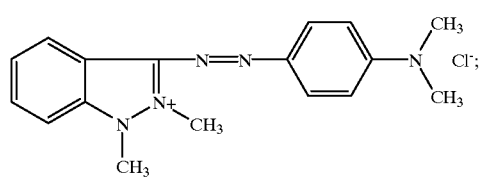
(VI5)
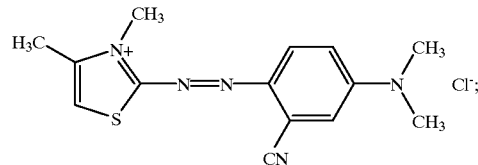
(VI6)
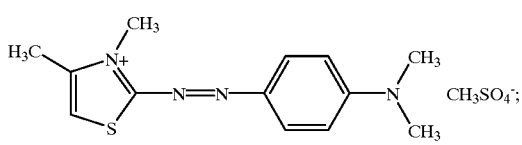
(VI7)
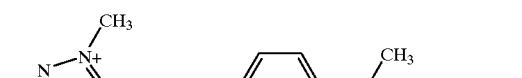
(VI8)
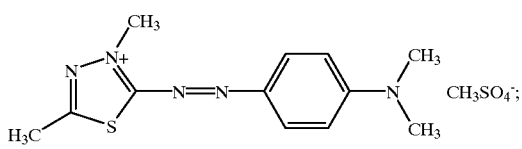
(VI9)
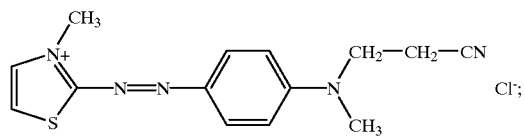
(VI10)
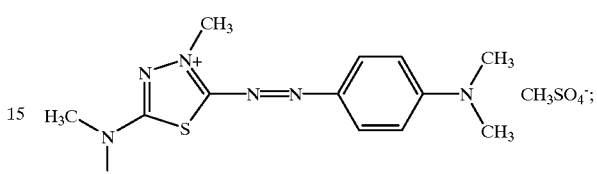
(VI11)
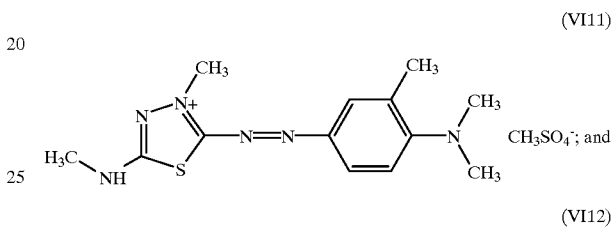 and
(VI12)
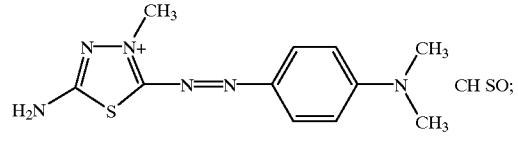
cationic direct dyes chosen from dyes of formulae (VII1) to (VII18) below:
(VII1)
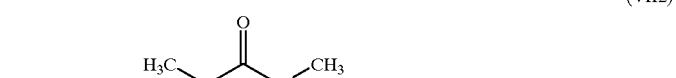
(VII2)
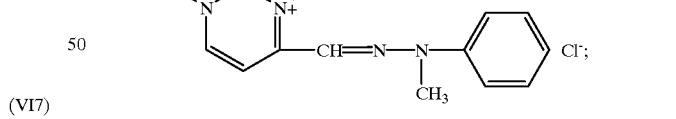
(VII3)
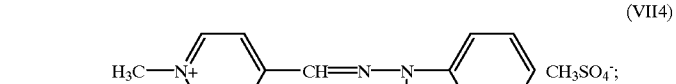
(VII4)

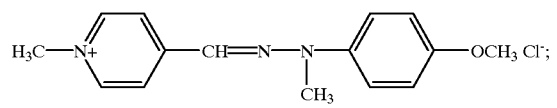 (VII5)
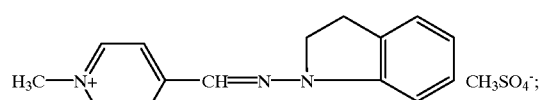 (VII6)
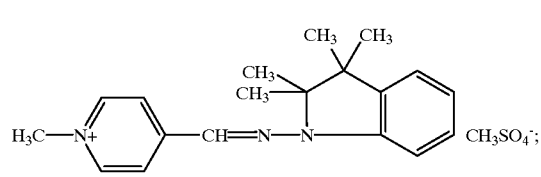 (VII7)
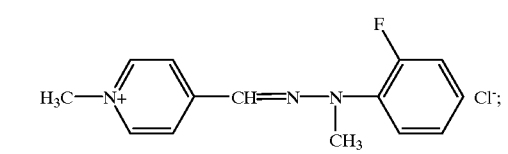 (VII8)
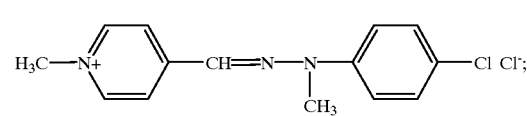 (VII9)
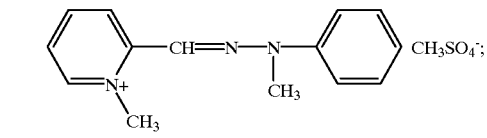 (VII10)
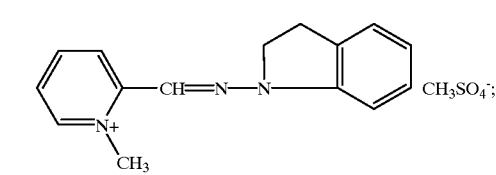 (VII11)
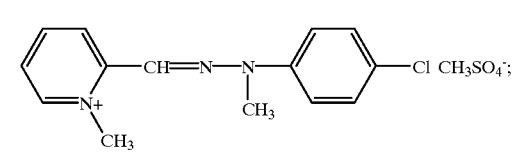 (VII12)
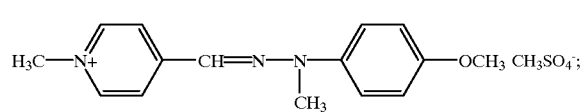 (VII13)
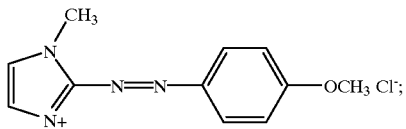 (VII14)
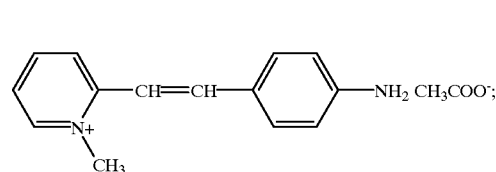 (VII15)
 (VII16)
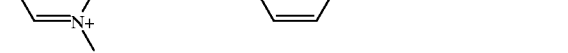 (VII17)
 (VII18)
cationic direct dyes chosen from direct dyes of (VII'1) to (VII'3) below:
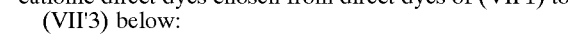 (VII'1)
 (VII'2)
 (VII'3)

at least one 2-electron oxidoreductase chosen from pyranose oxidases, glucose oxidases, glycerol oxidases, lactate oxidases, pyruvate oxidases and uricases, and at least one donor chosen from D-glucose, L-sorbose, D-xylose, glycerol, dihydroxyacetone, lactic acid and its salts, pyruvic acid and its salts, and uric acid and its salts.

43. A ready-to-use composition for the oxidation dyeing of keratin fibers comprising:

at least one oxidation base chosen from: para-phenylenediamine and para-aminophenol;

at least one cationic direct dye chosen from:

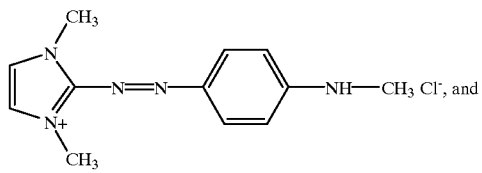

(V1)

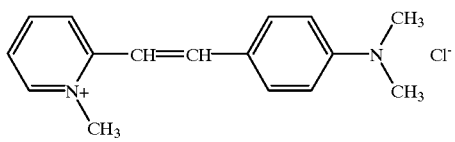

(V4)

uricase; and uric acid.

44. A process for dyeing keratin fibers, comprising applying at least one ready-to-use dye composition for the oxidation dyeing of keratin fibers to said fibers and developing for a period sufficient to achieve a desired coloration, wherein said ready-to-use dye composition comprises:

at least one oxidation base chosen from:

para-phenylenediamines chosen from: para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and acid-addition salts thereof;

double bases chosen from: N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and acid-addition salts thereof;

para-aminophenols chosen from: para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and acid-addition salts thereof;

ortho-aminophenols chosen from: 2-aminophenol, 2-amino-5-methylphenol, 2-amino-6-methylphenol, 5-acetamido-2-aminophenol, and acid-addition salts thereof pyridine compounds chosen from: 2,5-diaminopyridine, 2-(4-methoxyphenyl)amino-3-amino-pyridine, 2,3-diamino-6-methoxypyridine, 2-(β-methoxy-ethyl)amino-3-amino-6-methoxypyridine, 3,4-diaminopyridine, and acid-addition salts thereof, pyrimidine compounds chosen from: 2,4,5,6-tetraamino-pyrimidine, 4-hydroxy-2,5,6-triaminopyrimidine, 2-hydroxy-4,5,6-triamino-pyrimidine, 2,4-dihydroxy-5,6-diaminopyrimidine, 2,5,6-tri-amino-pyrimidine, and acid-addition salts thereof, pyrazole compounds chosen from: 4,5-diamino-1-methyl-pyrazole, 3,4-diaminopyrazole, 4,5-diamino-1-(4'-chlorobenzyl)pyrazole, 4,5-diamino-1,3-dimethyl-pyrazole, 4,5-diamino-3-methyl-1-phenylpyrazole, 4,5-diamino-1-methyl-3-phenylpyrazole, 4-amino-1,3-di-methyl-5-hydrazinopyrazole, 1-benzyl4,5-diamino-3-methyl-pyrazole, 4,5-diamino-3-tert-butyl-1-methyl-pyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methyl-pyrazole, 4,5-diamino-3-hydroxymethyl-1-iso-propyl-pyrazole, 4,5-diamino-3-methyl-1-isopropyl-pyrazole, 4-amino-5-(2'-amino-ethyl)amino-1,3-dimethyl-pyrazole, 3,4,5-triamino-pyrazole, 1-methyl-3,4,5-tri-amino-pyrazole, 3,5-diamino-1-methyl-4-methylamino-pyrazole, 3,5-diamino4-(β-hydroxyethyl)amino-1-methyl-pyrazole, and acid-addition salts thereof, pyrazolopyrimidine compounds chosen from:
pyrazolo[1,5-a]pyrimidine-3,7-diamine;
2,5-dimethylpyrazolo[1,5-a]pyrimidine-3,7-diamine;
pyrazolo[1,5-a]pyrimidine-3,5-diamine;
2,7-dimethylpyrazolo[1,5-a]pyrimidine-3,5-diamine;
3-aminopyrazolo[1,5-a]pyrimidin-7-ol;
3-aminopyrazolo[1,5-a]pyrimidin-5-ol;
2-(3-aminopyrazolo[1,5-a]pyrimidin-7-ylamino)ethanol;
2-(7-aminopyrazolo[1,5-a]pyrimidin-3-ylamino)ethanol;
2-[(3-aminopyrazolo[1,5-a]pyrimidin-7-yl)-(2-hydroxyethyl)amino]ethanol;
2-[(7-aminopyrazolo[1,5-a]pyrimidin-3-yl)-(2-hydroxyethyl)amino]ethanol;
5,6-dimethylpyrazolo[1,5-a]pyrimidine-3,7-diamine;
2,6-dimethylpyrazolo[1,5-a]pyrimidine-3,7-diamine;
2,5,N7, N7-tetramethylpyrazolo[1,5-a]pyrimidine-3,7-diamine;
and addition salts thereof and the tautomeric forms thereof, when a tautomeric equilibrium exists;

at least one cationic direct dye chosen from:
direct dyes chosen from dyes of formulae (V1) to (V52) below:
(V1)
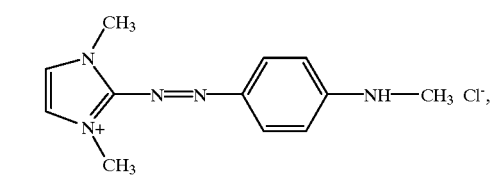
(V2)
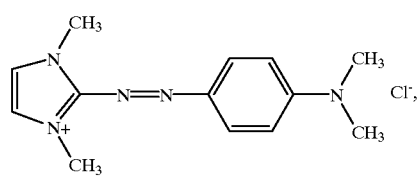
(V3)
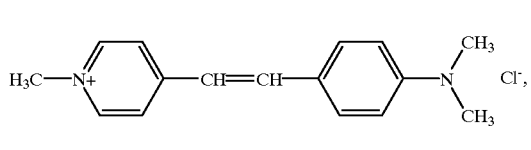
(V4)
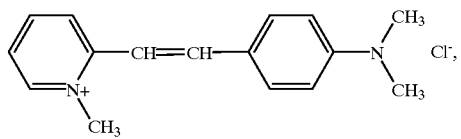
(V5)
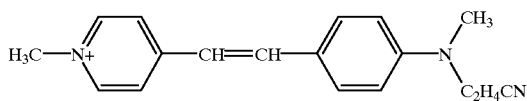
(V6)
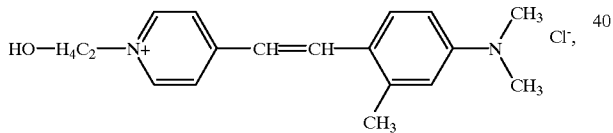
(V7)
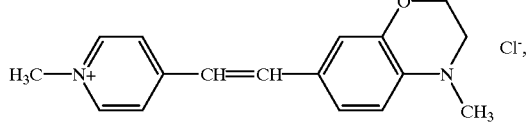
(V8)
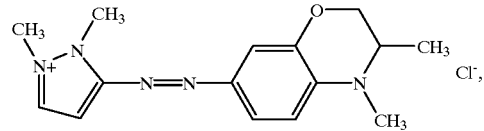
(V9)
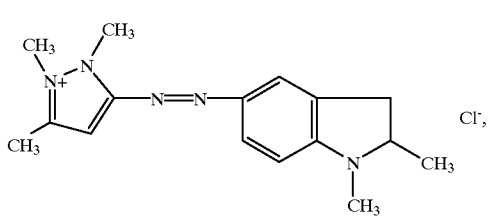
(V10)
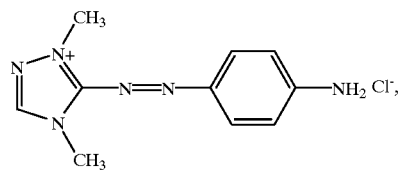
(V11)
(V12)
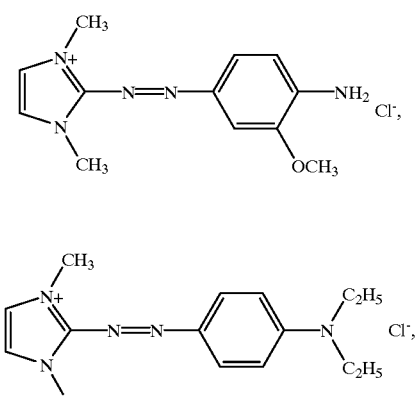
(V13)
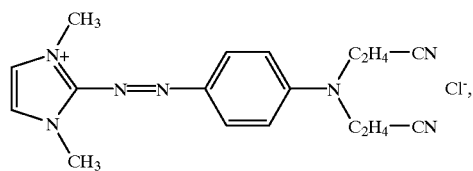
(V14)
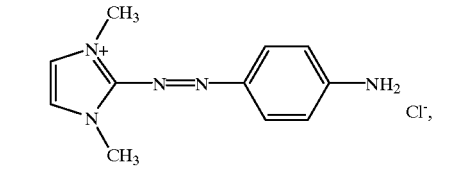
(V15)
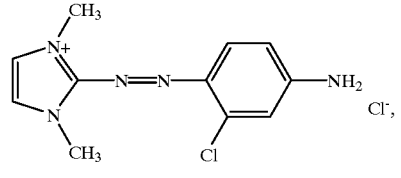
(V16)
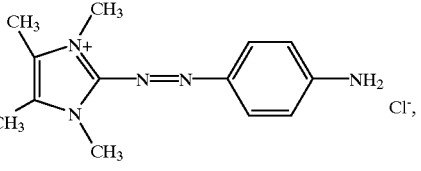
(V17)
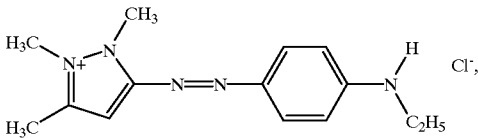

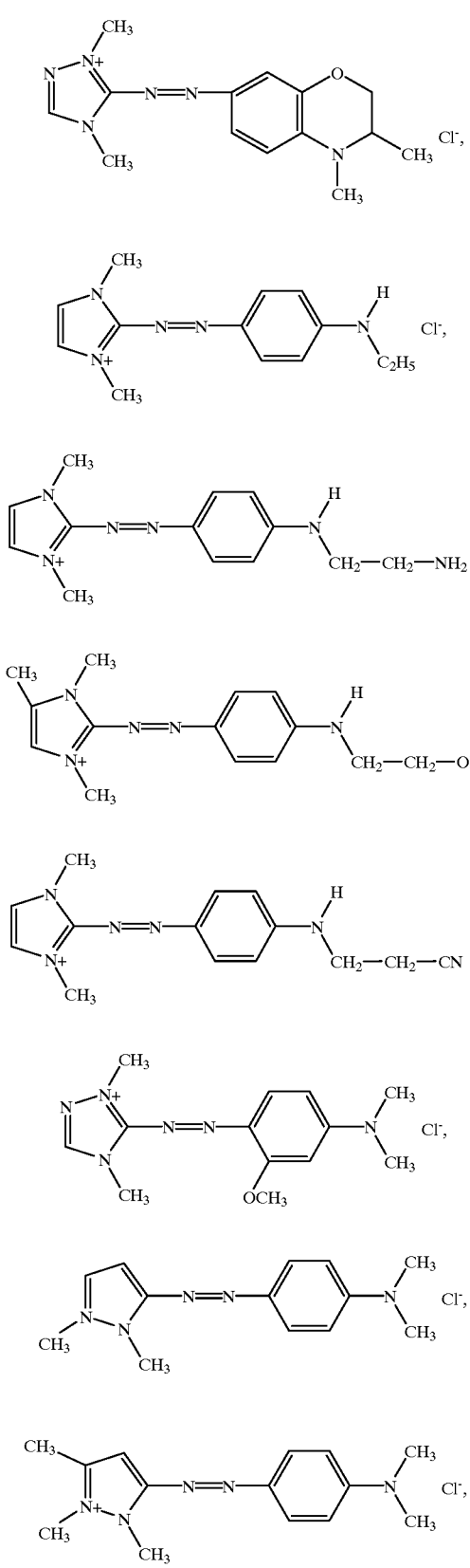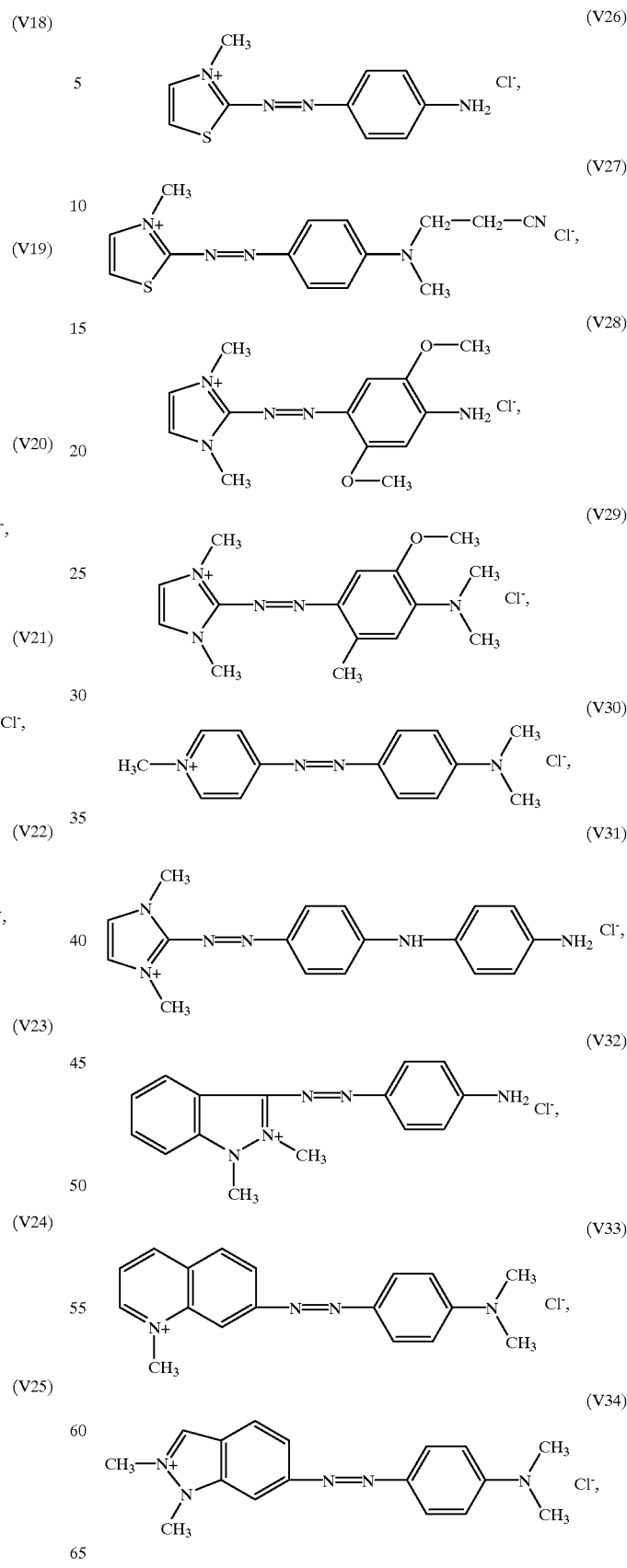

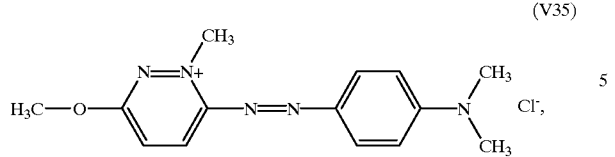
(V35)
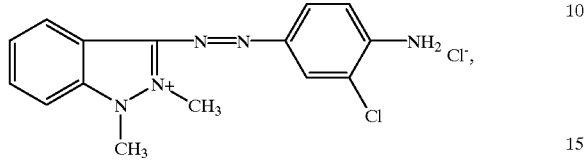
(V36)
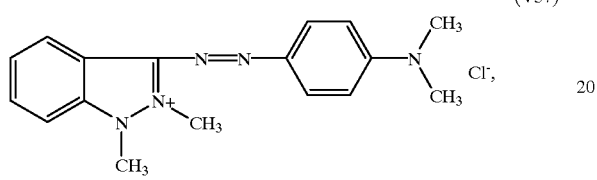
(V37)
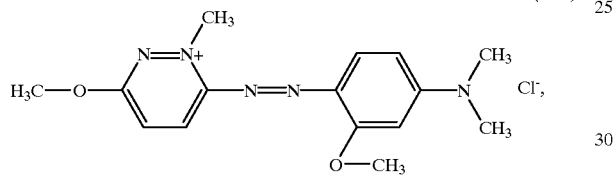
(V38)
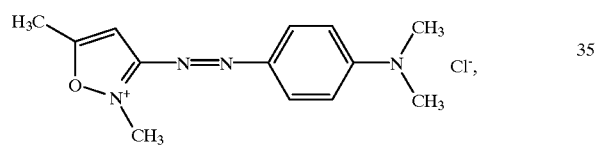
(V39)
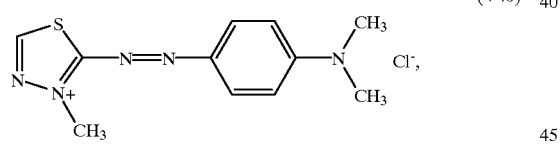
(V40)
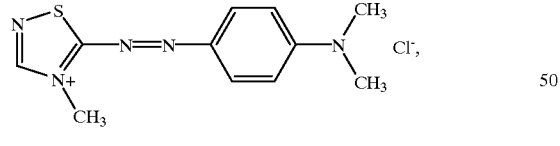
(V41)
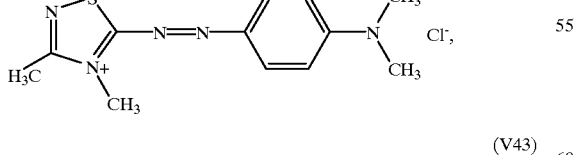
(V42)
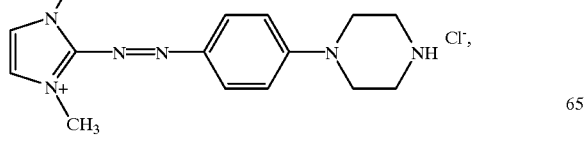
(V43)
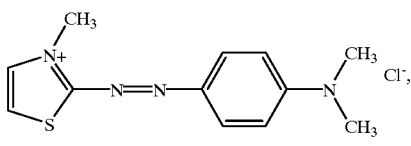
(V44)
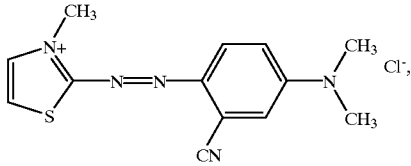
(V45)
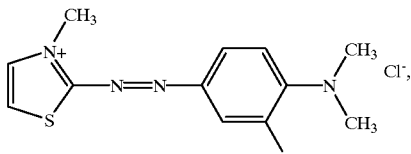
(V46)
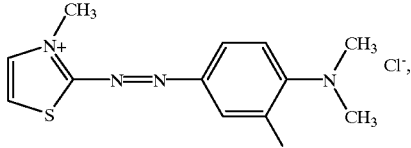
(V47)
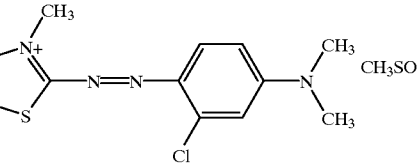
(V48)
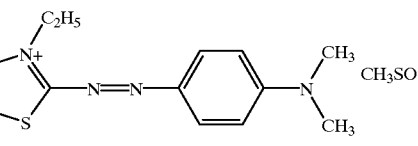
(V49)
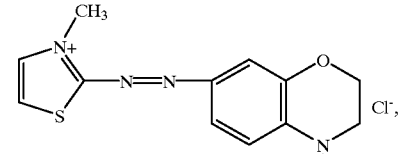
(V50)
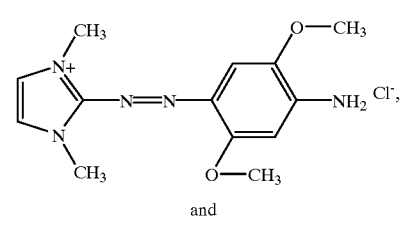
(V51)
and direct dyes chosen from dyes of formulae (VI1) to (VI12) below:

cationic direct dyes chosen from dyes of formulae (VII1) to (VII18) below:

(VII3)
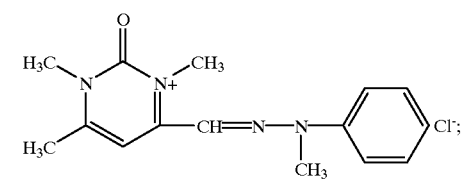
(VII4)
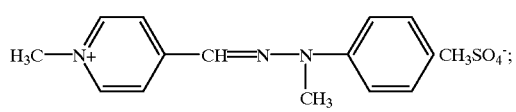
(VII5)
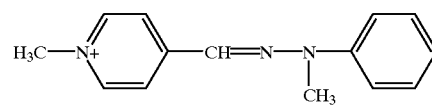
(VII6)
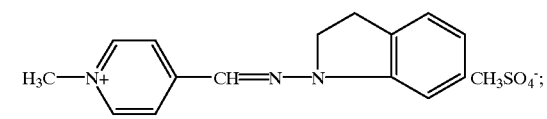
(VII7)
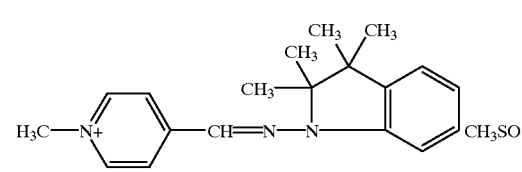
(VII8)
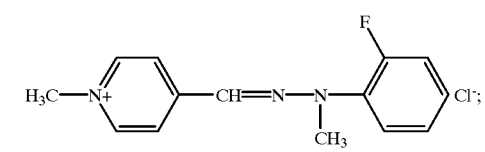
(VII9)
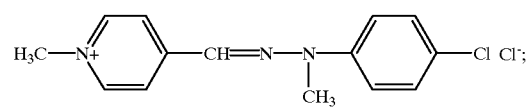
(VII10)
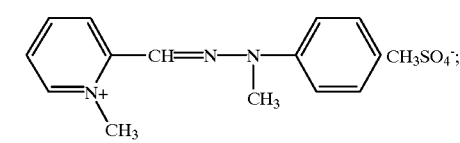
(VII11)
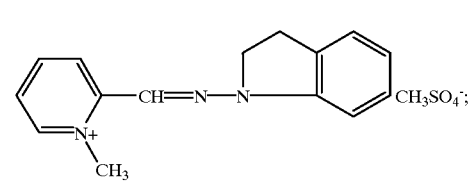
(VII12)
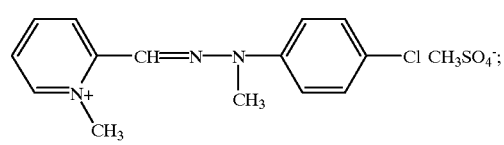
(VII13)
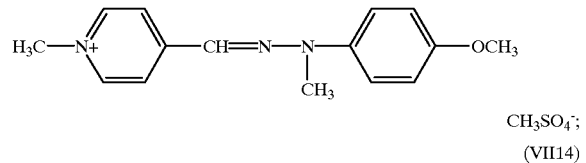
(VII14)
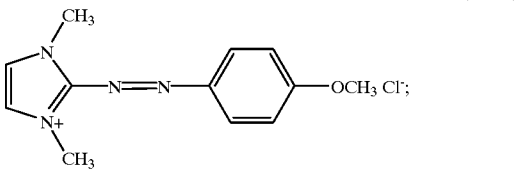
(VII15)
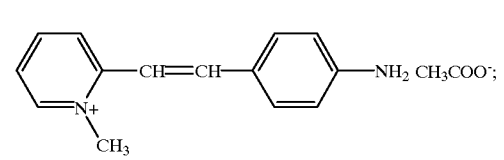
(VII16)
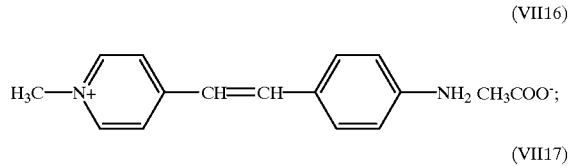
(VII17)
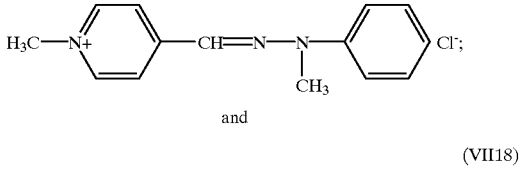
and
(VII18)
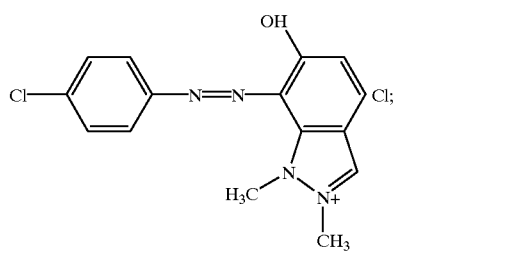
cationic direct dyes chosen from direct dyes of (VII'1) to (VII'3) below:
(VII'1)
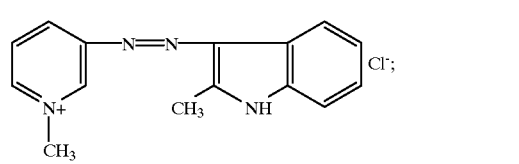

-continued

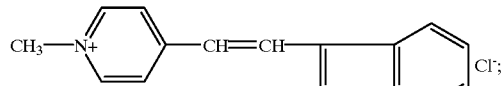

(VII'2)

and

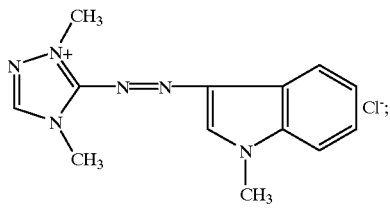

(VII'3)

at least one 2-electron oxidoreductase chosen from pyranose oxidases, glucose oxidases, glycerol oxidases, lactate oxidases, pyruvate oxidases and uricases, and at least one donor chosen from D-glucose, L-sorbose, D-xylose, glycerol, dihydroxyacetone, lactic acid and its salts, pyruvic acid and its salts, and uric acid and its salts.

45. A process for dyeing keratin fibers, comprising applying at least one ready-to-use dye composition for the oxidation dyeing of keratin fibers to said fibers and developing for a period sufficient to achieve a desired coloration, wherein said ready-to-use dye composition comprises:

at least one oxidation base chosen from: para-phenylenediamine and para-aminophenol;

at least one cationic direct dye chosen from:

(V1)

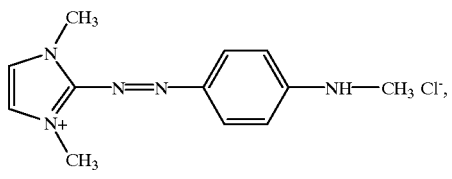

and (V4)

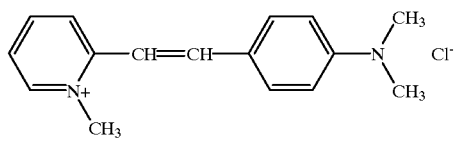

uricase; and
uric acid.

46. A process for dyeing keratin fibers, comprising:
separately storing a first composition,
separately storing a second composition,
thereafter mixing said first composition with said second composition,
applying said mixture to said fibers and developing for a period of time sufficient to achieve desired coloration,
wherein said first composition comprises:
at least one oxidation base chosen from:
para-phenylenediamines chosen from: para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and acid-addition salts thereof;

double bases chosen from: N,N'-bis(β-hydroxyethyl)-N,N'-bis(4'-aminophenyl)-1,3-diaminopropanol, N,N'-bis(β-hydroxyethyl)-N,N'-bis(4'-aminophenyl) ethylenediamine, N,N'-bis(4-aminophenyl) tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine, 1,8-bis(2,5-diaminophenoxy)-3,5-dioxaoctane, and acid-addition salts thereof;

para-aminophenols chosen from: para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and acid-addition salts thereof;

ortho-aminophenols chosen from: 2-aminophenol, 2-amino-5-methylphenol, 2-amino-6-methylphenol, 5-acetamido-2-aminophenol, and acid-addition salts thereof pyridine compounds chosen from: 2,5-diaminopyridine, 2-(4-methoxyphenyl)amino-3-amino-pyridine, 2,3-diamino-6-methoxypyridine, 2-(β-methoxy-ethyl) amino-3-amino-6-methoxypyridine, 3,4-diaminopyridine, and acid-addition salts thereof, pyrimidine compounds chosen from: 2,4,5,6-tetraamino-pyrimidine, 4-hydroxy-2,5,6-triaminopyrimidine, 2-hydroxy-4,5,6-triamino-pyrimidine, 2,4-dihydroxy-5,6-diaminopyrimidine, 2,5,6-tri-amino-pyrimidine, and acid-addition salts thereof, pyrazole compounds chosen from: 4,5-diamino-1-methyl-pyrazole, 3,4-diaminopyrazole, 4,5-diamino-1-(4'-chlorobenzyl)pyrazole, 4,5-diamino-1,3-dimethyl-pyrazole, 4,5-diamino-3-methyl-1-phenylpyrazole, 4,5-diamino-1-methyl-3-phenylpyrazole, 4-amino-1,3-di-methyl-5-hydrazinopyrazole, 1-benzyl-4,5-diamino-3-methyl-pyrazole, 4,5-diamino-3-tert-butyl-1-methyl-pyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1- ethyl-3-(4'-methoxyphenyl)pyrazole, 4,5-diamino-1-ethyl-3-hydroxymethylpyrazole, 4,5-diamino-3-hydroxymethyl-1-methyl-pyrazole, 4,5-diamino-3-hydroxymethyl-1-iso-propyl-pyrazole, 4,5-diamino-3-methyl-1-isopropyl-pyrazole, 4-amino-5-(2'-amino-ethyl)amino-1,3-dimethyl-pyrazole, 3,4,5-triamino-pyrazole, 1-methyl-3,4,5-tri-amino-pyrazole, 3,5-diamino-1-methyl-4-methylamino-pyrazole, 3,5-diamino-4-(β-hydroxyethyl)amino-1-methyl-pyrazole, and acid-addition salts thereof, pyrazolopyrimidine compounds chosen from:
pyrazolo[1,5-a]pyrimidine-3,7-diamine;
2,5-dimethylpyrazolo[1,5-a]pyrimidine-3,7-diamine;
pyrazolo[1,5-a]pyrimidine-3,5-diamine;
2,7-dimethylpyrazolo[1,5-a]pyrimidine-3,5-diamine;
3-aminopyrazolo[1,5-a]pyrimidin-7-ol;
3-aminopyrazolo[1,5-a]pyrimidin-5-ol;
2-(3-aminopyrazolo[1,5-a]pyrimidin-7-ylamino)ethanol;
2-(7-aminopyrazolo[1,5-a]pyrimidin-3-ylamino)ethanol;
2-[(3-aminopyrazolo[1,5-a]pyrimidin-7-yl)-(2-hydroxy-ethyl)amino]ethanol;
2-[(7-aminopyrazolo[1,5-a]pyrimidin-3-yl)-(2-hydroxy-ethyl)amino]ethanol;
5,6-dimethylpyrazolo[1,5-a]pyrimidine-3,7-diamine;
2,6-d imethylpyrazolo[1,5-a]pyrimidine-3,7-diamine;
2,5,N7,N7-tetramethylpyrazolo[1,5-a]pyrimidine-3,7-diamine;

and addition salts thereof and tautomeric forms thereof, when a tautomeric equilibrium exists;

at least one cationic direct dye chosen from:
direct dyes chosen from dyes of formulae (V1) to (V52) below:

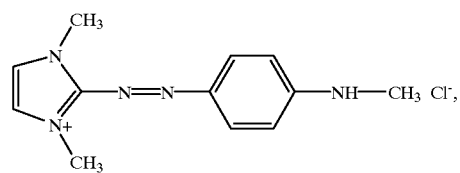
(V1)

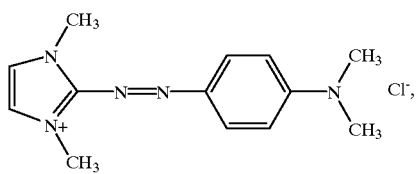
(V2)

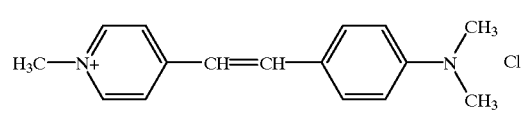
(V3)

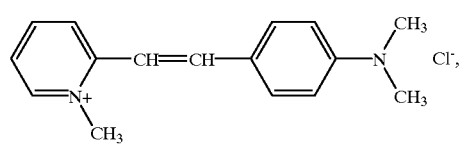
(V4)

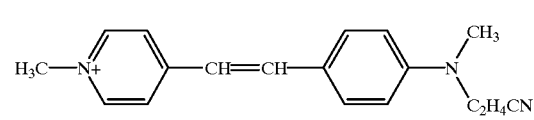
(V5)

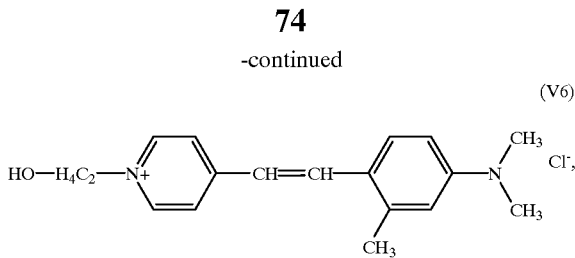
(V6)

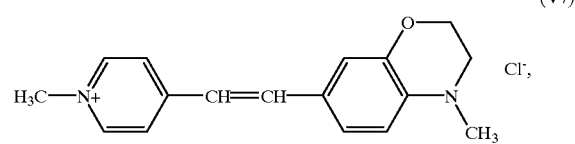
(V7)

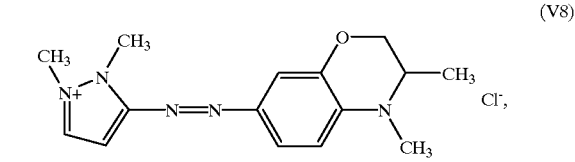
(V8)

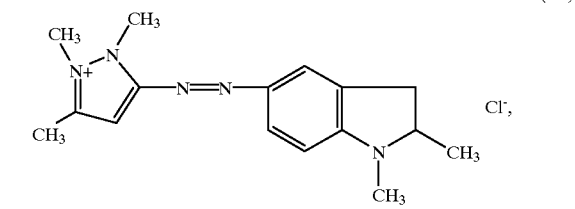
(V9)

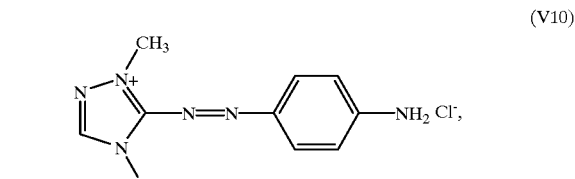
(V10)

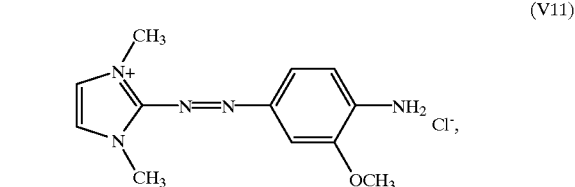
(V11)

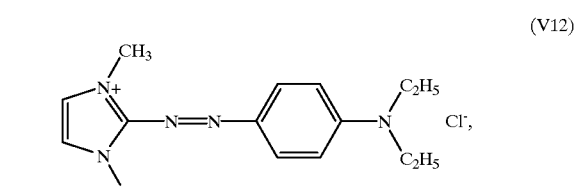
(V12)

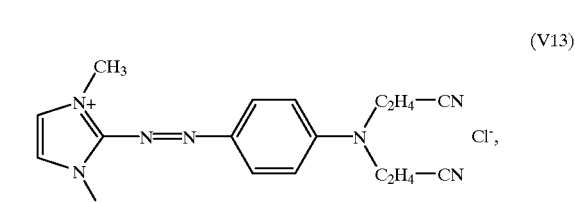
(V13)

-continued (V14) [structure]

(V15) [structure]

(V16) [structure]

(V17) [structure]

(V18) [structure]

(V19) [structure]

(V20) [structure]

(V21) [structure]

-continued (V22) [structure]

(V23) [structure]

(V24) [structure]

(V25) [structure]

(V26) [structure]

(V27) [structure]

(V28) [structure]

(V29) [structure]

(V30) [structure]

-continued
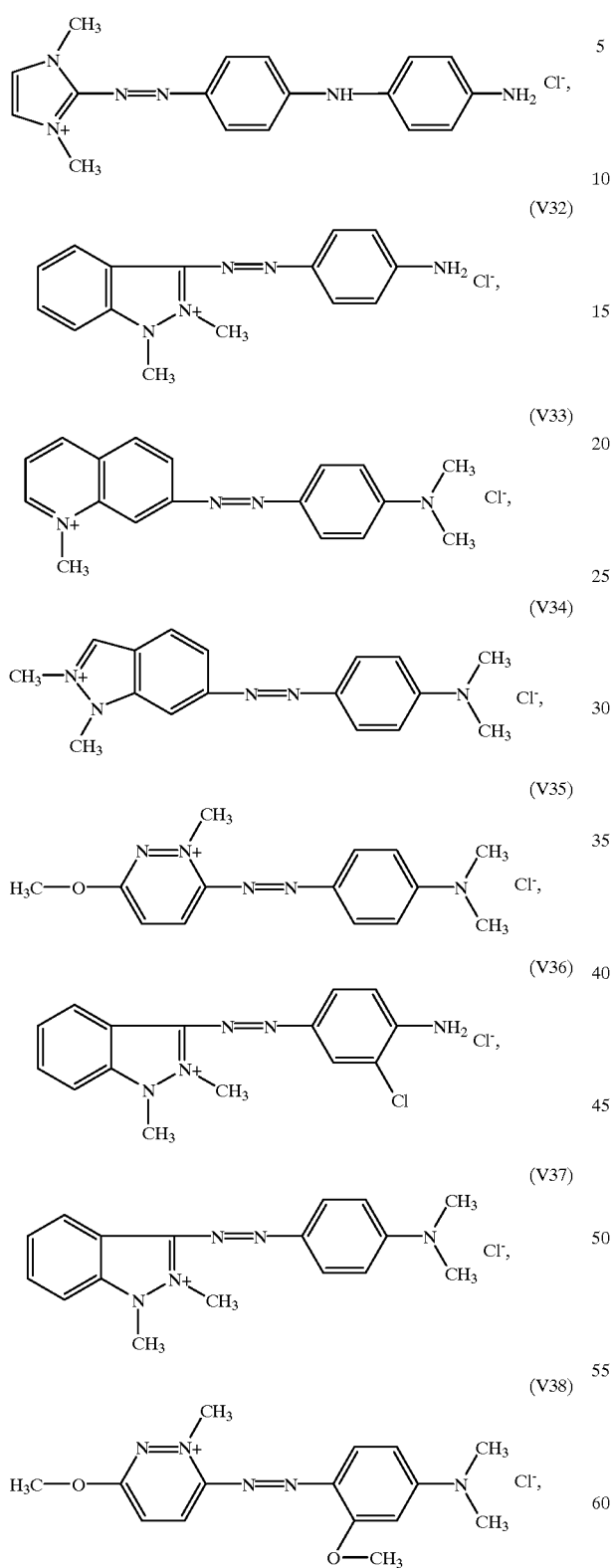
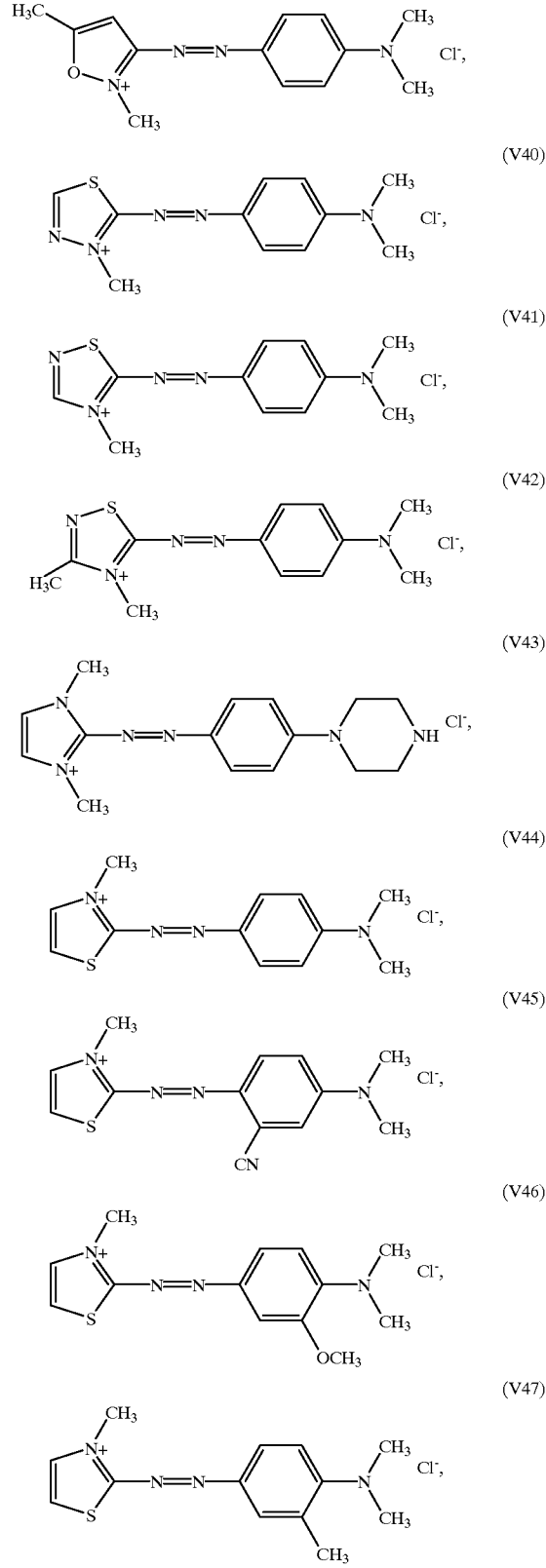

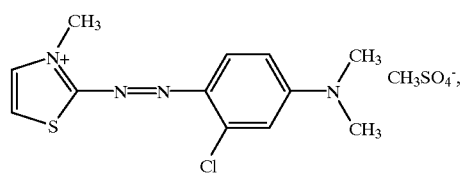 (V48)
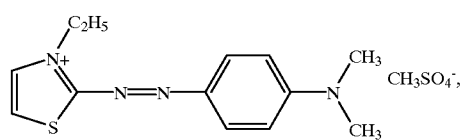 (V49)
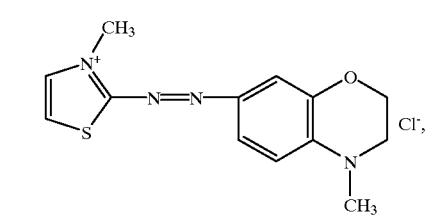 (V50)
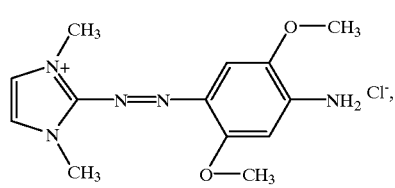 (V51)
and
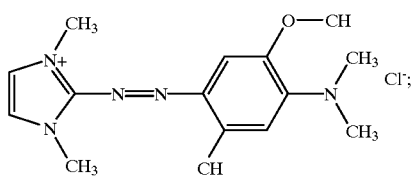 (V52)
direct dyes chosen from dyes of formulae (VI1) to (VI12) below:
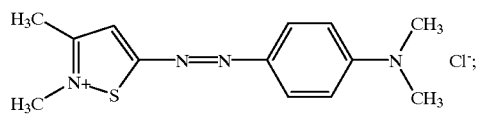 (VI1)
 (VI2)
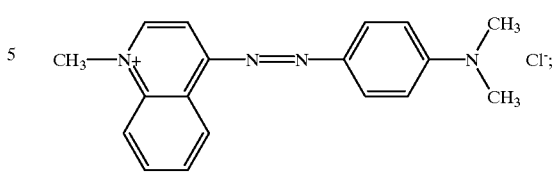 (VI3)
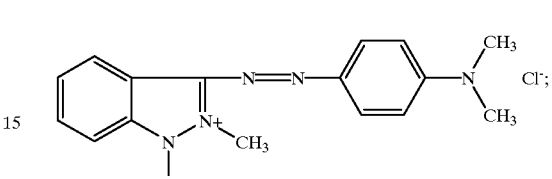 (VI4)
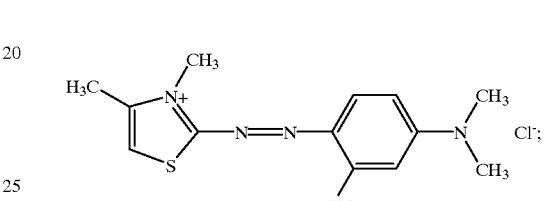 (VI5)
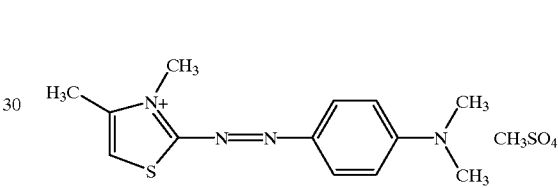 (VI6)
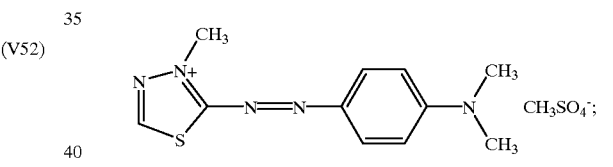 (VI7)
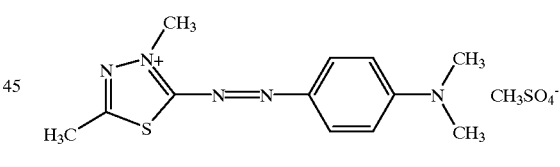 (VI8)
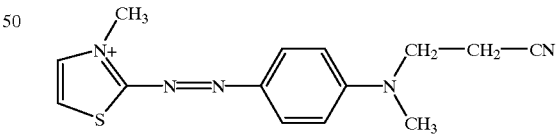 (VI9)
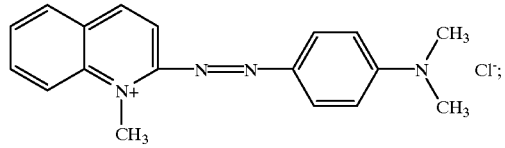
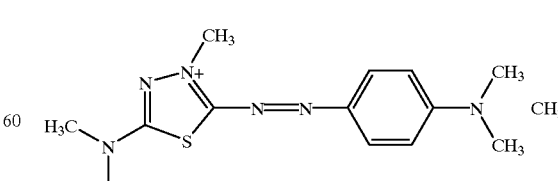 (VI10)

(VI11)
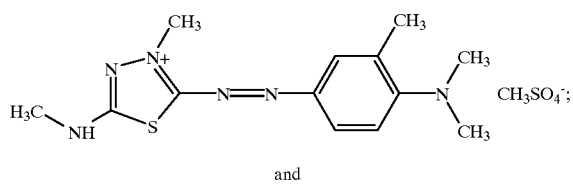
CH₃SO₄⁻;
and
(VI12)
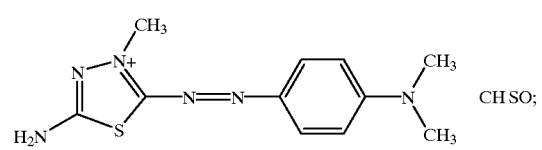
CH₃SO₄⁻;
cationic direct dyes chosen from dyes of formulae (VII1) to (VII18) below:
(VII1)
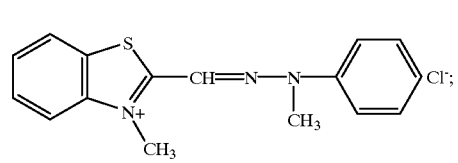
Cl⁻;
(VII2)
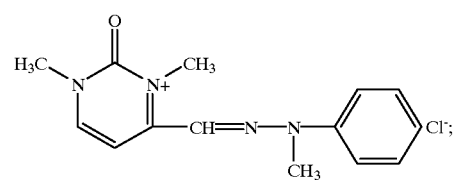
Cl⁻;
(VII3)
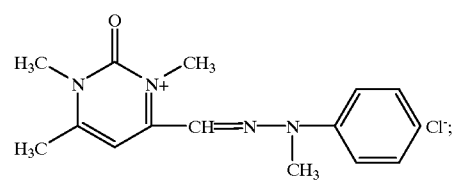
Cl⁻;
(VII4)
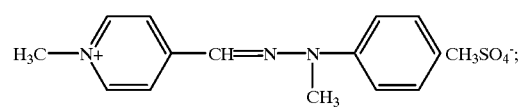
CH₃SO₄⁻;
(VII5)
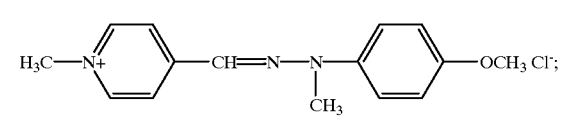
Cl⁻;
(VII6)
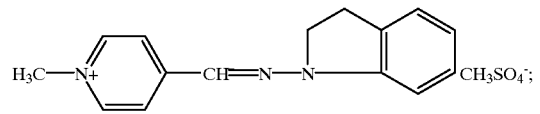
CH₃SO₄⁻;
(VII7)
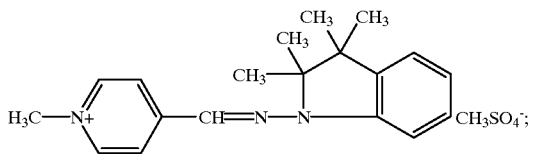
CH₃SO₄⁻;
(VII8)
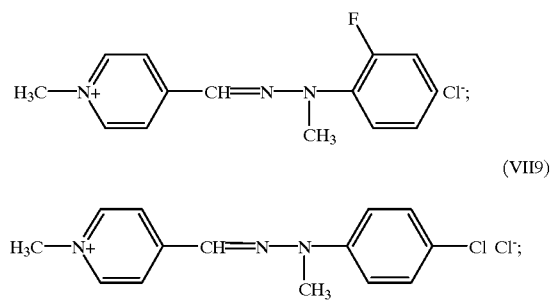
Cl⁻;
(VII9)
Cl⁻;
(VII10)
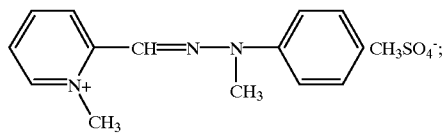
CH₃SO₄⁻;
(VII11)
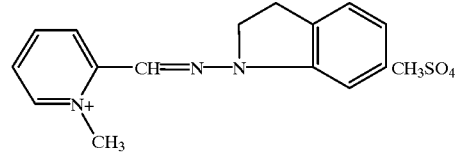
CH₃SO₄⁻;
(VII12)
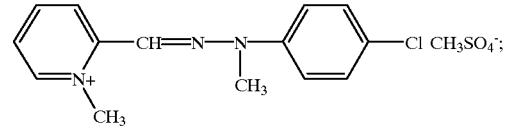
Cl CH₃SO₄⁻;
(VII13)
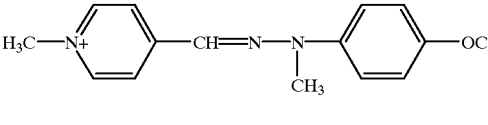
CH₃SO₄⁻;
(VII14)
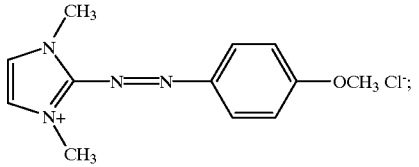
Cl⁻;
(VII15)
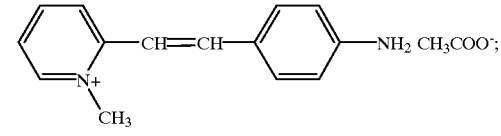
NH₂ CH₃COO⁻;

-continued (VII16)
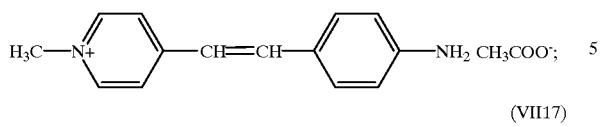

(VII17)
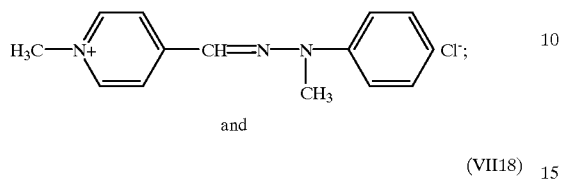
and (VII18)
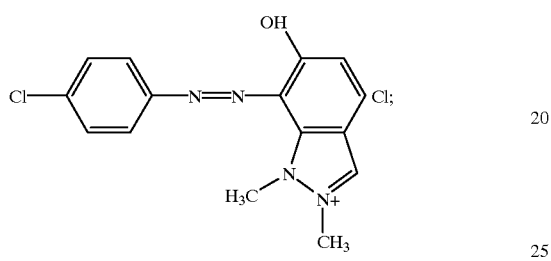

cationic direct dyes chosen from direct dyes of (VII'1) to (VII'3) below:

(VII'1)
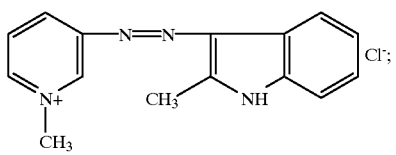

(VII'2)
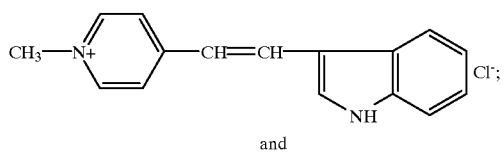
and (VII'3)
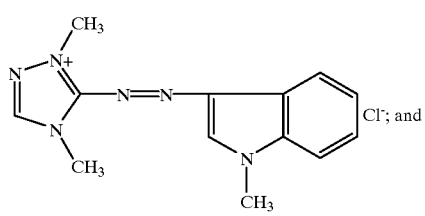

wherein said second composition comprises:
at least one 2-electron oxidoreductase chosen from pyranose oxidases, glucose oxidases, glycerol oxidases, lactate oxidases, pyruvate oxidases and uricases, and
at least one donor chosen from D-glucose, L-sorbose, D-xylose, glycerol, dihydroxyacetone, lactic acid and its salts, pyruvic acid and its salts, and uric acid and its salts.

47. A process for dyeing keratin fibers, comprising:
separately storing a first composition,
separately storing a second composition,
thereafter mixing said first composition with said second composition,
applying said mixture to said fibers and developing for a period of time sufficient to achieve desired coloration,
wherein said first composition comprises:
at least one oxidation base chosen from: para-phenylenediamine and para-aminophenol;
at least one cationic direct dye chosen from:

(V1)
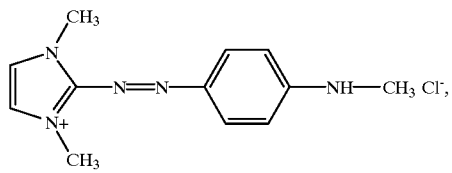
and (V4)
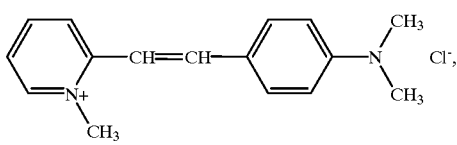

wherein said second composition comprises:
uricase; and
uric acid.

48. A multi-compartment dyeing kit, comprising at least two separate compartments wherein a first compartment contains a first composition and a second compartment contains a second composition,
wherein said first composition comprises:
at least one oxidation base chosen from:
para-phenylenediamines chosen from: para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and acid-addition salts thereof;
double bases chosen from: N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'- bis(4-methylaminophenyl)tetramethylenediamine, N,N'-bis(ethyl)-N,N'-bis(4'-amino-3'-methylphenyl) ethylenediamine, 1,8-bis(2,5-diaminophenoxy)-3,5-dioxaoctane, and acid-addition salts thereof;

para-aminophenols chosen from: para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and acid-addition salts thereof;

ortho-aminophenols chosen from: 2-aminophenol, 2-amino-5-methylphenol, 2-amino-6-methylphenol, 5-acetamido-2-aminophenol, and acid-addition salts thereof pyridine compounds chosen from: 2,5-diaminopyridine, 2-(4-methoxyphenyl)amino-3-amino-pyridine, 2,3-diamino-6-methoxypyridine, 2-(β-methoxy-ethyl) amino-3-amino-6-methoxypyridine, 3,4-diaminopyridine, and acid-addition salts thereof, pyrimidine compounds chosen from: 2,4,5,6-tetraamino-pyrimidine, 4-hydroxy-2,5,6-triaminopyrimidine, 2-hydroxy-4,5,6-triamino-pyrimidine, 2,4-dihydroxy-5,6-diaminopyrimidine, 2,5,6-tri-amino-pyrimidine, and acid-addition salts thereof, pyrazole compounds chosen from: 4,5-diamino-1-methyl-pyrazole, 3,4-diaminopyrazole, 4,5-diamino-1-(4'-chlorobenzyl)pyrazole, 4,5-diamino-1,3-dimethyl-pyrazole, 4,5-diamino-3-methyl-1-phenylpyrazole, 4,5-diamino-1-methyl-3-phenylpyrazole, 4-amino-1,3-di-methyl-5-hydrazinopyrazole, 1-benzyl-4,5-diamino-3-methyl-pyrazole, 4,5-diamino-3-tert-butyl-1-methyl-pyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methyl-pyrazole, 4,5-diamino-3-hydroxymethyl-1-iso-propyl-pyrazole, 4,5-diamino-3-methyl-1-isopropyl-pyrazole, 4-amino-5-(2'-amino-ethyl)amino-1,3-dimethyl-pyrazole, 3,4,5-triamino-pyrazole, 1-methyl-3,4,5-tri-amino-pyrazole, 3,5-diamino-1-methyl-4-methylamino-pyrazole, 3,5-diamino-4-(β-hydroxyethyl)amino-1-methyl-pyrazole, and acid-addition salts thereof, pyrazolopyrimidine compounds chosen from:
pyrazolo[1,5-a]pyrimidine-3,7-diamine;
2,5-dimethylpyrazolo[1,5-a]pyrimidine-3,7-diamine;
pyrazolo[1,5-a]pyrimidine-3,5-diamine;
2,7-dimethylpyrazolo[1,5-a]pyrimidine-3,5-diamine;
3-aminopyrazolo[1,5-a]pyrimidin-7-ol;
3-aminopyrazolo[1,5-a]pyrimidin-5-ol;
2-(3-aminopyrazolo[1,5-a]pyrimidin-7-ylamino)ethanol;
2-(7-aminopyrazolo[1,5-a]pyrimidin-3-ylamino)ethanol;
2-[(3-aminopyrazolo[1,5-a]pyrimidin-7-yl)-(2-hydroxy-ethyl)amino]ethanol;
2-[(7-aminopyrazolo[1,5-a]pyrimidin-3-yl)-(2-hydroxy-ethyl)amino]ethanol;
5,6-dimethylpyrazolo[1,5-a]pyrimidine-3,7-diamine;
2,6-dimethylpyrazolo[1,5-a]pyrimidine-3,7-diamine;
2,5,N7,N7-tetramethylpyrazolo[1,5-a]pyrimidine-3,7-diamine;
and addition salts thereof and tautomeric forms thereof, when a tautomeric equilibrium exists;

at least one cationic direct dye chosen from:

direct dyes chosen from dyes of formulae (V1) to (V52) below:

(V1)
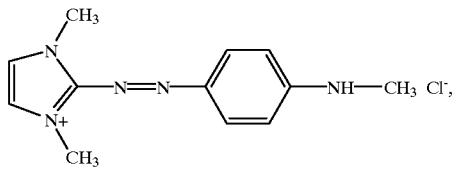

(V2)
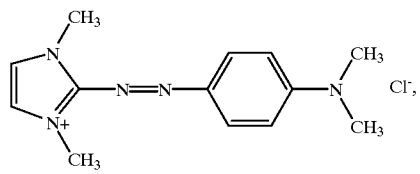

(V3)
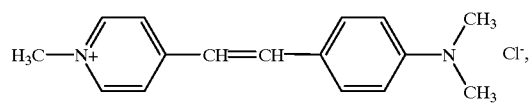

(V4)
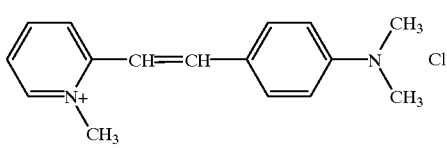

(V5)
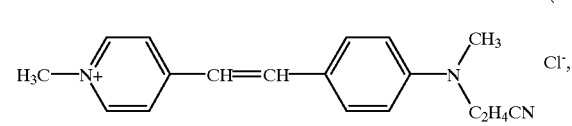

(V6)
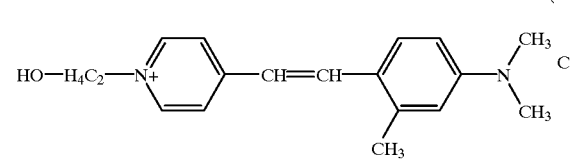

(V7)
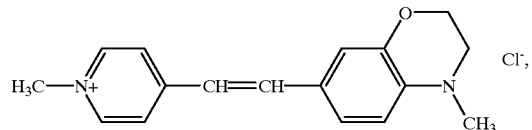

(V8)
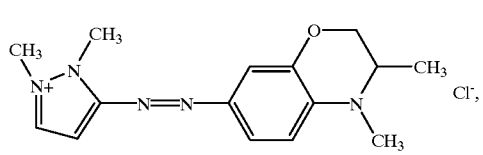

(V9)
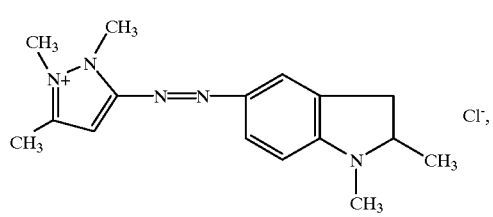

(V10) – (V25): chemical structures only.

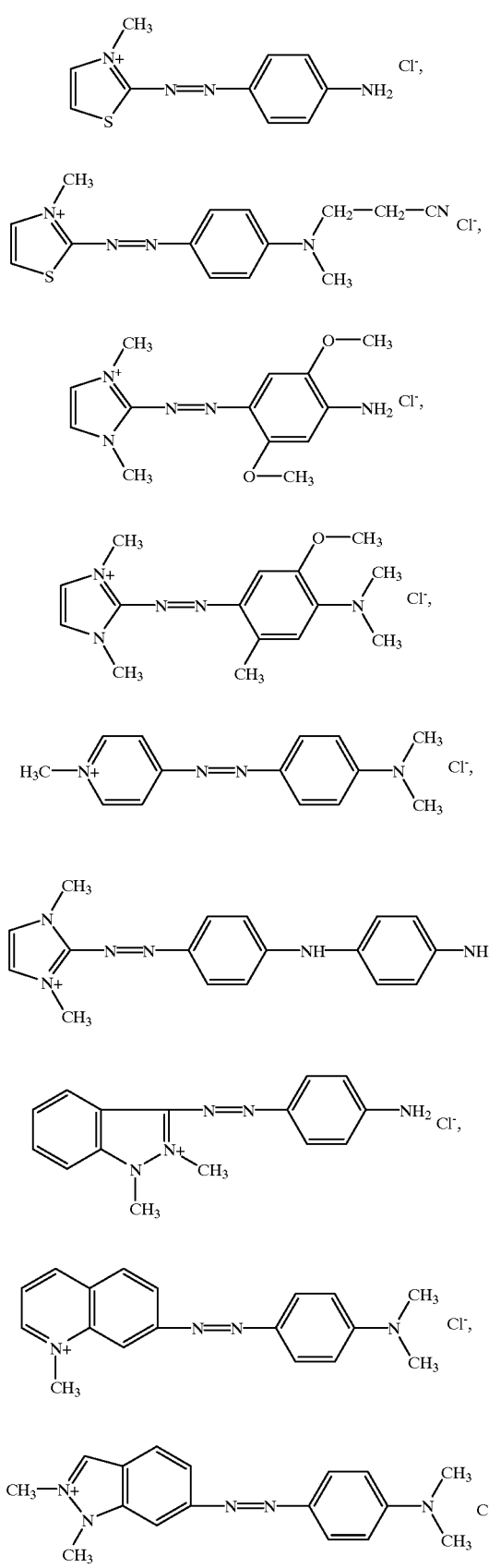
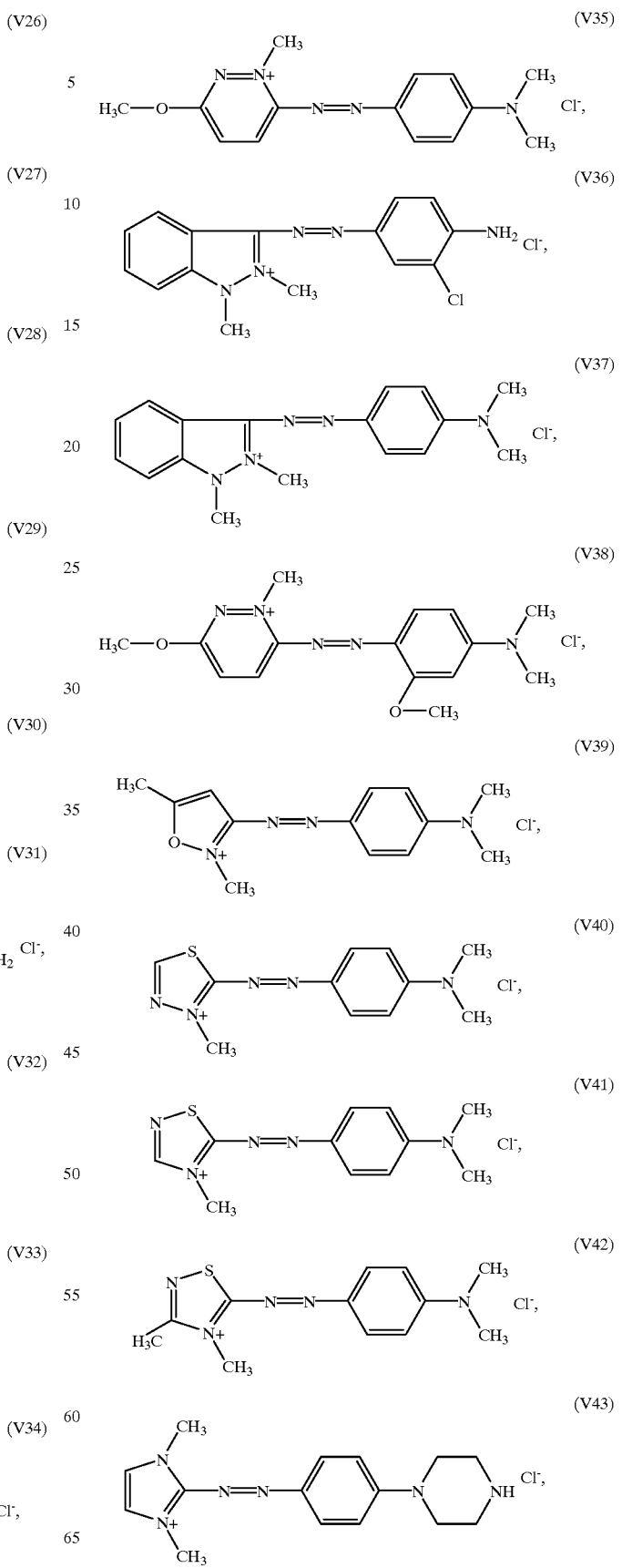

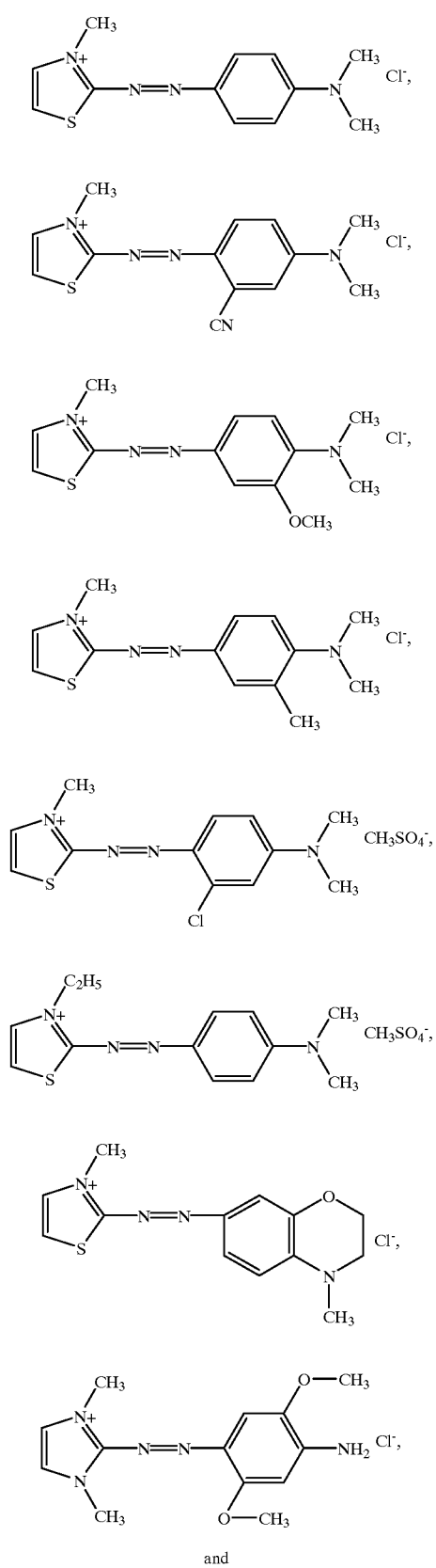
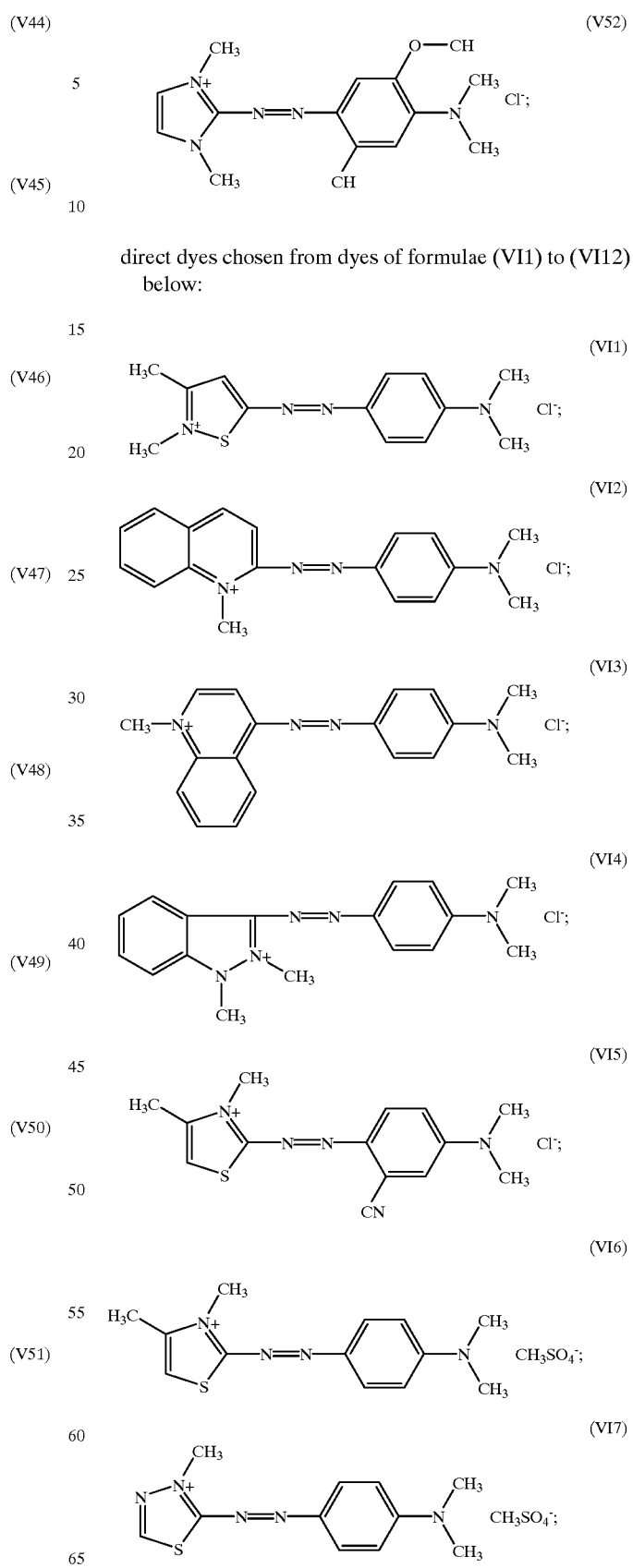
direct dyes chosen from dyes of formulae (VI1) to (VI12) below:

(VI8)
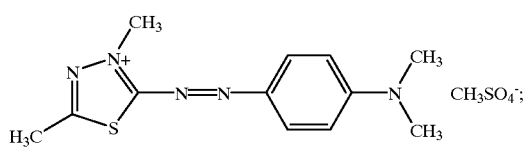
(VI9)
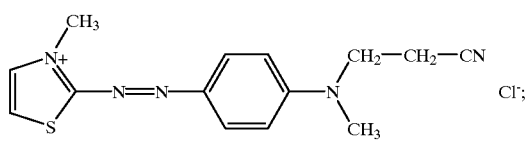
(VI10)
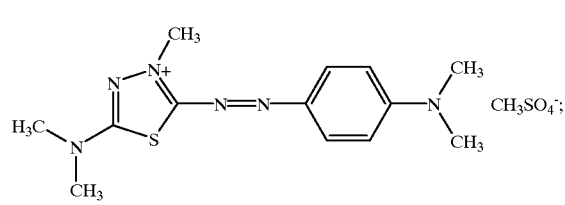
(VI11)
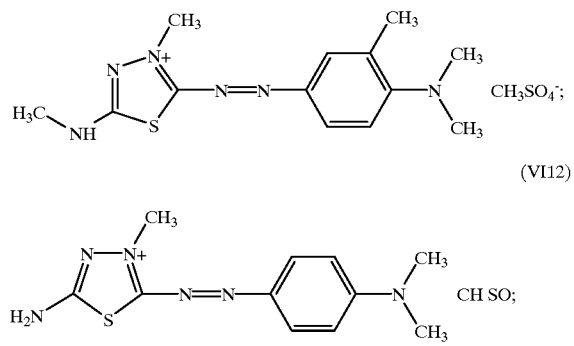
(VI12)
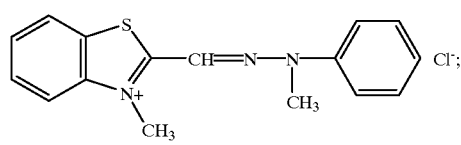
and
cationic direct dyes chosen from dyes of formulae (VII1) to (VII18) below:
(VII1)
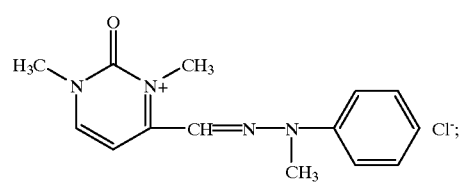
(VII2)
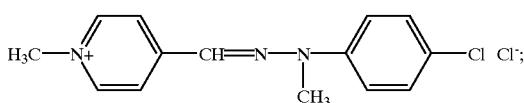
(VII3)
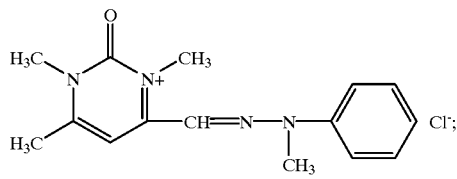
(VII4)
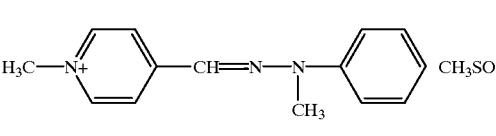
(VII5)
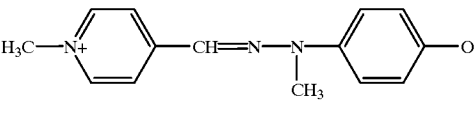
(VII6)
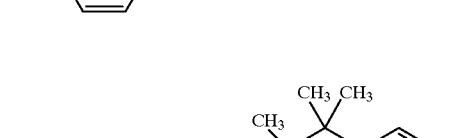
(VII7)
(VII8)
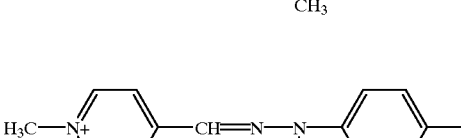
(VII9)
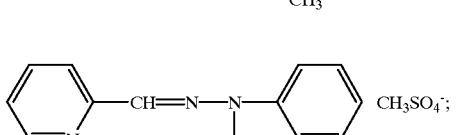
(VII10)
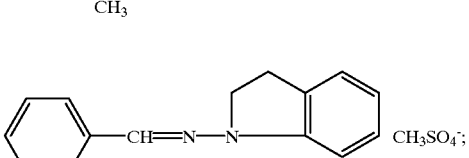
(VII11)

-continued (VII12)
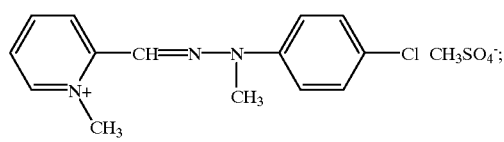

(VII13)
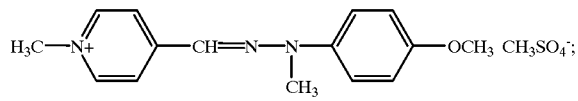

(VII14)
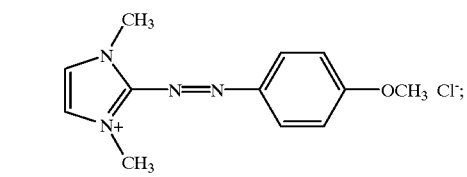

(VII15)
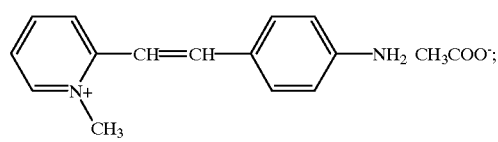

(VII16)
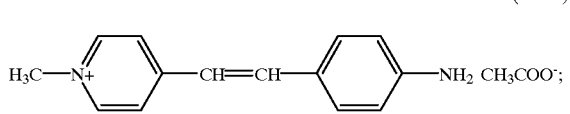

(VII17)
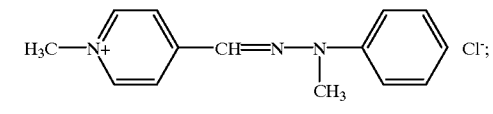

and (VII18)
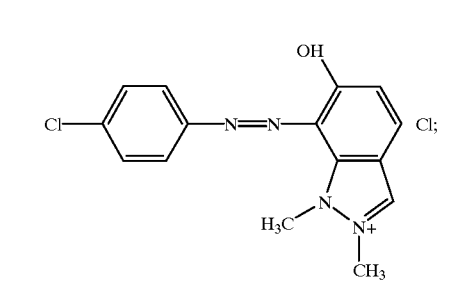

cationic direct dyes chosen from direct dyes of (VII'1) to (VII'3) below:

(VII'1)
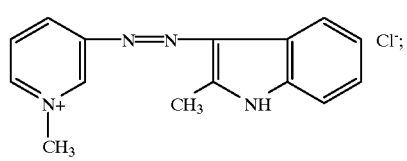

-continued (VII'2)
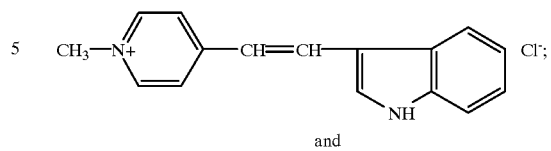

and (VII'3)
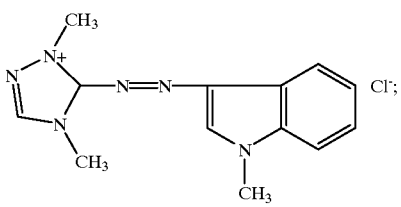

wherein said second composition comprises:
at least one 2-electron oxidoreductase chosen from pyranose oxidases, glucose oxidases, glycerol oxidases, lactate oxidases, pyruvate oxidases and uricases, and
at least one donor chosen from D-glucose, L-sorbose, D-xylose, glycerol, dihydroxyacetone, lactic acid and its salts, pyruvic acid and its salts, and uric acid and its salts.

49. A multi-compartment dyeing kit, comprising at least two separate compartments wherein a first compartment contains a first composition and a second compartment contains a second composition,
wherein said first composition comprises:
at least one oxidation base chosen from: para-phenylenediamine and para-aminophenol;
at least one cationic direct dye chosen from:

(V1)
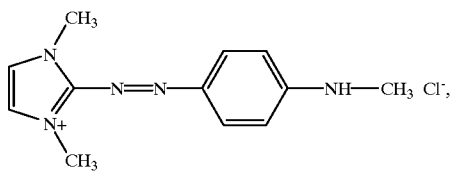

and (V4)
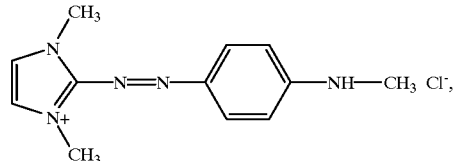

wherein said second composition comprises:
uricase; and
uric acid.

50. A process for dyeing keratin fibers, comprising applying at least one ready-to-use dye composition for the oxidation dyeing of keratin fibers to said fibers and developing for a period sufficient to achieve a desired coloration, wherein said ready-to-use dye composition comprises:
at least one oxidation base,
at least one cationic direct dye,
at least one enzyme chosen from 2-electron oxidoreductases, and
at least one donor for said at least one enzyme,
wherein said at least one caflonic direct dye is chosen from a) compounds of formula (V) below:

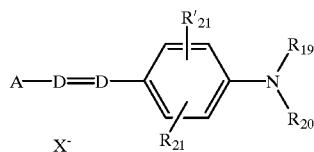
(V)

in which:

D is chosen from a nitrogen atom and a —CH group, $R_{19}$ and $R_{20}$, which may be identical or different, are chosen from a hydrogen atom; $C_1$–$C_4$ alkyl radicals; and a 4'-aminophenyl radical; or form, with a carbon atom of the benzene ring of formula (V), a heterocycle, $R_{21}$ and $R'_{21}$, which may be identical or different, are chosen from a hydrogen atom, halogen atoms, a cyano group, $C_1$–$C_4$ alkoxy radicals and acetyloxy radicals, $X^-$ is chosen from anions, A is a group chosen from structures A1 to A19 below, $A_1$
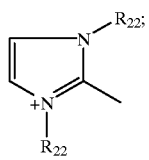

$A_2$
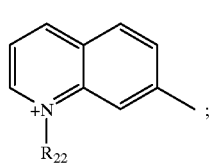

$A_3$
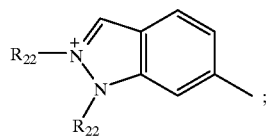

$A_4$
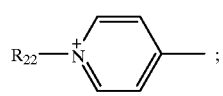

$A_5$
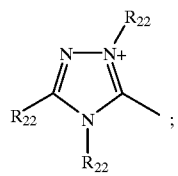

$A_6$
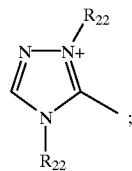

-continued $A_7$
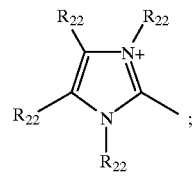

$A_8$
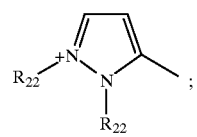

$A_9$
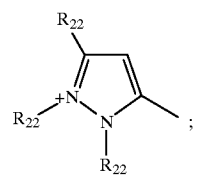

$A_{10}$
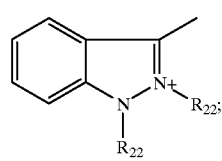

$A_{11}$
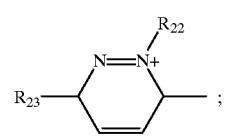

$A_{12}$
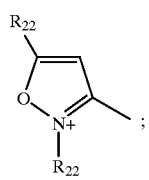

$A_{13}$
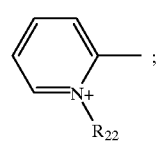

$A_{14}$
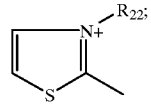

$A_{15}$
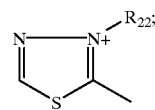

$A_{16}$
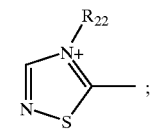

-continued

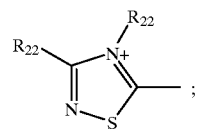   A₁₇

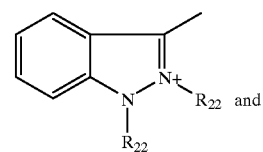   A₁₈ and

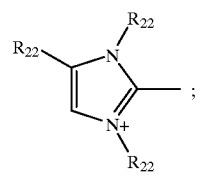   A₁₉ in which:

R₂₂ is chosen from C₁–C₄ alkyl radicals which can be substituted with a hydroxyl radical, and R₂₃ is chosen from C₁–C₄ alkoxy radicals;

b) compounds of formula (VI) below:

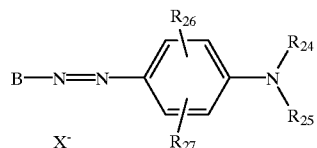   (VI)

in which:

R₂₄ is chosen from a hydrogen atom and C₁–C₄ alkyl radicals,

R₂₅ is chosen from a hydrogen atom, alkyl radicals, and a 4'-aminophenyl radical or forms, with R₂₄, a heterocycle, R₂₆ and R₂₇, which may be identical or different, are chosen from a hydrogen atom, halogen atoms, C₁–C₄ alkyl radicals, C₁–C₄ alkoxy radicals and a —CN radical, X⁻ is chosen from anions, B is a group chosen from structures B1 to B9 below:

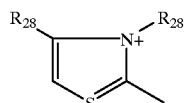   B1

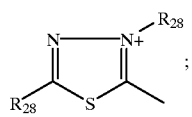   B2

-continued

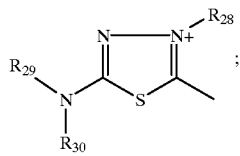   B3

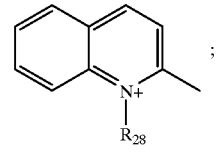   B4

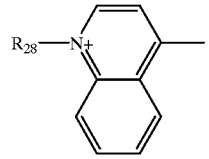   B5

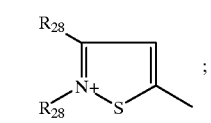   B6

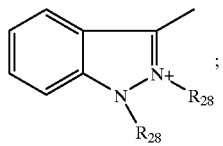   B7

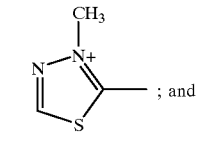   B8

; and

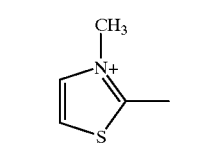   B9 in which:

R₂₈ is chosen from C₁–C₄ alkyl radicals,

R₂₉ and R₃₀, which may be identical or different, are chosen from a hydrogen atom and C₁–C₄ alkyl radicals;

c) compounds of formulae (VII) and (VII') below:

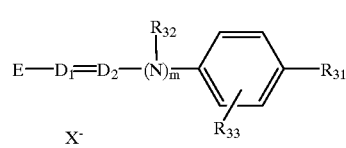   (VII)

-continued (VII')

[Structure: indole with E—D₁=D₂ substituent, R₃₅, R₃₄, X⁻]

in which:

R₃₁ is chosen from a hydrogen atom, $C_1$–$C_4$ alkoxy radicals, halogen atoms and an amino radical, R₃₂ is chosen from a hydrogen atom and $C_1C_4$ alkyl radicals or forms, with a carbon atom of the benzene ring, a heterocycle which is optionally oxygenated or substituted with at least one $C_1$–$C_4$ alkyl radical, R₃₃ is chosen from a hydrogen atom and halogen atoms, R₃₄ and R₃₅, which may be identical or different, are chosen from a hydrogen atom and $C_1$–$C_4$ alkyl radicals, D₁ and D₂, which may be identical or different, are chosen from a nitrogen atom and a —CH group, m=0 or 1, wherein, when R₃₁, is an unsubstituted amino group, D₁ and D₂ are both a —CH group and m=0, X⁻ is chosen from anions, E is a group chosen from structures E1 to E8 below:

E1
[Structure: R₃₆—N⁺ pyridinium]

E2
[Structure: pyridinium with R₃₆]

E3
[Structure: pyrimidinone with R₃₆, R₃₆]

E4
[Structure: pyrimidinone with R₃₆, R₃₆, R₃₆]

E5
[Structure: hydroxyindazolium with OH, R₃₆, R₃₆]

E6
[Structure: benzothiazolium with R₃₆]

E7
[Structure: 3-methylpyridinium with R₃₆]

E8
[Structure: triazolium with R₃₆, R₃₆]

in which:

R₃₆ is chosen from $C_1$–$C_4$ alkyl radicals; and when m=0 and when D₁, is a nitrogen atom, E can also be chosen from a group of structure E9 below:

E9
[Structure: imidazolium with R₃₆, R₃₆]

in which:

R₃₆ is chosen from $C_1$–$C_4$ alkyl radicals, and d) the compound of formula (V43) below (V43)

[Structure: dimethylimidazolium-azo-phenyl-piperazine, Cl⁻]

51. A process for dyeing keratin fibers, comprising:

separately storing a first composition, separately storing a second composition, thereafter mixing said first composition with said second composition, applying said mixture to said fibers and developing for a period of time sufficient to achieve a desired coloration, wherein said first composition comprises:

at least one oxidation base, and at least one cabonic direct dye chosen from a) compounds of formula (V) below;

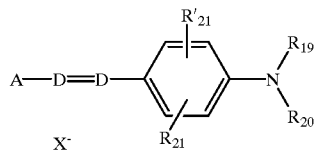

(V)

in which:

D is chosen from a nitrogen atom and a —CH group, $R_{19}$ and $R_{20}$, which may be identical or different, are chosen from a hydrogen atom; $C_1$–$C_4$ alkyl radicals; and a 4'-aminophenyl radical; or form, with a carbon atom of the benzene ring of formula (V), a heterocycle, $R_{21}$ and $R'_{21}$, which may be identical or different, are chosen from a hydrogen atom, halogen atoms, a cyano group, $C_1$–$C_4$ alkoxy radicals and acetyloxy radicals, $X^-$ is chosen from anions, A is a group chosen from structures A1 to A19 below,

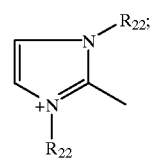

$A_1$

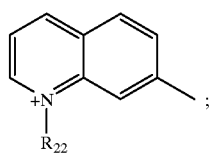

$A_2$

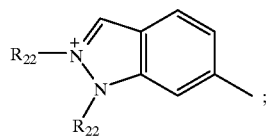

$A_3$

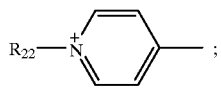

$A_4$

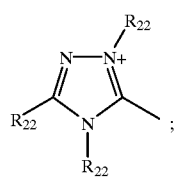

$A_5$

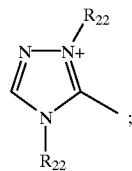

$A_6$

-continued

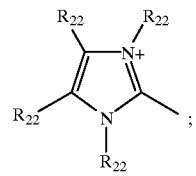

$A_7$

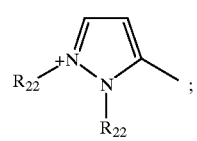

$A_8$

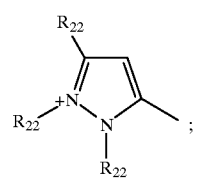

$A_9$

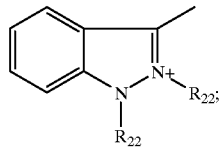

$A_{10}$

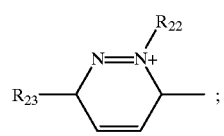

$A_{11}$

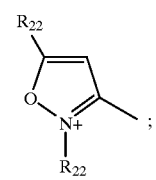

$A_{12}$

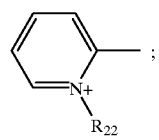

$A_{13}$

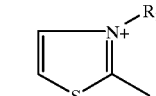

$A_{14}$

$A_{15}$

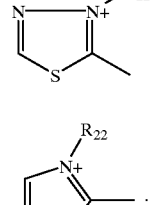

$A_{16}$

-continued

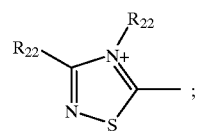

A₁₇

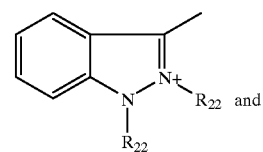

A₁₈

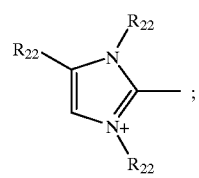

A₁₉ in which:

R₂₂ is chosen from $C_1$–$C_4$ alkyl radicals which can be substituted with a hydroxyl radical, and R₂₃ is chosen from $C_1$–$C_4$ alkoxy radicals;

b) compounds of formula (VI) below:

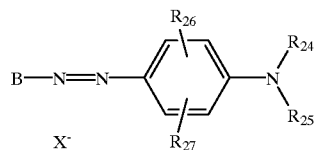

(VI)

in which:

R₂₄ is chosen from a hydrogen atom and $C_1$–$C_4$ alkyl radicals,

R₂₆ is chosen from a hydrogen atom, alkyl radicals, and a 4'-aminophenyl radical or forms, with R₂₄, a heterocycle, R₂₆ and R₂₇, which may be identical or different, are chosen from a hydrogen atom, halogen atoms, $C_1$–$C_4$ alkyl radicals, $C_1$–$C_4$ alkoxy radicals and a —CN radical, X⁻ is chosen from anions, B is a group chosen from structures B1 to B9 below:

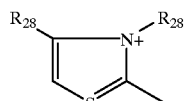

B1

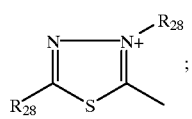

B2

-continued

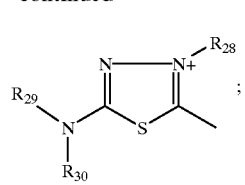

B3

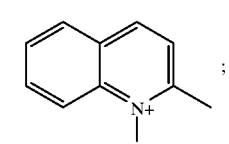

B4

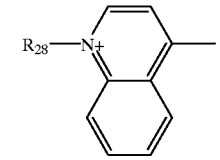

B5

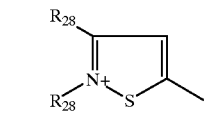

B6

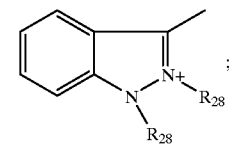

B7

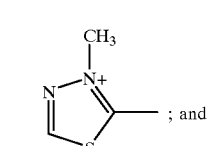

B8

; and

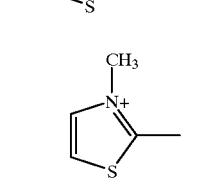

B9 in which:

R₂₈ is chosen from $C_1$–$C_4$ alkyl radicals,

R₂₉ and R₃₀, which may be identical or different, are chosen from a hydrogen atom and $C_1$–$C_4$ alkyl radicals;

c) compounds of formulae (VII) and (VII') below;

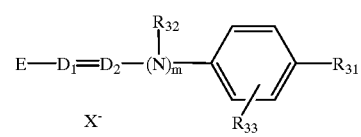

(VII)

-continued (VII')

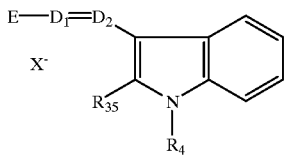

in which:

R$_{31}$ is chosen from a hydrogen atom, C$_1$–C$_4$ alkoxy radicals, halogen atoms and an amino radical, R$_{32}$ is chosen from a hydrogen atom and C$_1$–C$_4$ alkyl radicals or forms, with a carbon atom of the benzene ring, a heterocycle which is optionally oxygenated or substituted with at least one C$_1$–C$_4$ alkyl radical, R$_{33}$ is chosen from a hydrogen atom and halogen atoms, R$_{34}$ and R$_{35}$, which may be identical or different, are chosen from a hydrogen atom and C$_1$–C$_4$ alkyl radicals, D$_1$ and D$_2$, which may be identical or different, are chosen from a nitrogen atom and a —CH group, m=0 or 1, wherein, when R$_{31}$ is an unsubstituted amino group, D$_1$ and D$_2$ are both a —CH group and m=0, X$^-$ is chosen from anions, E is a group chosen from structures E1 to E8 below:

E1

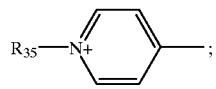

E2

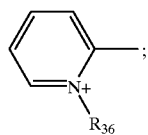

E3

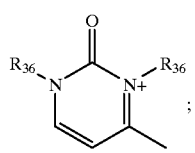

E4

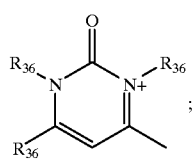

E5

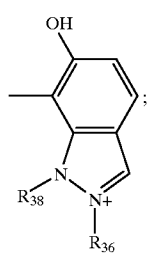

-continued

E6

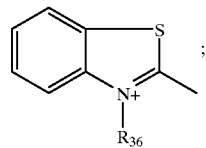

E7

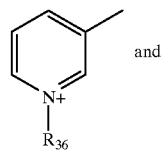

E8

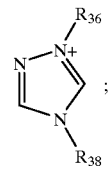

in which:

R$_{36}$ is chosen from C$_1$–C$_4$ alkyl radicals; and when m=0 and when D$_1$ is a nitrogen atom, E can also be chosen from a group of structure E9 below:

E9

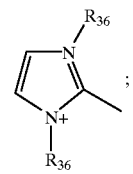

in which:

R$_{36}$ is chosen from C$_1$–C$_4$ alkyl radicals, and d) the compound of formula (V43) below:

(V43)

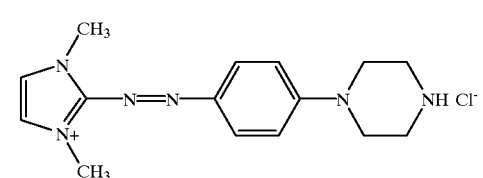

and wherein said second composition comprises:

at least one enzyme chosen from 2-electron oxidoreductases, and at least one donor for said at least one enzyme.

52. A multi-compartment dyeing kit, comprising at least two separate compartments wherein a first compartment contains a first composition and a second compartment contains a second composition, wherein said first composition comprises:

at least one oxidation base, and at least cationic direct dye chosen from a) compounds of formula (V) below:

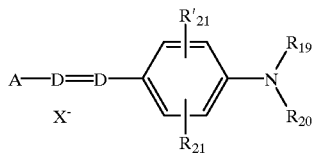

(V)

in which:

D is chosen from a nitrogen atom and a —CH group, $R_{19}$ and $R_{20}$, which may be identical or different, are chosen from a hydrogen atom; $C_1$–$C_4$ alkyl radicals, and a 4'-aminophenyl radical; or form, with a carbon atom of the benzene ring of formula (V), a heterocycle, $R_{21}$ and $R'_{21}$, which may be identical or different, are chosen from a hydrogen atom, halogen atoms, a cyano group, $C_1$–$C_4$ alkoxy radicals and acetyloxy radicals, $X^-$ is chosen from anions, A is a group chosen from structures A1 to A19 below:

$A_1$

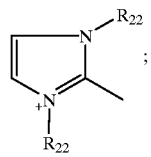

$A_2$

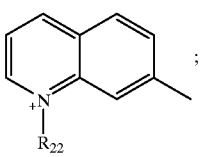

$A_3$

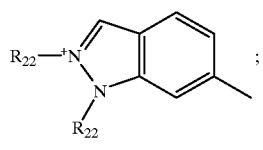

$A_4$

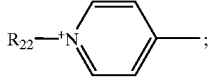

$A_5$

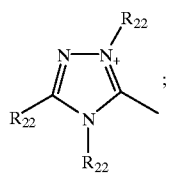

$A_6$

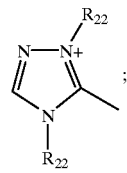

$A_7$

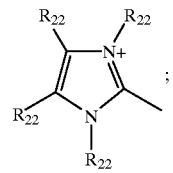

$A_8$

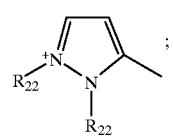

$A_9$

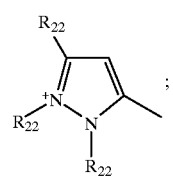

$A_{10}$

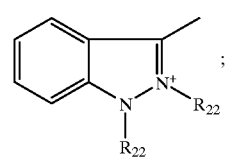

$A_{11}$

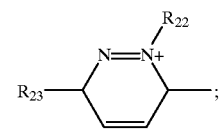

$A_{12}$

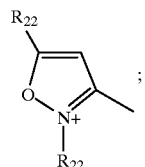

$A_{13}$

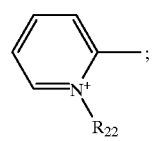

$A_{14}$

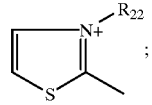

$A_{15}$

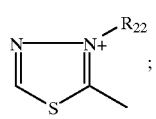

$A_{16}$

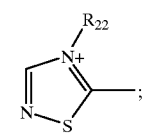

-continued

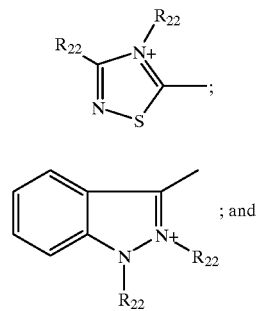

A17

A18 ; and

A19 in which:

R22 is chosen from $C_1$–$C_1$ alkyl radicals which can be substituted with a hydroxyl radical, and R23 is chosen from $C_1$–$C_4$ alkoxy radicals;

b) compounds of formula (VI) below,

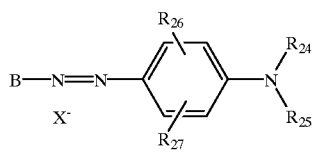

(VI)

in which:

R24 is chosen from a hydrogen atom and $C_1$–$C_4$ alkyl radicals,

R25 is chosen from a hydrogen atom, alkyl radicals, and a 4'-aminophenyl radical or forms, with R24, a heterocycle, R26 and R27, which maybe identical or different, are chosen from a hydrogen atom, halogen atoms, $C_1$–$C_4$ alkyl radicals, $C_1$–$C_4$ akoxy radicals and a —CN radical, X⁻ is chosen from anions, B is a group chosen from structures B1 to B9 below:

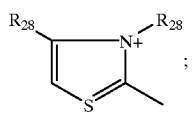

B1

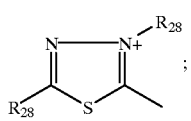

B2

-continued

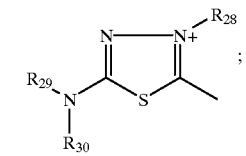

B3

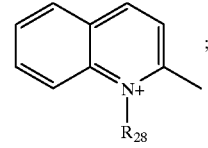

B4

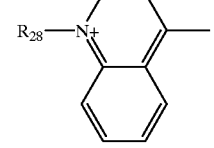

B5

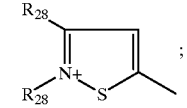

B6

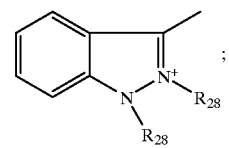

B7

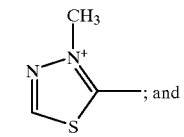

B8 ; and

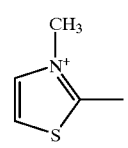

B9 in which:

R28 is chosen from $C_1$–$C_4$ alkyl radicals,

R29 and R30, which may be identical or different, are chosen from a hydrogen atom and $C_1$–$C_4$ alkyl radicals;

c) compounds of formulae (VII) and (VII') below:

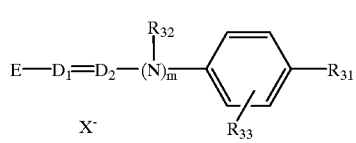

(VII)

-continued (VII')

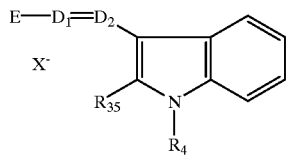

in which:

R$_{31}$ is chosen from a hydrogen atom, C$_1$–C$_4$ alkoxy radicals, halogen atoms and an amino radical, R$_{32}$ is chosen from a hydrogen atom and C$_1$–C$_4$ alkyl radicals or forms, with a carbon atom of the benzene ring, a heterocycle which is optionally oxygenated or substituted with at least one C$_1$–C$_4$ alkyl radical, R$_{33}$ is chosen from a hydrogen atom and halogen atoms, R$_{34}$ and R$_{35}$, which may be identical or different, are chosen from a hydrogen atom and C$_1$–C$_4$ alkyl radicals, D$_1$ and D$_2$, which may be identical or different, are chosen from a nitrogen atom and a —CH group, m=0 or 1, wherein, when R$_{31}$ is an unsubstituted amino group, D$_1$ and D$_2$ are both a —CH group and m=0, X$^-$ is chosen from anions, E is a group chosen from structures E1 to E8 below:

E1

E2

E3

E4

E5

-continued

E6

E7

E8 in which:

R$_{36}$ is chosen from C$_1$–C$_4$ alkyl radicals; and when m=0 and when D$_1$ is a nitrogen atom, E can also be chosen from a group of structure E9 below:

E9 in which:

R$_{36}$ is chosen from C$_1$–C$_4$ alkyl radicals, and d) the compound of formula (V43) below;

(V43)

wherein said second composition comprises;

at least one enzyme chosen from 2electron oxidoreductases, and at least one donor for said at least one enzyme.

* * * * *

UNITED STATES PATENT AND TRADEMARK OFFICE
CERTIFICATE OF CORRECTION

PATENT NO.    : 6,228,129 B1
DATED         : May 8, 2001
INVENTOR(S)   : Roland de la Mettrie et al.

It is certified that error appears in the above-identified patent and that said Letters Patent is hereby corrected as shown below:

Column 60,
Line 34, "1-benzyl4" should read -- 1-benzyl-4 --.

Column 73,
Line 25, close space between "d" and "i".

Column 76,
Line 20, " 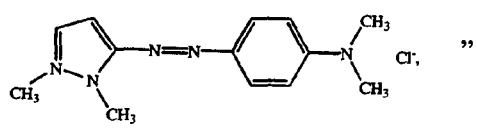 "

should read -- 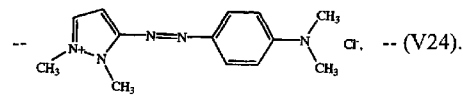 -- (V24).

Column 87,
Line 40, " 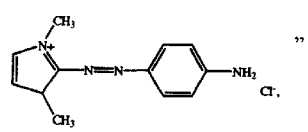 "

should read -- 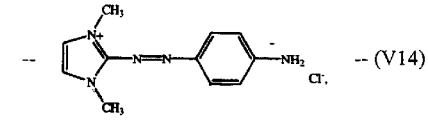 -- (V14)

Column 102,
Line 66, "cabonic" should read -- cationic --.

Column 111,
Line 26, "$C_1$-$C_1$" should read -- $C_1$-$C_4$ --.

UNITED STATES PATENT AND TRADEMARK OFFICE
CERTIFICATE OF CORRECTION

PATENT NO. : 6,228,129 B1
DATED : May 8, 2001
INVENTOR(S) : Roland de la Mettrie et al.

It is certified that error appears in the above-identified patent and that said Letters Patent is hereby corrected as shown below:

Column 113,
Line 33, "$R_{35}$" should read -- $R_{36}$ --.
Line 62, "$R_{38}$" should read -- $R_{36}$ --.

Column 114,
Line 22, "$R_{38}$" should read -- $R_{36}$ --.
Line 59, "2electron" should read -- 2-electron --.

Signed and Sealed this

Eleventh Day of March, 2003

JAMES E. ROGAN
*Director of the United States Patent and Trademark Office*